United States Patent
Aboagye et al.

(10) Patent No.: US 8,961,930 B2
(45) Date of Patent: Feb. 24, 2015

(54) ISATIN DERIVATIVES FOR USE AS IN VIVO IMAGING AGENTS

(75) Inventors: Eric Ofori Aboagye, Middlesex (GB); Graham Smith, London (GB); Quang-De Nguyen, London (GB); Erik Arstad, London (GB); Matthias Eberhard Glaser, London (GB)

(73) Assignees: Imperial Innovations Limited, London (GB); Hammersmith Imanet Limited, London (GB)

( * ) Notice: Subject to any disclaimer, the term of this patent is extended or adjusted under 35 U.S.C. 154(b) by 443 days.

(21) Appl. No.: 13/062,064

(22) PCT Filed: Sep. 4, 2009

(86) PCT No.: PCT/GB2009/002132
§ 371 (c)(1),
(2), (4) Date: Mar. 3, 2011

(87) PCT Pub. No.: WO2010/026388
PCT Pub. Date: Mar. 11, 2010

(65) Prior Publication Data
US 2011/0195024 A1 Aug. 11, 2011

(30) Foreign Application Priority Data

Sep. 5, 2008 (GB) .................................. 0816294.3
Oct. 2, 2008 (GB) .................................. 0818076.2

(51) Int. Cl.
*A61K 49/00* (2006.01)
*C07D 403/12* (2006.01)
*C07D 403/14* (2006.01)
*C07D 405/14* (2006.01)
*A61K 51/00* (2006.01)
*A61M 36/14* (2006.01)

(52) U.S. Cl.
CPC ............ *C07D 403/12* (2013.01); *C07D 403/14* (2013.01); *C07D 405/14* (2013.01)
USPC ........................................ 424/1.89; 424/9.1

(58) Field of Classification Search
USPC ....................................................... 424/9.1
See application file for complete search history.

(56) References Cited

U.S. PATENT DOCUMENTS

2005/0250798 A1  11/2005  Dollings et al.

FOREIGN PATENT DOCUMENTS

| GB | 1240648 | 7/1971 |
| WO | 9906367 | 2/1999 |
| WO | 0122966 | 4/2001 |
| WO | 2005053752 A2 | 6/2005 |
| WO | 2005067388 A2 | 7/2005 |
| WO | 2006067376 A2 | 6/2006 |
| WO | 2006/074799 A1 | 7/2006 |

OTHER PUBLICATIONS

D. Zhou, et al., "Synthesis, Radiolabeling, and in vivo evaluation of caspase-3 activation in apoptosis", Bioorganic and Medicinal Chemistry Letters, vol. 16, 2006, pp. 5041-5046.
K. Kopka, et al., "5-Pyrrolidinylsulfinyl Isatins as a Potential Tool for the Molecular Imaging of Caspases in Apoptosis", Journal of Medicinal Chemistry, vol. 49, No. 23, 2006, pp. 6704-6715.
G. Smith, et al., "Design, Synthesis, and Biological Characterization of a Caspase 3/7 Selective Isatin Labeled with 2-[18F]fluoroethylazide", Journal of Medicinal Chemistry, vol. 51, Dec. 2, 2008, pp. 8057-8067.
Establishment and Characterization of a Human Lung Cancer Cell Line NCI-H460-LNM35 with Consistent Lymphogenous Metastasis via Both Subcutaneous and Orthotopic Propagation, Cancer Research, Ken-ichi Kozaki, et al., Cancer Res 2000;60:2535-2540, May 1, 2000.
Characterization and Properties of Nine Human Ovarian Adenocarcinoma Cell Lines, Cancer Research, Simon P. Langdon, et al., Cancer Res 1988;48:6166-6172, Nov. 1, 1988.
United Kingdom Co-ordinating Committee on Cancer Research (UKCCCR) Guidelines for the Welfare of Animals in Experimental Neoplasia (Second Edition), British Journal of Cancer (1998) 77(1), Jul. 1-10, 1997.
In vivo evaluation of [18F] fluoroetanidazole as a new marker for imaging tumour hypoxia with positron emission tomography, British Journal of Cancer (2004) 90, 2232-2242, May 2004.
The nonpeptidyl caspase binding radioligand (S)-1-(4-(2-[18F]Fluoroethoxy)-benzyl)-5-[1-(2-methoxymethylpyrrolidinyl) sulfonyl]isatin ([18F]CbR) as potential positron emission tomography-compatible apoptosis imaging agent, A. Faust, et al., The Quarterly Journal of Nuclear Medicine and Molecular Imaging, vol. 51, No. 1, 2007;51:67-73.
Potent and Selective Nonpeptide Inhibitors of Caspases 3 and 7 Inhibit Apoptosis and Maintain Cell Functionality, The Journal of Biological Chemistry, vol. 275, No. 21, Issue of May 26, 2000, pp. 16007-16014.
Molecular imaging of cell death in vivo by a novel small molecule probe, Apoptosis (2006) 11:2089-2101, Revital Aloya, et al., Published online: Oct. 17, 2006.
Past, Present, and Future of Annexin A5: From Protein Discovery to Clinical Applications, Hendrikus H. Boersma, et al., J Nucl Med 2005; 46:2035-2050.
Click for PET: rapid preparation of [18F]fluoropeptides using CuI catalyzed 1, 3-dipolar cycloaddition, Jan Marik, et al., Science Direct, Tetrahedron Letters 47 (2006) pp. 6681-6684.
Apoptosis-detecting radioligands: current state of the art and future perspectives, Christophe M. M. Lahorte, et al., European Journal of Nuclear Medicine and Moleculor Imaging vol. 31, No. 6, Jun. 2004, pp. 887-919.

(Continued)

*Primary Examiner* — Michael G Hartley
*Assistant Examiner* — Melissa Perreira
(74) *Attorney, Agent, or Firm* — Kirschstein, et al.

(57) ABSTRACT

Isatin 5-sulfonamide derivatives, pharmaceutical compositions comprising the derivatives, their use as molecular imaging agents, their use for the diagnosis or treatment of diseases or disorders associated with dysregulation of apoptosis, methods for synthesizing the derivatives, methods for the molecular imaging of caspase activity and apoptosis, and methods of assessing the therapeutic effect of a test substance on caspase activity are disclosed.

8 Claims, 28 Drawing Sheets

(56) References Cited

OTHER PUBLICATIONS

ApoSense: a novel technology for functional molecular imaging of cell death in models of acute renal tubular necrosis, Maya Damianovich, et al., European Journal of Nuclear Medicine and Moleculor Imaging vol. 33, No. 3, Mar. 2006, pp. 281-291.

Symposium: Programmed Cell Death-Clinical Reality and Therapeutic Strategies, Apoptosis in Cardiac Disease—What is it—How Does it Occur, Cardiovascular Drugs and Therapy 15 pp. 507-523, 2001.

Potent and Selective Nonpeptide Inhibitors of Caspases 3 and 7, Dennis Lee, et al., J. Med. Chem. 2001, 44, pp. 2015-2026.

N-Benzylisatin Sulfonaminde Analogues as Potent Caspase-e Inhibitors: Synthesis, in Vitro Activity, and Molecular Modeling Studies, Wenhun Chu, et al., J. Med. Chem. 2005, 48, pp. 7637-7647.

Isatin Sulfonamide Analogs Containing a Michael Addition Acceptor: A New Class of Caspase 3/7 Inhibitors, Wenhua Chu, et al., J. Med. Chem 2007, 50, pp. 3751-3755.

"Click Labeling" with 2-[18F]Fluoroethylazide for Positron Emission Tomography, Matthias Glaser, et al., Bioconjugate Chem. 2007, 18, pp. 989-993.

Synthesis and biological evaluation of deoxypreussomerin A and palmarumycin CP1 and related naphthoquinone spiroketals, Peter Wipf, et al., Tetrahedron 57 (2001) pp. 283-296.

Bioreductive Metabolism of the Novel Fluorinated 2-Nitroimidazole Hypoxia Probe N-(2-Hydroxy-3,3,3-trifluoropropyl)-2-(2-nitroimidazolyl) Acetamide (SR-4554), Eric O. Aboagye, et al., Biochemical Pharmacology, vol. 54, pp. 1217-1224, 1997.

A New Mouse Tumor Model System (RIF-1) for Comparison of End-Point Studies, Peter R. Twentyman, et al., JNCI, vol. 64, No. 3, Mar. 1980, pp. 595-604.

Cellular Heterogeneity and Drug Resistance in Two Ovarian Adenocarcinoma Cell Lines Derived From a Single Patient, C. Roland Wolf, et al., Int. J. Cancer: 39, pp. 695-702, 1987.

Rapid in situ synthesis o f [11C]methyl azide and its application in 11C click-chemistry, Ralf Schirrmacher, et al., Tetrahedron Letters 49 (2008) pp. 4824-4827.

An efficient F-18 labeling method for PET study: Huisgen 1, 3-dipolar cycloaddition of bioactive substances and F-18-labeled compounds, Uthaiwan Sirion, et al., Tetrahedron Letters 48 (2007) pp. 3853-3957.

Click Chemistry for 18F-Labeling of RGD Peptides and microPET Imaging of Tumor Integrin αvβ3 Expression, Zi-Bo Li, et al., Bioconjugate Chem. 2007, 18 pp. 1987-1994.

ISATIN DERIVATIVES FOR USE AS IN VIVO IMAGING AGENTS

The present invention provides novel isatin 5-sulfonamide derivatives, and their use as molecular imaging agents in the visualization and quantitation of caspase activity and caspase-dependent apoptosis, and in therapeutic applications.

Apoptosis or programmed cell death (PCD) is the most prevalent cell death pathway and proceeds via a highly regulated, energy conserved mechanism. In a healthy state, apoptosis plays a pivotal role in controlling cell growth, regulating cell number, facilitating morphogenesis, and removing harmful or abnormal cells. Dysregulation of this process has been implicated in a number of disease states, including those associated with the inhibition of apoptosis, such as cancer and autoimmune disorders, and those associated with hyperactive apoptosis, including neurodegenerative diseases, haematologic diseases, AIDS, ischaemia and allograft rejection. The visualization and quantitation of apoptosis is therefore useful in the diagnosis of such apoptosis-related pathophysiology.

Therapeutic treatments for these diseases aim to restore balanced apoptosis, either by stimulating or inhibiting this process. Non-invasive imaging of apoptosis in cells and tissue is therefore of immense value for early assessment of a response to therapeutic intervention, and can provide new insight into devastating pathological processes. Of particular interest is early monitoring of the efficacy of cancer therapy to ensure that malignant growth is controlled before the condition becomes terminal.

Of the probes available for imaging cell death, radiolabelled Annexin V has received the most attention[1,2]. However, Annexin V can only detect events at the outer cell surface and not inside the cell, and binds only to negatively charged phospholipids, which renders it unable to distinguish between apoptosis and necrosis. With regard to membrane-interacting probes, a number of di-dansyl cysteine and naphthyl-ethyl-fluoroalanine derivatives have been developed to image apoptosis[3,4,5]. However, such membrane-interacting probes also suffer from low specificity to apoptotic cells, and are unable to distinguish between apoptosis and necrosis without the need for a separate test[6]. More recently, there has been growing interest in the development of specific compounds that bind to a family of enzymes called caspases.

Caspases are a family of cysteine aspartate-specific proteases which play a central role in the regulation of apoptosis. Intrinsic and extrinsic signaling networks activate 'initiator' caspases 8 (extrinsic) or 9 (intrinsic), which in turn cleave the inactive pro-caspases 3, 6 and 7 into the active 'executioner' caspases 3, 6, and 7. The executioner caspases ultimately effect cellular death through cleavage of cellular proteins, which occurs to the right of aspartate residues in a highly selective manner. The proteins cleaved include DNA repair enzymes (e.g. PARP), key signaling proteins (e.g. Akt, Ras), nuclear skeletal proteins (e.g. actin, α-fodrin, lamins) and cell cycle regulators (e.g. p27Kip1).

The use of peptide-based irreversible inhibitors of caspases, such as [131I]IZ-VAD-fmk, as molecular imaging agents has been unsatisfactory as they are only moderately selective and have poor cell permeabilities, such that the uptake into cells is insufficient for in vivo imaging.

More recently, a group of chemicals known as isatins have been investigated as potential caspase inhibitors. The mechanism of action of isatins is believed to involve the formation of an intracellular enzyme-inhibitor complex with caspase 3 and 7 through covalent binding to the enzyme active site of the activated caspase. The dicarbonyl functionality of isatins is essential to its mechanism of action; it binds to the cysteine residue of the active site forming a thiohemiketal via the electrophilic C-3 carbonyl carbon of the isatin and the nucleophilic cysteine thiolate functionality[7].

Following a high through-put screen, Lee et al. identified the non-peptide isatin N-(1-methyl)-5-nitroisatin as an inhibitor of caspase-3. Structural optimization led to the development of the sulfonamide (S)-1-benzyl-5-(2-phenoxymethyl-pyrrolidine-1-sulfonyl)isatin (2.5 nM)[8] (denoted compound 13 herein). Other isatin sulfonamides were developed as inhibitors of caspase 3 and 7[9-12]. Kopka[13] and Mach[14] independently developed the [18F]-labeled (S)-1-(4-(2-fluoroethoxy)benzyl)-5-[1-(2-phenoxymethylpyrrolidinyl) sulfonyl]isatin as a putative tracer for positron emission tomography (PET), and Kopka[13] investigated the biological properties of a radioiodinated analog [125I] ((S)-1-(4-iodobenzyl)-5-(2-phenoxymethyl-pyrrolidine-1-sulfonyl)isatin) (denoted compound 14 herein). WO 99/06367 and WO01/22966 describe a number of isatin derivatives and their use for the inhibition of caspases. WO 2006/074799, US 2005/0250798 and GB 1,240,648 describe a number of isatin 5-sulfonamide derivatives and their use as imaging agents for apoptosis. However, these known compounds suffer from a number of disadvantages, including low molecular stability, relatively low caspase-3 affinity and high lipophilicity. Low molecular stability results in rapid metabolism, which results in poorly contrasted images with a low signal-to-noise ratio. Low caspase-3 affinity can also result in poorly contrasted images. High lipophilicity results in poor system elimination, and can increase generic non-specific binding to macromolecules.

It is therefore an object of the present invention to provide novel isatin derivatives with increased molecular stability, increased affinity for caspase enzymes and reduced lipophilicity.

The first aspect of the present invention provides novel isatin 5-sulfonamide derivatives of Formula A:

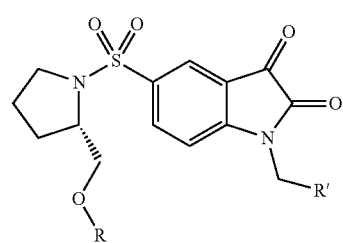

or a salt, hydrate or prodrug thereof, wherein:
R is phenyl, 3-fluorophenyl, 2,4-difluorophenyl, 3,5-difluorophenyl, an optionally substituted tetrahydropyran, an optionally substituted diazine and an optionally substituted triazole; R' is an optionally substituted phenyl or an optionally substituted triazole;
wherein when R is phenyl; R' is an optionally substituted triazole.

In a preferred embodiment, R comprises an optionally substituted triazole, and R' comprises an optionally substituted phenyl. In another preferred embodiment, R comprises an optionally substituted phenyl, and R' comprises an optionally substituted triazole.

Preferably, the optionally substituted phenyl, the optionally substituted tetrahydropyran and the optionally substituted diazine are optionally substituted with one or more electron withdrawing groups. Preferably, said electron withdrawing group is selected from the group comprising a halogen, a nitro group and a carboxylic acid group or other carbonyl containing functionality such as aldehyde or ketone. Most preferably, said electron withdrawing group is a halogen. Preferably, said halogen is fluorine.

Preferably, the optionally substituted phenyl is 2,4-difluorophenyl.

In one embodiment, the optionally substituted triazole is optionally substituted with a substituted alkyl. Preferably, said substituted alkyl is a halogen-substituted alkyl. More preferably, said halogen-substituted alkyl is a $C_{1-4}$fluoroalkyl. Preferably, said $C_{1-4}$ fluoroalkyl is fluoromethyl, 2-fluoroethyl, 3-fluoropropyl or 4-fluorobutyl. Most preferably, said $C_{1-4}$ fluoroalkyl is 2-fluoroethyl.

In an alternative embodiment, the optionally substituted triazole is optionally substituted with an alkyl. Preferably, said alkyl is methyl.

It will be appreciated by a person skilled in the art that the present invention also comprises all stereoisomers of the compounds of the present invention, including their enantiomers and diastereoisomers. The compounds of the present invention may exist in the form of substantially pure solutions of specific enantiomers or as racemic mixtures. Preferably, the compounds of the present invention exist as a substantially pure solution of the S enantiomer, or a solution consisting essentially of the S enantiomer. Preferably, in a racemic mixture comprising both the S enantiomer and the R enantiomer, said S enantiomer comprises at least 50% of the compounds of the present invention in said racemic mixture. More preferably, said S enantiomer comprises at least 60%, at least 70%, at least 80%, at least 90% at least 95% or at least 99% of the compounds of the present invention in said racemic mixture.

Particularly preferred compounds of the present invention include compounds of Formula A where R and R' are defined as follows:

| Compound No. | R | R' |
|---|---|---|
| 1 | 3-fluorophenyl | 4-fluorophenyl |
| 2 | 2,4-difluorophenyl | 4-fluorophenyl |
| 3 | 3,5-difluorophenyl | 4-fluorophenyl |
| 4 | tetrahydropyran-4-yl | 4-fluorophenyl |
| 5 | pyrimidin-5-yl | 4-fluorophenyl |
| 6 | 2,4-difluorophenyl | 1-(fluoromethyl)-1H-1,2,3-triazol-4-yl (N-linked) |
| 7 | 2,4-difluorophenyl | 1-(2-fluoroethyl)-1H-1,2,3-triazol-4-yl (N-linked) |
| 8 | 2,4-difluorophenyl | 1-(3-fluoropropyl)-1H-1,2,3-triazol-4-yl (N-linked) |
| 9 | 2,4-difluorophenyl | 1-(4-fluorobutyl)-1H-1,2,3-triazol-4-yl (N-linked) |
| 10 | phenyl | 1-(2-fluoroethyl)-1H-1,2,3-triazol-4-yl (C-linked) |
| 11 | 2,4-difluorophenyl | 1-(2-fluoroethyl)-1H-1,2,3-triazol-4-yl (C-linked) |

-continued

| Compound No. | R | R' |
|---|---|---|
| 29 | 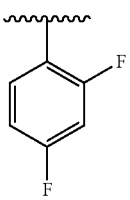 [SMILES: *c1ccc(F)cc1F] | 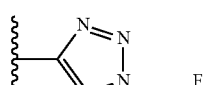 |
| 30 | 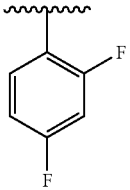 [SMILES: *c1ccc(F)cc1F] | 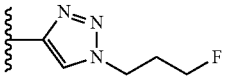 |
| 31 | 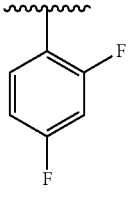 [SMILES: *c1ccc(F)cc1F] | 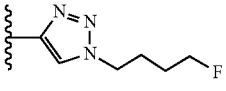 [SMILES: *c1cn(CCCCF)nn1] |
| 12 | 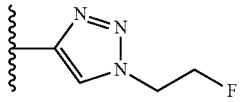 [SMILES: *c1cn(CCF)nn1] | 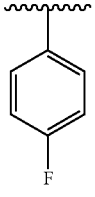 [SMILES: *c1ccc(F)cc1] |
| 32 | 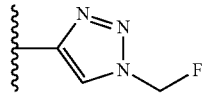 [SMILES: *c1cn(CF)nn1] | 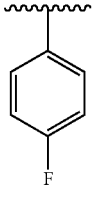 [SMILES: *c1ccc(F)cc1] |
| 33 | 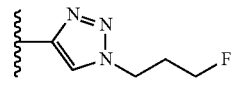 [SMILES: *c1cn(CCCF)nn1] | 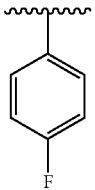 [SMILES: *c1ccc(F)cc1] |
| 34 | 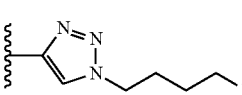 | 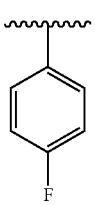 |

Preferably, the term 'salts' includes salts derived from organic and inorganic acids such as acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example sodium, lithium or potassium, when a compound of this invention contains a carboxylate or phenolic moiety, or similar moiety capable of forming base addition salts.

The term 'hydrate' as used herein refers to forms of the compounds of the present invention which have been chemically combined with water.

The term 'prodrug' as used herein refers to a compound which is convertible in vivo by metabolic means to a compound of the present invention.

As used herein, the phrase 'optionally substituted phenyl' refers to a phenyl group which may optionally comprise one or more substituents placed at one or more of ring positions 2, 3, 4, 5, and 6.

The term 'tetrahydropyran' as used here refers to an organic compound consisting of a saturated six-membered ring containing five carbon atoms and one oxygen atom.

The term 'triazole' as used herein refers to compounds with molecular formula $C_2HN_3$, having a five-membered ring of two carbon atoms and three nitrogen atoms. These compounds include the isomers 1,4- and 1,5-disubstituted 1,2,3 triazoles.

The term 'halogen' as used herein refers to bromine, chlorine, fluorine and iodine.

As used herein, the term 'alkyl' refers to an aliphatic hydrocarbon chain and includes, but is not limited to, straight or branched chains having 1, 2, 3, 4, 5 or 6 carbon atoms unless otherwise specified. Alkyls include methyl, ethyl, n-propyl, iso-propyl, n-butyl, sec-butyl, iso-butyl, tert-butyl and the like.

The phrase 'substituted alkyl' as used herein refers to an alkyl additionally comprising one or more substituents selected from the group comprising halogen, hydroxyl, thiol, amino, an alternative heteroatom, an aromatic or heteroaromatic group and spacer groups such as a polyether, including polyethylene glycol, succinidyl, —NH—(CH$_2$)n-NH— and polyamides.

The term 'diazine' as used herein refers to a group of organic compounds having the molecular formula $C_4H_4N_2$, each of which contains a benzene ring in which two of the carbon atoms are replaced by nitrogen. These compounds include the isomers pyrazine (1,4-diazine), pyrimidine (1,3-diazine) and pyridazine (1,2-diazine).

The compounds of the present invention are specific to activated caspases and have high affinity therefore. They are potent and selective inhibitors of caspases 3 and 7. In particular, the compounds of the present invention have high affinity for caspase-3 and caspase-7. They are only expressed in active form during apoptosis, and the activity of caspase-3 and/or caspase-7 is therefore a reliable indicator of caspase-dependent apoptosis.

The compounds of the present invention have reduced lipophilicity in comparison with many known isatin 5-sulfonamide derivatives, which allows good systemic elimination and reduces generic non-specific binding to macromolecules. However, caspases are intracellular proteases, therefore the compounds of the present invention are still lipophilic enough to cross cell membranes by non-facilitated diffusion, in order that they can freely pass into and out of a cell. As such, the compounds will have rapid bi-directional uptake and retention only in cells with activated caspase-3 and/or caspase-7. The ideal lipophilicity (expressed as Log P) varies depending upon the cell type into which the compounds are required to pass, in addition to a number of other factors. In one embodiment, lipophilicity is preferably in the region of 1.0 to 2.0.

Compounds of the present invention have increased metabolic stability, which reduces the rate at which the compounds are metabolized and, in some cases, excreted. Increased metabolic stability allows the accumulation of the compound of the present invention in cells undergoing apoptosis, upon binding with activated caspases. This provides well contrasted images with a high signal-to-noise ratio. This is advantageous in a molecular imaging agent, as it allows accurate visualization and quantitation of caspase activity within cells and tissues.

Preferably, the compounds of the present invention have low uptake in untreated tumours, heart and brain tissue. This facilitates the monitoring of changes in the binding of these compounds to activated caspases in mammalian tissues, which is associated with changes in caspase activity.

The second aspect of the present invention provides the compounds of the first aspect of the present invention, wherein said compounds are labeled with an imaging moiety.

Said labelling may comprise an imaging moiety within a functional group, or the attachment of an imaging moiety as an additional species.

Said imaging moiety may comprise any moiety capable of producing a detectable signal. Such moieties include fluorescent labels and radiolabels.

Fluorescent labels comprise a covalently attached fluorophore. Preferred fluorophores include fluorescein isothiocyanate, derivatives of rhodamine, coumarin and cyanine dyes, Alexa Fluors and DyLight Fluors.

Preferably, the compounds are labeled with a radioisotope. The use of a radioisotope as an imaging moiety is advantageous, as the radioisotope does not significantly increase the molecular weight of the compound of the present invention, and can be used for clinical non-invasive imaging.

Preferably, the radioisotope is a positron-emitter. The radioactive isotope can be selected from the group comprising $^{3}H$, $^{14}C$, $^{18}F$, $^{11}C$, $^{120}I$, $^{123}I$, $^{124}I$, $^{125}I$, $^{131}I$, $^{94m}Tc$, $^{66}Ga$, $^{68}Ga$, $^{64}Cu$, $^{61}Cu$, $^{67}Cu$, $^{75}Br$, $^{76}Br$, $^{94m}Tc$, $^{99m}Tc$, $^{201}Tl$, $^{111}In$, $^{86}Y$ and $^{89}Zr$.

If the imaging moiety is to be imaged using Positron Emission Tomography (PET), the radioactive isotope is preferably selected from the group comprising $^{18}F$, $^{11}C$, $^{120}I$, $^{124}I$, $^{94m}Tc$, $^{66}Ga$, $^{68}Ga$, $^{64}Cu$, $^{67}Cu$, $^{86}Y$, $^{75}Br$ and $^{76}Br$.

If the imaging moiety is to be imaged using Single Photon Emission Computed Tomography (SPECT), the radioactive isotope is preferably selected from the group comprising $^{123}I$, $^{99m}Tc$ and $^{111}In$.

Preferably, the imaging moiety is $^{18}F$ or $^{11}C$.

Preferably, in any of compounds 1 to 12 and 29 to 34, one or more of the fluorine atoms in R and/or R' is $^{18}F$.

Addition of a 1, 2, 3-triazole group at R or R', as, for example, in compounds, 6 to 12, and 29 to 36, has the additional advantage that the compound can readily be labeled with $^{18}F$ or $^{11}C$.

A particularly preferred embodiment of the invention has the formula:

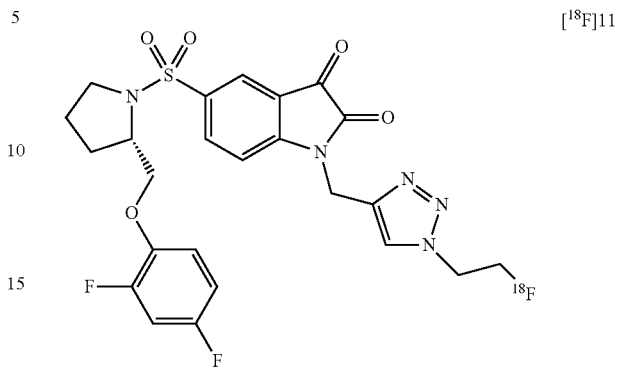

[$^{18}F$]11

Other preferred compounds of the present invention have the general formulae:

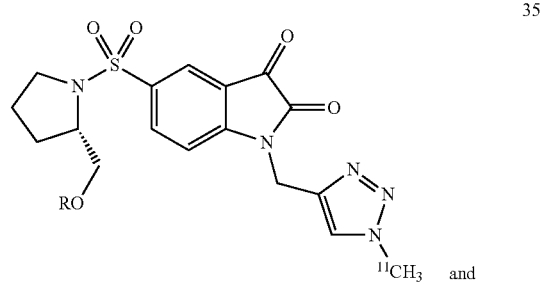

35 and

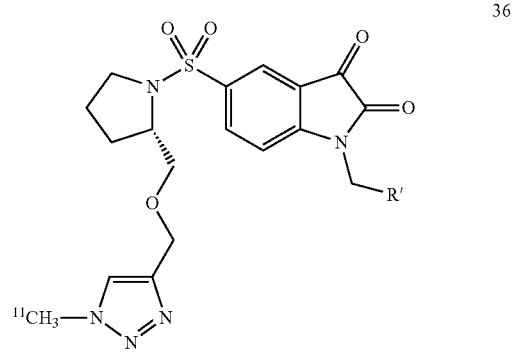

36 wherein R and R' are as defined above.

The third aspect of the present invention provides a composition comprising a compound according to the first aspect of the invention optionally in combination with one or more pharmaceutically acceptable carriers, diluents or excipients.

The fourth aspect of the present invention provides a composition comprising a compound according to the second aspect of the invention optionally in combination with one or more pharmaceutically acceptable carriers, diluents or excipients.

These compositions may also comprise one or more additional active agents. Said additional active agents may comprise agents that enhance the signal produced by the compounds of the present invention. Preferably, said active agents comprise compounds that deplete or modulate cellular glutathione levels, including diethyl maleate (DEM), L-buthionine-(S,R)-sulfoxime (BSO) and derivatives thereof.

The compositions of the third or fourth aspects of the present invention may be administered by any convenient method.

The compositions may be brought into contact with cells by exposing, incubating, touching, associating or making the compound accessible to cells.

The compositions may be administered to a subject by oral (including by inhalation), parenteral, mucosal (e.g. buccal, sublingual, nasal), rectal or transdermal administration, and the compositions adapted accordingly.

For oral administration, the compositions can be formulated as liquids or solids, for example solutions, syrups, suspensions or emulsions, tablets, capsules and lozenges.

A liquid formulation will generally consist of a suspension or solution of the compound or physiologically acceptable salt, hydrate or prodrug thereof in a suitable aqueous or non-aqueous liquid carrier(s) for example water, ethanol, glycerine, polyethylene glycol or oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatine capsule. Alternatively, a dispersion or suspension can be prepared using any suitable pharmaceutical carrier(s), for example aqueous gums, celluloses, silicates or oils and the dispersion or suspension then filled into a soft gelatine capsule.

Compositions for oral administration may be designed to protect the active ingredient against degradation as it passes through the alimentary tract, for example by an outer coating of the formulation on a tablet or capsule.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve, which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels, patches and injections including powder injections.

Conveniently the composition is in unit dose form such as a tablet, capsule or ampoule.

Preferably, the compounds or compositions of the present invention are administered to a subject by parenteral administration. In particular, the compositions may be administered intravenously, intraperitoneally, intrathecally, intralymphatically or intramuscularly.

Typical parenteral compositions consist of a parenterally acceptable solution or suspension of the compound or a physiologically acceptable salt in a sterile aqueous or non-aqueous carrier which has suitable pH, isotonicity and stability. Those of relevant skill in the art are able to prepare suitable solutions using, for example, isotonic vehicles such as sodium chloride injection, Ringer's injection, Lactated Ringer's injection. Preservatives, stabilisers, buffers, antioxidants and/or other additives may be included, as required.

The fifth aspect of the present invention provides the compounds of the first or second aspect of the present invention or the pharmaceutical compositions of the third or fourth aspect of the present invention for use as molecular imaging agents.

Preferably, said molecular imaging agents are for the visualization and quantitation of caspase activity in cells and tissues. Preferably, said molecular imaging agents are for the visualization and quantitation of caspase activity in mammalian cells and tissues, including human cells and tissues. Said quantitation may comprise the analysis of cellular or tissue radioactivity content, or the rate of uptake, dissociation or partitioning.

Upon the formation of a complex with active caspases, the uptake and accumulation of the labeled compound within the cells and tissues can then be imaged to indicate the level of caspase activity within those cells and tissues. The sixth aspect of the present invention therefore provides a method for the molecular imaging of caspase activity comprising the steps of:

a) contacting said cells or tissues with a compound of the second aspect of the present invention or composition of the fourth aspect of the present invention and:
b) detecting said caspase activity.

Preferably, the step of detecting said caspase activity comprises the steps of positioning the subject within the detection field of a detection device and detecting said compounds in the subject with said detection device.

This method may be carried out in vitro. Contacting the cells or tissues with a compound or composition of the present invention may involve exposing, incubating, touching, associating or making the compound accessible to the cells or tissue.

When the compound or composition of the present invention is radiolabelled, said caspase activity can be detected in vitro using any appropriate radiation detection device. Said device may include a beta counter, such as a Packard Topcount, or a gamma counter, such as a Packard Cobra II™ gamma counter (Perkin Elmer, UK), or a radio-TLC scanner.

When the compound or composition of the present invention is fluorescently labeled, said caspase activity can be detected in vitro using any appropriate fluorescence reading instrument. Such instruments include a fluorescence microscope, fluorometer, or a fluorescent plate reader, such as a Perkin Elmer Victor.

Alternatively, this method may be carried out in vivo. The compounds or compositions may be administered to a subject by any method discussed in the third and fourth aspect of the present invention. Preferably, the compounds are administered parenterally.

When the compound or composition of the present invention is radiolabelled, said caspase activity may be detected using a radiation detection device. Said radiation detection device may include a Positron Emission Tomography (PET)

scanner or a Single Photo Emission Computed Tomography (SPECT) scanner. Preferably, said radiation detection device is a Positron Emission Tomography (PET) scanner. Said PET scanner can detect pairs of gamma rays emitted indirectly by positron-emitting radioisotopes such as $^{18}F$ to produce a 3D image of the radioisotope concentration within tissues. PET can therefore be used to produce a 3D image of the localization of the radiolabelled compounds and compositions of the present invention within mammalian tissues.

When the compound or composition of the present invention is fluorescently labeled, said caspase activity may be detected using any appropriate fluorescence reading instrument. Said fluorescence reading instrument may include a fluorescence endoscope.

Preferably, the caspase activity is caspase-3 activity.

The present invention also provides the use of the compounds of the second aspect of the present invention for the manufacture of a pharmaceutical or diagnostic composition for the visualization and quantitation of caspase activity.

In an alternative embodiment of the sixth aspect, compounds according to the first aspect of the present invention or pharmaceutical compositions according to the third aspect of the present invention may be administered in part (a). Said compounds may then be fluorescently or radioactively labeled after said administration.

As discussed above, caspase enzymes effect apoptosis, and as such caspase activity can be used as an indicator of apoptosis. The seventh aspect of the present invention therefore provides the use of the compounds of the second aspect of the present invention or the pharmaceutical compositions of the fourth aspect of the present invention for in vivo imaging of caspase-dependent apoptosis in mammalian cells or tissue.

This method may involve:
a) administering to the subject a compound of the second aspect of the present invention or a composition of the fourth aspect of the present invention;
b) positioning the subject within the detection field of a detection device; and
c) detecting said compounds in the subject with said detection device.

Preferably said compound or composition is administered to the subject by injection.

The imaging moiety can either be detected externally in a non-invasive manner or internally by the use of detectors designed for use in vivo, such as intravascular radiation or optical detectors, or radiation detectors designed for intra-operative use. Preferably, the imaging moiety is detected in a non-invasive manner.

In one embodiment, said compounds are fluorescently labeled, and are detected by measuring the fluorescence emitted from the fluorescently labeled compounds with a fluorescence reading instrument as defined above in the sixth aspect.

In a second, preferred, embodiment, said compounds are radiolabelled, and are detected by measuring the radiation emitted from the radiolabelled compounds with a radiation detection device as defined above in the sixth aspect.

Preferably said caspase activity is caspase-3 activity.

In an alternative embodiment of the seventh aspect, compounds according to the first aspect of the present invention or pharmaceutical compositions according to the third aspect of the present invention may be administered in part (a). Said compounds may then be fluorescently or radioactively labeled in vivo, after said administration.

As discussed above, therapeutic treatments for numerous diseases aim to restore normal, balanced apoptosis by stimulating or inhibiting this process. The eighth aspect of the present invention therefore provides the use of the compounds of the second aspect of the present invention or the pharmaceutical compositions of the fourth aspect of the present invention for assessing the therapeutic effect of a test substance on caspase activity in mammalian cells or tissues.

This method may involve:
a) contacting mammalian cells or tissues with a compound of the second aspect of the present invention or a composition according to the fourth aspect of the present invention;
b) positioning said mammalian cells or tissues within the detection field of a detection device;
c) detecting the compounds with said detection device;
d) repeating steps a), b) and c).

In one embodiment, said compounds are fluorescently labeled, and are detected by measuring the fluorescence emitted from the fluorescently labeled compounds with a fluorescence reading instrument as defined above in the sixth aspect.

In a second, preferred, embodiment, said compounds are radiolabelled, and are detected by measuring the radiation emitted from the radiolabelled compounds with a radiation detection device as defined above in the sixth aspect.

In an alternative embodiment of the eighth aspect, compounds according to the first aspect of the present invention or pharmaceutical compositions according to the third aspect of the present invention may be administered in part (a). Said compounds may then be fluorescently or radioactively labeled after said administration.

Preferably, this method may be carried out in vivo and may involve;
a) administering to a subject a compound according to the second aspect of the present invention or a composition according to the fourth aspect of the present invention;
b) positioning the subject within the detection field of a radiation detection device;
c) measuring the radiation emitted from the radiolabelled compounds in the subject with said radiation detection device;
d) repeating steps a), b) and c).

For both the in vitro and in vivo methods of the eighth aspect, step d) is preferably carried out at selected time intervals wherein said repetition is effective to track changes in caspase activity over time. The time intervals of step d) should be appropriate to the subject and test substance in question. For humans, appropriate time intervals include but are not limited to 12 to 24 hours, 48 hours, 1 week, 2 weeks, 3 weeks, 4 weeks, 5 weeks or 6 weeks.

The caspase activity measured in each repetition can be compared to assess quantitative changes in the extent and localization of caspase activity, and therefore quantitative or semi-quantitative changes in caspase-dependent apoptosis, over time. Changes in the extent and localization of caspase activity may indicate a therapeutic effect of a test substance upon caspase-dependent apoptosis, either by stimulation or inhibition of caspase activity. This method can be used to evaluate the response of a subject to therapeutic treatment using established drugs, and the evaluation of the efficacy of new drugs.

The compound or composition of the present invention may be administered before, after or simultaneously with the test substance. Preferably, steps (a) to (c) are performed on a subject, before administration of the test substance to provide a first measure of caspase activity. The test substance is then administered and steps (a) to (c) are repeated after a time interval, as discussed above, to provide a second measure of caspase activity. Steps (a) to (c) may be repeated on further occasions, before or after further administrations of the test substance, to provide further measures of caspase activity.

Preferably, said compound or composition is administered to the subject by injection.

The test substance may comprise a drug or agent used to treat diseases including but not limited to cancer, autoimmune disease, haematologic disease, HIV, AIDS, ischemia, cardiovascular disease, neurological diseases and transplant rejection. In particular, the test substance may comprise chemotherapeutic, radiotherapeutic or immunotherapeutic agents for the treatment of cancer.

As stated above, steps (a) to (c) may be repeated two or more times. In one preferred embodiment, the compound administered to the subject in the first performance of step (a) is a compound according to the present invention which is radiolabelled with $^{11}C$. Preferably, said compound is selected from the group comprising compounds 35 and 36. Subsequently, the compound administered to the subject in the second performance of step (a) is a radiolabelled imaging agent. Said radiolabelled imaging agent may be, for example, fluorodeoxyglucose (FDG), 3'-deoxy-3'-$^{18}F$-fluorothymidine (FLT) or a compound according to the present invention. In one preferred embodiment, said imaging agent is labeled with $^{18}F$. This embodiment is particularly advantageous. Carbon-11 ($^{11}C$) has a relatively short half-life of 20 minutes. Thus, by using a compound labeled with $^{11}C$, there is little or no background noise during the second and subsequent scans. This results in a higher signal-to-noise ratio, and a more accurate visualization and quantitation of caspase activity and caspase-dependent apoptosis.

Similarly, if the methods according to the sixth and seventh aspect of the present invention are to be repeated within a relatively short space of time, the use of a $^{11}C$-labelled compound followed by an alternative radiolabelled imaging agent, such as an $^{18}F$-labelled compound, would also reduce the background noise present during the second scan, and increase the signal-to-noise ratio.

The ninth aspect of the present invention provides compounds according to the first aspect of the present invention or the compositions according to the third aspect of the present invention for use in inhibiting caspase activity. This method may involve administering to a subject in need of such treatment an effective amount of the compounds of the first aspect of the present invention or the compositions of the third aspect of the present invention.

This aspect also provides the use of compounds of the first aspect of the present invention or the compositions of the third aspect of the present invention in the manufacture of a medicament for the inhibition of caspase activity.

As caspase enzymes effect apoptosis, the ninth aspect of the present invention also provides the compounds of the first aspect of the present invention or compositions of the third aspect of the present invention for use in the inhibition of apoptosis.

The inhibition of caspase activity may be effective to treat any disease or condition caused by or associated with excessive or inappropriate apoptosis. Examples of such diseases or conditions include neurodegenerative diseases including Alzheimer's disease, haematologic diseases, hepatocellular degeneration, osteoarthritis, AIDS, ischaemia and allograft rejection.

The compounds of the first aspect of the present invention or the compositions of the third aspect of the present invention will normally be administered to a subject in a daily dosage regimen. For example, a daily dosage regimen may require from about 0.001 to about 100 mg/kg, preferably from about 0.001 to about 10 mg/kg subject body weight. A daily dose, for a larger mammal, is preferably from about 1 mg to about 1000 mg, preferably between 1 mg and 500 mg, the compound being administered 1 to 4 times a day. Alternatively, given the stability of the compounds of the present invention, a dose could be administered 1, 2 or 3 times a week.

It is understood that the dosage, regimen and mode of administration of the compounds and compositions of the present invention will vary according to the disease or condition and the individual being treated, and will be subject to the judgement of the medical practitioner involved.

The tenth aspect of the present invention provides the compounds of the second aspect of the present invention or the compositions of the fourth aspect of the present invention for use in diagnosing pathophysiology. In particular, the compounds of the second aspect of the present invention or the compositions of the fourth aspect of the present invention can be used to diagnose diseases and disorders associated with excessive or inappropriate apoptosis, including but not limited to chronic heart failure, acute myocardial infarction, stroke, neurodegenerative disorders, autoimmune disease, focal haematologic disease, focal AIDS, ischemia (including cardiac ischemia), and transplant rejection.

This method may involve:
a) contacting mammalian cells or tissues with a compound of the second aspect of the present invention or a composition according to the fourth aspect of the present invention;
b) positioning said mammalian cells or tissues within the detection field of a detection device;
c) detecting said compounds with said detection device to provide quantitative measurements of the caspase activity within said mammalian cells or tissues, wherein caspase activity is indicative of the level of apoptosis.

In one embodiment, said compounds are fluorescently labeled, and are detected by measuring the fluorescence emitted from the fluorescently labeled compounds with a fluorescence reading instrument as defined above in the sixth aspect.

In a second, preferred, embodiment, said compounds are radiolabelled, and are detected by measuring the radiation emitted from the radiolabelled compounds with a radiation detection device as defined above in the sixth aspect.

Preferably, said measurements are then compared with standard values to allow diagnosis of pathophysiology.

In an alternative embodiment of the tenth aspect, compounds according to the first aspect of the present invention or pharmaceutical compositions according to the third aspect of the present invention may be administered in part (a). Said compounds may then be fluorescently or radioactively labeled after said administration.

The eleventh aspect of the present invention provides methods of synthesizing compounds of the first aspect of the present invention. The compounds of the first aspect of the present invention may be prepared in any suitable manner. The schemes described in Examples 1, 3 and 10 and illustrated in FIGS. 1, 2(i), 2(ii) 12, 19, 20 and 21 illustrate methods by which the compounds of the first aspect of the present invention may be prepared.

FIG. 1 illustrates methods by which compounds 1-5, 10-12 and intermediates 19a-h, 20a-h, 21-24 can be prepared. Compounds 29 to 34 are prepared in an analogous manner. Further details are provided in Example 1.

Those compounds of the present invention comprising triazole groups can also be produced by a method termed 'click-labelling', as illustrated in FIG. 2(i), FIG. 12, and FIG. 19, and described in Examples 1 and 3. Such a method can be used to make compounds 11, 35 and 36, for example. For the manufacture of the compounds of the first aspect of the present invention, unlabelled compounds would of course be used in place of the radiolabelled compounds disclosed in these examples. For example, in the scheme illustrated in FIG. 2(i) and described in Example 3, 2-fluoroethylazide (compound 27) is used in place of 2-[$^{18}F$]fluoroethylazide (compound [$^{18}F$]27).

Cycloaddition to give substituted triazoles can also be effected in reverse (in a method termed 'reverse click-labelling'), by reaction of an isatin, functionalized at the N-1 position, with a terminal azide and a prosthetic group comprising a terminal alkyne. Such a method can be used to make compounds 6, 7, 8 and 9, for example. A pertinent example of this methodology, which also includes methods for the synthesis of the intermediate $^{18}$F-labelled terminal alkyne(s), is shown in FIG. 2(ii) and described in Example 1, and in Marik, J and Sutcliffe, J. L.[26], Sirion, U et al[27] and Li, Z. et al[28], which are incorporated herein by reference.

The twelfth aspect of the present invention provides methods of synthesizing compounds of the second aspect of the present invention. The compounds of the second aspect of the present invention may be prepared in any suitable manner. The schemes described in Examples 1 and 3 and illustrated in FIGS. 1, 2(i), 2(ii) and 12 illustrate methods by which the compounds of the second aspect of the present invention may be prepared, wherein labeled intermediate compounds are used.

The schemes described in Example 1 and illustrated in FIG. 1 can be used to prepare the compounds of the second aspect of the present invention, wherein one or more of the precursor molecules or intermediate compounds, for example compounds 19a-h, 20a-h and/or 21-25, comprise a labeled R or R' group. Such method can be used to produce labeled forms of compounds 1-5, 10-12 and 29 to 34, for example.

The schemes illustrated in FIG. 2(i), FIG. 12, FIG. 19 and described in Example 1 and Example 3 illustrate the 'click-labelling' methods by which particular compounds of the second aspect of the present invention may be prepared, including [18F]11, [11C]35 and [11C]36.

The 'reverse click-labelling' method illustrated in FIG. 2(ii) and described in Example 1 can also be used to make certain compounds according to the second aspect of the present invention, such as labeled forms of compounds 6, 7, 8 and 9. In this case, one or more labelled precursor compounds are used. For example, in the scheme illustrated in FIG. 2(ii) and described in Example 1, 3-[18F]fluoroprop-1-yne (compound [18F]28) is used in place of 3-fluoroprop-1-yne (compound 28).

However, the 'click-labelling' method described in Example 3 and illustrated in FIG. 19 suffers from the disadvantage that a stable impurity is produced, which reduces the specific activity of the isatin derivative product. As described in Example 10 and illustrated in FIGS. 20 and 21, this disadvantage can be overcome by synthesizing the isatin derivative, for example [18F]11, using a protected precursor such as those shown in the general formulae 38 and 43, wherein n=0, 1, 2, 3, 4, 5 or 6 (i.e. n=0-6) and wherein x=a leaving group, for example mesylate, tosylate, nosylate or other sulfonate ester or halide.

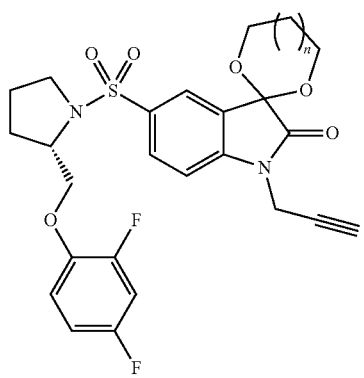

38

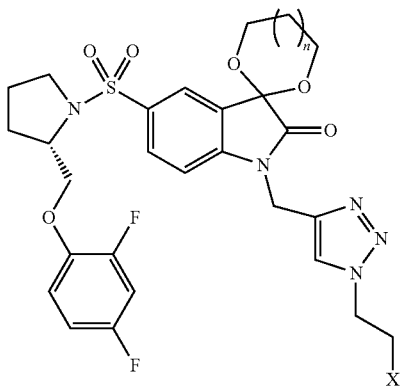

43

A particularly preferred protected alkyne precursor is (S)-1-{[1'-[1-(2-Propynyl)]-(1'2'-dihydro-2'-oxospiro(1,3-dioxane-2,3'-[3H]indol)-5'-sulfonyl}-2-(2,4-difluorophenoxymethyl)-pyrrolidine (compound 39). The use of such a protected alkyne precursor prevents undesirable side reactions at the C-3 position.

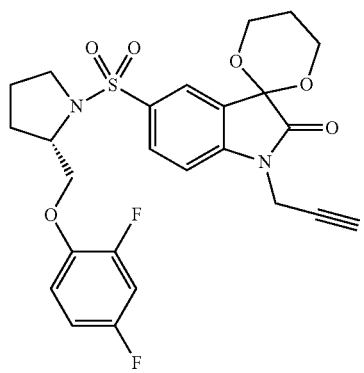

39

In addition to these methods the compounds according to the second aspect of the present invention could be radiolabeled by, for example, halo-demetallation of an appropriate tin precursor, chelation with a desired metal, preferably with a suitable ligand attached to the isatin, substitution with [18F] fluorine in the presence of a suitable aryl or alkyl leaving group.

FIGURES

FIG. 1 is a schematic representation of the synthesis of target compounds. The reagents and conditions are as follows: (a) phenol/fluoro-substituted phenol/4-tetrahydropyran, NaH, DMF, 80° C., 17 h; (b) 4(3H)-pyrimidone, PPh$_3$, DIAD, DCM, rt, 48 h; (c) propargyl bromide, KOH, DMF, rt, 18 h; (d) TFA, DCM, 0° C., 1 h; (e) 5-chlorosulfonylisatin, TEA, THF/DCM, rt, 19 h; (f) 4-fluorobenzyl bromide, K$_2$CO$_3$, DMF, rt, 2 h; (g) propargyl bromide, K$_2$CO$_3$, DMF, rt, 2 h; (h) 2-fluoroethyl azide, CuSO$_4$, L-ascorbic acid, DMF, rt, 2 h.

FIG. 2(i) is a schematic representation of the synthesis of compound [18F]11 by reaction of (S)-1-(2-Propynyl)-5-(2-(2, 4-difluorophenoxymethyl)-pyrrolidine-1-sulfonyl)isatin (compound 25) with [18F]fluoroethylazide (compound 27). Compound 26 is 2-(toluene-4-sulfonyl)ethyl azide. The reagents are as follows: (a) [$^{18}$F]KF, Kryptofix[2,2,2], acetonitrile; (b) CuSO$_4$, sodium ascorbate, phosphate buffer pH 6.0, compound 25.

FIG. 2(ii) is a schematic representation the synthesis of compound 6 ((S)-1-[4-(2-fluoroethyl)-1H-[1,2,3]-triazol-1-yl]methyl-5-(2-(2,4-difluorophenoxymethyl)-pyrrolidine-1-sulfonyl)isatin), by reaction of (S)-1-(azidomethyl)-5-(2-(2,4-difluorophenoxymethyl)-pyrrolidine-1-sulfonyl)isatin] (compound 37) with (3-fluoroprop-1-yne) (compound 28). The reagents are as follows: (a) CuSO$_4$, L-ascorbic acid, DMF.

FIG. 3 is a preparative HPLC trace of reaction mixture containing [$^{18}$F]11 (left) and analytical peak separation (right). Top: radioactivity channel; Bottom: UV channel at 254 nm.

FIG. 4 shows the biodistribution of [$^{18}$F]11 in RIF-1 tumor-bearing mice at 2, 10, 30 and 60 minutes. Data are mean±SEM; n=3-6 mice per timepoint.

FIG. 5 shows the in vivo metabolism of [$^{18}$F]11 assessed in plasma by radio-HPLC. Top left: [$^{18}$F]11 standard; top right: 2 mins plasma; bottom left: 15 mins plasma; bottom right: 60 mins plasma FIG. 6 shows the in vivo metabolism of [$^{18}$F]11 assessed in liver and urine by radio-HPLC. Top row: liver extracts; bottom row: urine extracts; left to right: 2, 15 and 60 minutes respectively.

FIG. 7 shows the biodistribution of [$^{125}$I] labelled (S)-1-(4-iodobenzyl)-5-(2-phenoxymethyl-pyrrolidine-1-sulfonyl)isatin (denoted compound [$^{125}$I]14 herein) at 2, 10, 30 and 60 minutes. Data are mean±SEM; n=3 mice per timepoint.

FIG. 8 shows the in vitro metabolism of known compounds (S)-1-(4-iodobenzyl)-5-(2-phenoxymethyl-pyrrolidine-1-sulfonyl)isatin (compound 14), (S)-1-(4-fluorobenzyl)-5-(2-phenoxymethyl-pyrrolidine-1-sulfonyl)isatin (compound 15) and 1-(4-fluorobenzyl)-5-(pyrrolidine-1-sulfonyl)isatin (compound 16) assessed in mouse liver S9 fractions by HPLC. Top row, from left to right: compounds 14, 15 and 16 at time zero; bottom row, from left to right: compounds 14, 15 and 16 after incubation for 60 minutes.

FIG. 9 shows [$^{18}$F]11 cellular uptake for 60 min in A) RIF-1 cells treated with 10 µg/mL CDDP or 10 µg/mL CHX for 24 h, B) PEO1/4 cells treated with 50 µg/mL CDDP (Cisplatin) C) LNM35 cells treated with 100 µM CDDP or 100 µM VP-16, alone or in combination. Caspase-3 assay (C right panel) is performed as described in the experimental section. * Student's t-test, p<0.005.

FIG. 10 shows whole body sagittal images of [$^{18}$F]11 distribution in CDDP-treated mice. Images were summed from 30 to 60 min after intravenous injection of approximately 100 µCi [$^{18}$F]11.

FIG. 11 shows whole body images of [$^{18}$F]11 distribution in a 38C18 xenograft bearing mouse treated with 100 mg/kg Cyclophosphamide. Images from left to right are axial, coronal and sagittal, taken 24 hours after intravenous injection of approximately 100 µCi [$^{18}$F]11.

FIG. 12 is a schematic representation of the synthesis of compounds 35 (top row) and 36 (bottom row) respectively.

FIG. 13 shows the uptake profile of [$^{18}$F]11 in RIF-1 cells treated with vehicle or CDDP. Data are expressed as decay-corrected counts per min averaged per milligram of total cellular protein. Data are mean±SEM, done in triplicate.

FIG. 14 shows the uptake of [$^{18}$F]11 in RIF-1 tumor treated with vehicle (50% DMSO) or CDDP (10 mg/kg single dose). The [$^{18}$F]-derived radioactivity levels at 60 min post radiotracer injection were analysed and expressed as a ratio to that of blood. Data are mean±SEM and n=8 mice per group.

Figure 19:
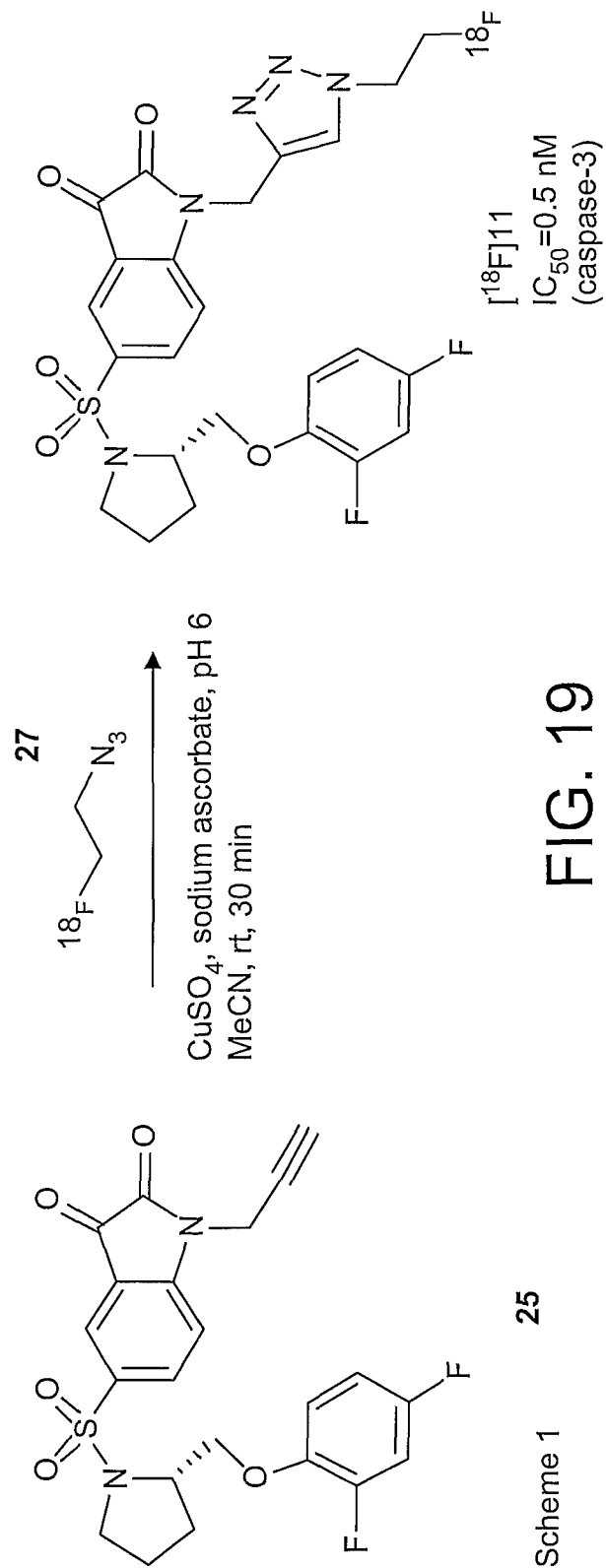

FIG. 19 a second schematic representation of the synthesis of compound [$^{18}$F]11 by reaction of (S)-1-(2-Propynyl)-5-(2-(2,4-difluorophenoxymethyl)-pyrrolidine-1-sulfonyl)isatin (compound 25) with [$^{18}$F]fluoroethylazide (compound 27).

Figure 20:
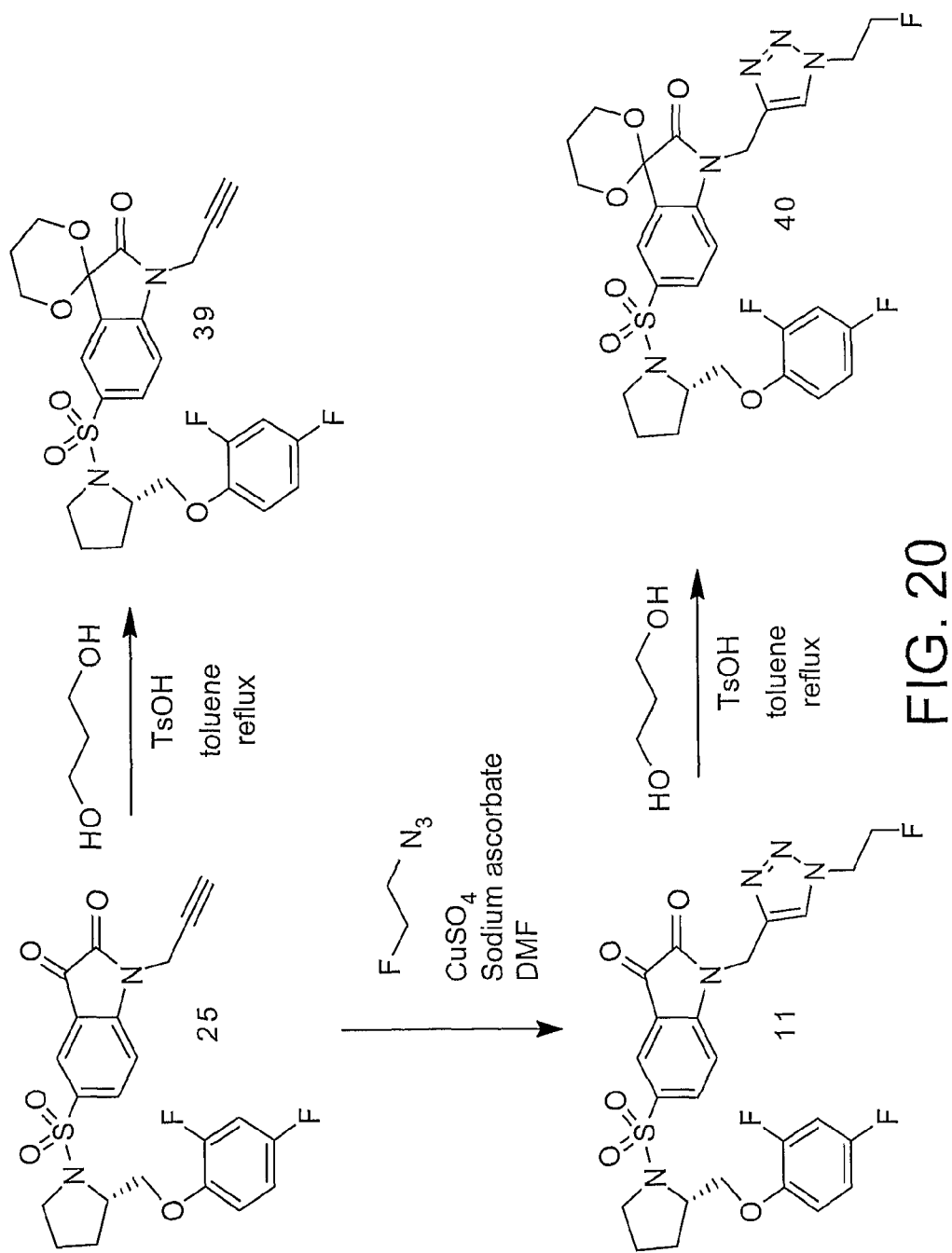

FIG. 20 is a general reaction scheme for the synthesis of a protected alkyne precursor (S)-1-{[1'-[1-(2-Propynyl)]-(1'2'-dihydro-2'-oxospiro(1,3-dioxane-2,3'-[3H]indol)-5'-sulfonyl}-2-(2,4-difluorophenoxymethyl)-pyrrolidine (compound 39) and a protected trizole (S)-1-{[1'-[1-(2-Fluoroethyl)-1H-[1,2,3]-triazol-4-yl]-(1'2'-dihydro-2'-oxospiro(1,3-dioxane-2,3'-[3H]indol)-5'-sulfonyl}-2-(2,4-difluorophenoxymethyl)-pyrrolidine (compound 40).

Figure 21:
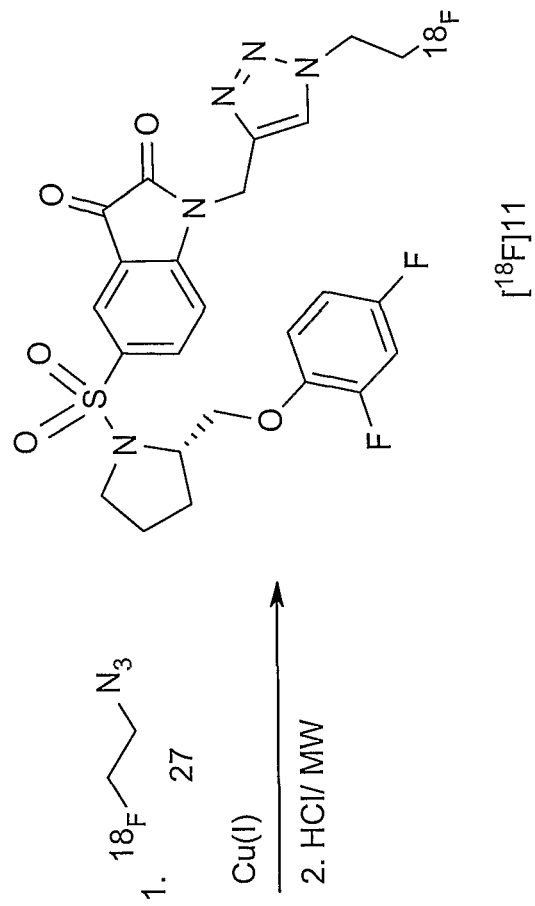
Figure 21:
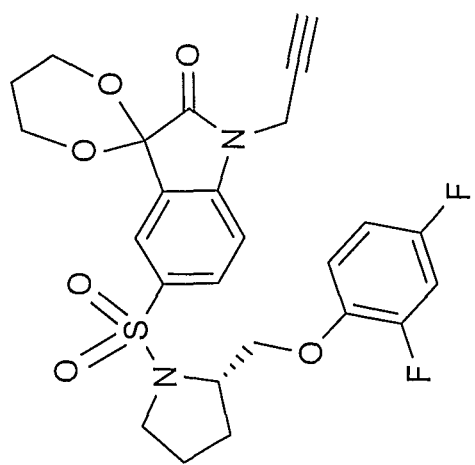

FIG. 21 is a schematic representation of a typical radiochemistry reaction for the production of [$^{18}$F]11 from the protected alkyne precursor (S)-1-{[1'41-(2-Propynyl)]-(1'2'-dihydro-2'-oxospiro(1,3-dioxane-2,3'-[3H]indol)-5'-sulfonyl}-2-(2,4-difluorophenoxymethyl)-pyrrolidine (compound 39)

Figure 22:
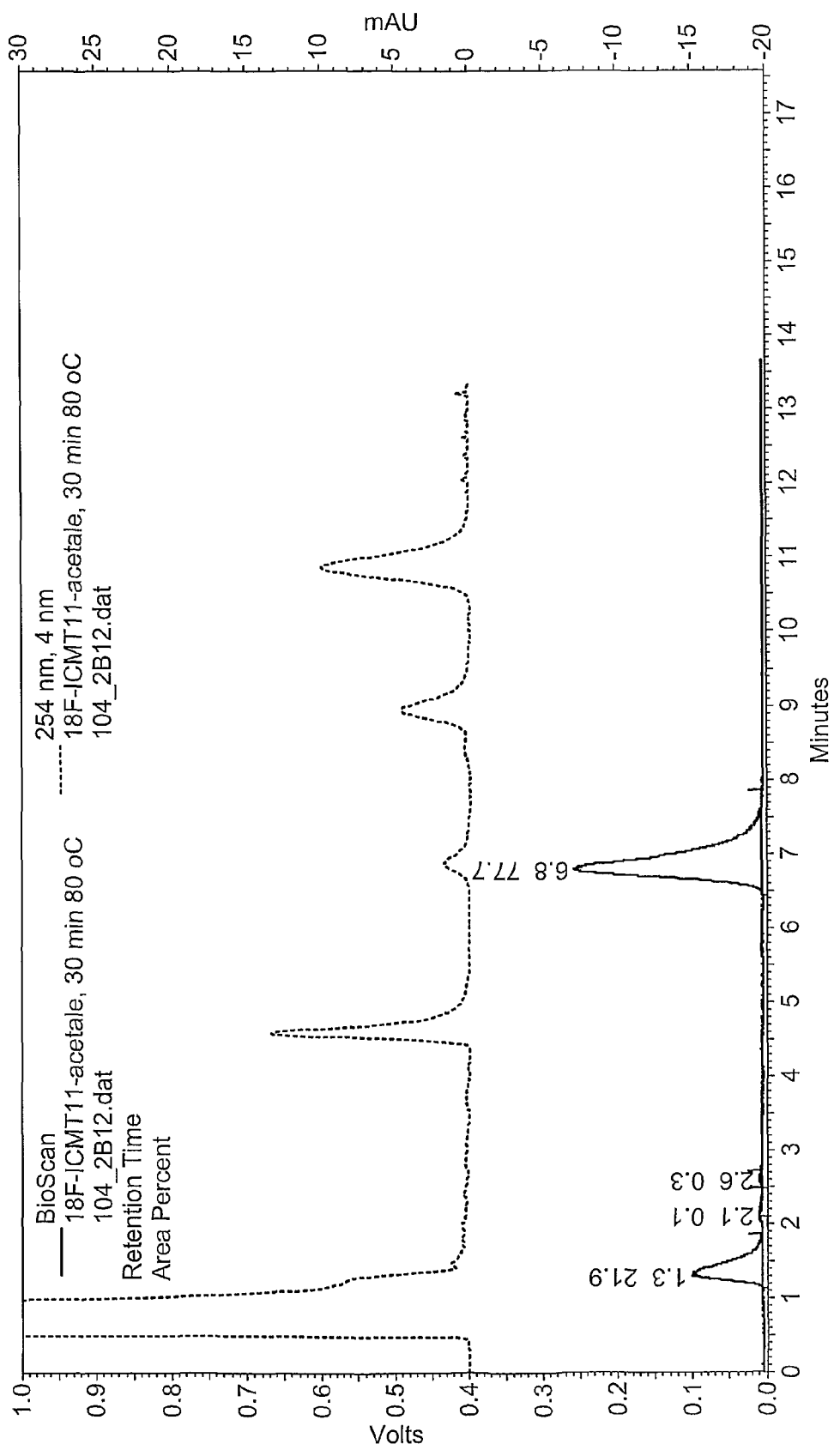

FIG. 22 shows the HPLC analysis of the labelling mixture prior to deprotection. Red: radioactivity channel, Blue: UV channel at 254 nm. Remaining [$^{18}$F]-fluoroethylazide: 1.3 min, labelled isatin acetale: 6.8 min.

Figure 23:
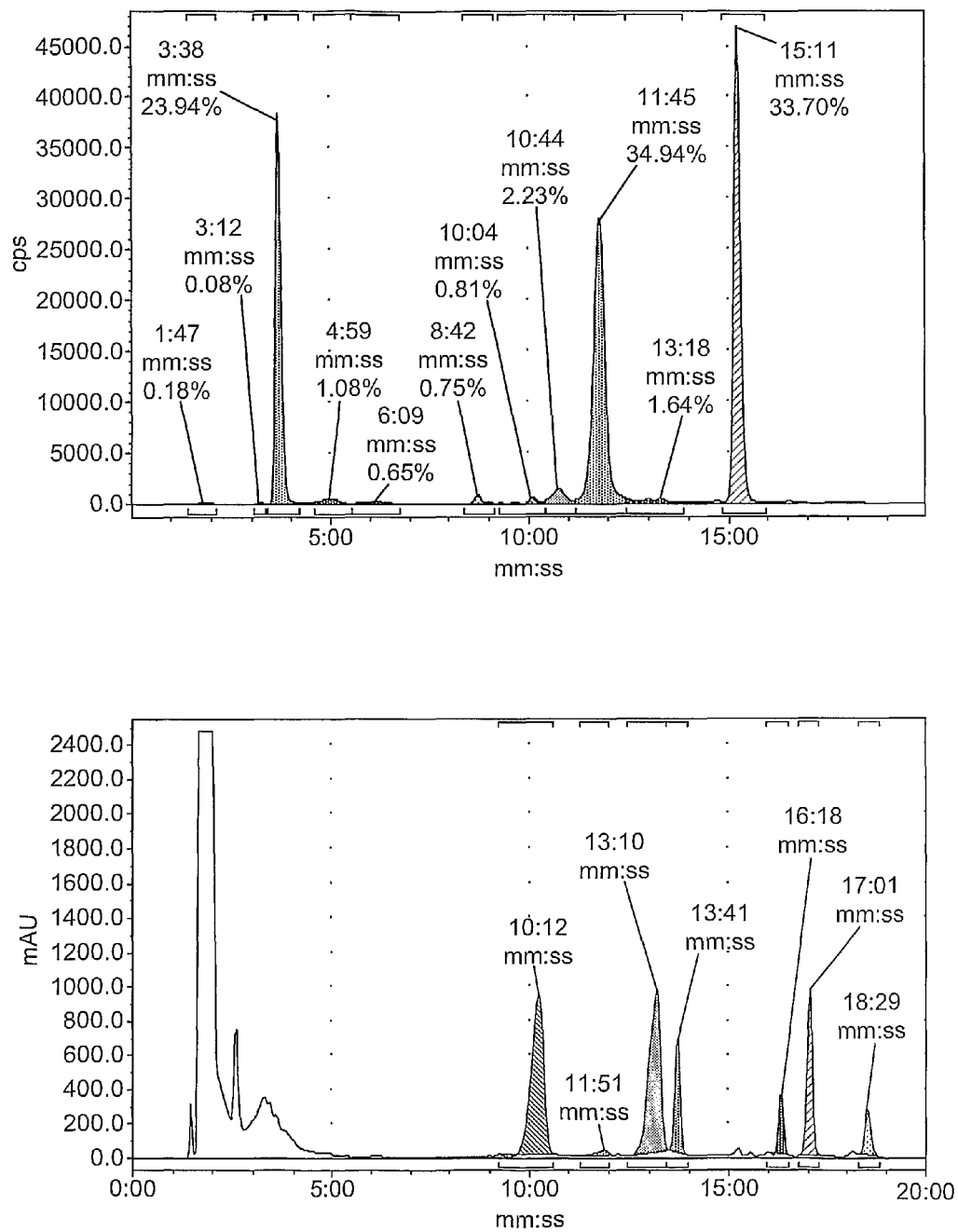

FIG. 23 shows the preparative HPLC of [$^{18}$F]11. Top: Radioactivity channel. The peak at 11:45 min corresponds to [$^{18}$F]11. Bottom: UV channel, 254 nm. The signal at 11:51 min is the stable impurity.

Figure 24:
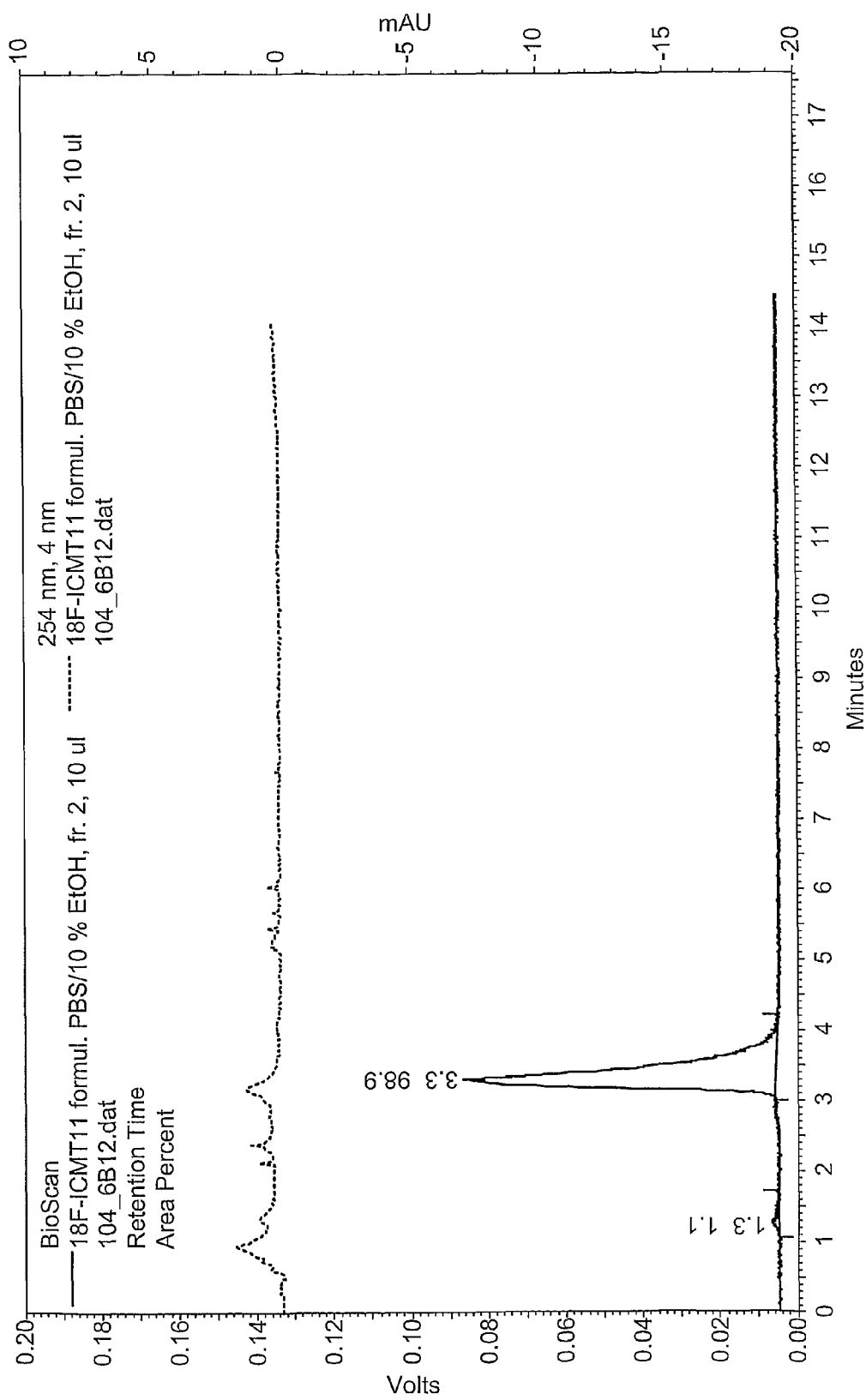

FIG. 24 shows the Analytical HPLC of formulated [$^{18}$F]11. Top: UV channel at 254 nm, bottom: radioactivity signal showing [$^{18}$F]11 at 3.3 min.

Figure 25:
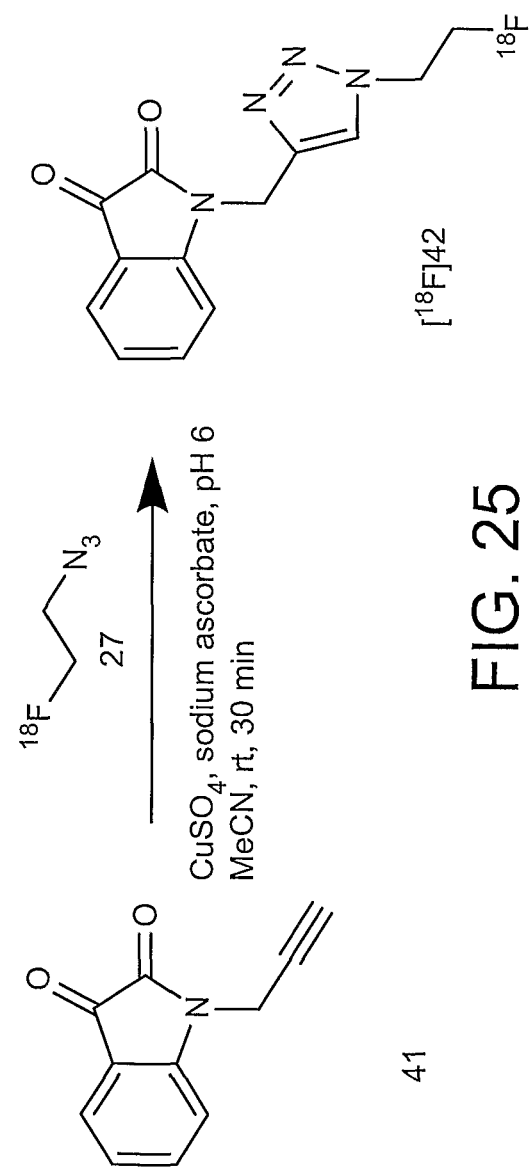

FIG. 25 is a schematic representation of the synthesis of the weak isatin caspase-3 inhibitor N-[1-(2-Fluoroethyl)-1H-[1,2,3]-triazol-4-yl]isatin (compound 42) from N-(2-Propynyl)isatin (compound 41).

Figure 26:
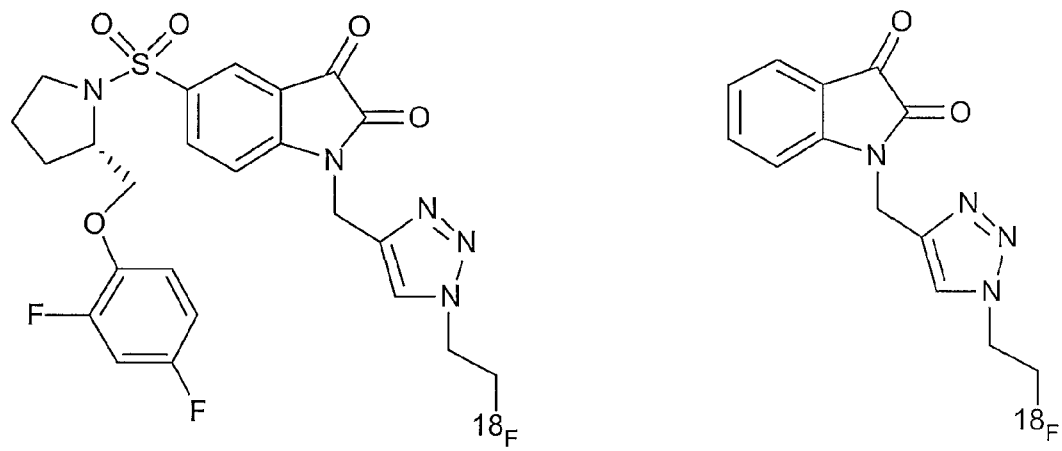
Figure 26:
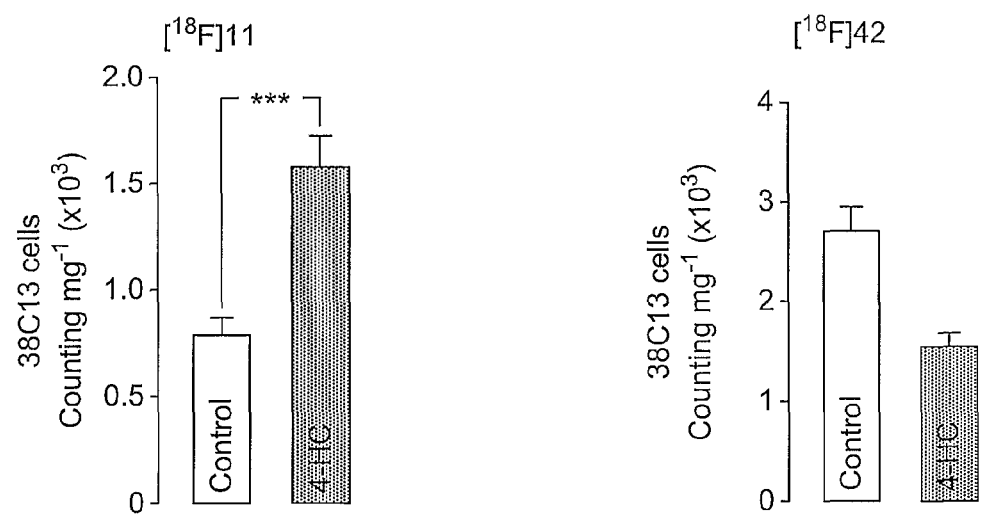

FIG. 26 shows [$^{18}$F]11 and [$^{18}$F]42 binding in cancer cells undergoing treatment-induced apoptosis. (left panel). Chemical structure and [$^{18}$F]11 binding in 38C13 lymphoma cells treated with 4-hydroperoxycyclophosphamide 4-HC (4-HC; 1 µg/mL; 24 h) to induce apoptosis. For all treated and control samples, radioactivity data were expressed as decay-corrected counts per milligram of total cellular protein. (right panel) The effect of 4-HC on the binding of the low affinity probe, [$^{18}$F]42, in 38C13 lymphoma cells. Data are mean±s.e.m.

EXAMPLES

Example 1

Synthesis of Compounds

Figure 1:
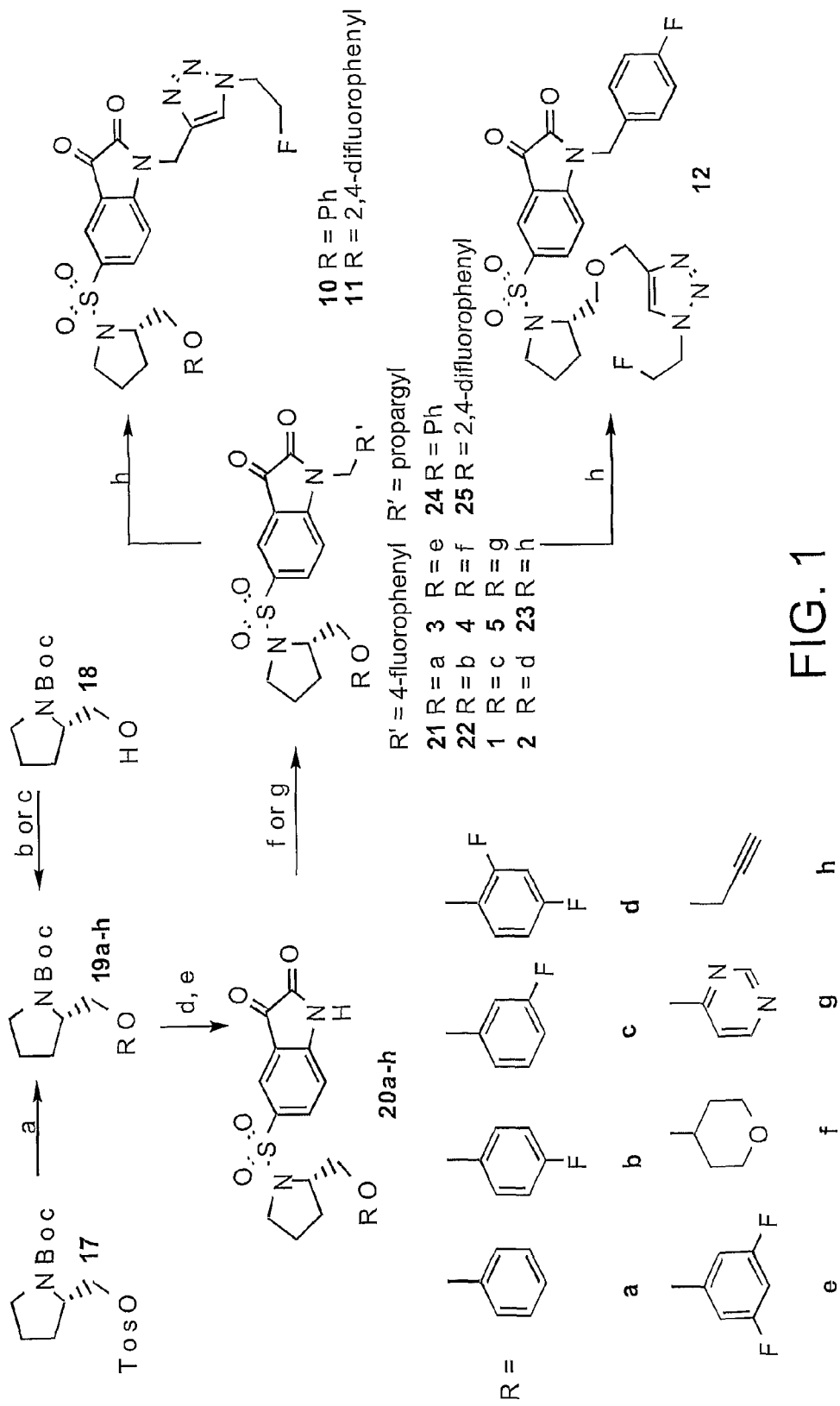

A library of target compounds was created, using ((S)-1-(4-fluorobenzyl)-5-(2-phenoxymethyl-pyrrolidine-1-sylfonyl)isatin) as the lead compound. Modifications were made to the left side ether moiety and at the N-1 position. Fluorine groups were incorporated into the left side phenyl ether group, and the tolerance of heterocycles and alkynes at this position was investigated. Tolerance to 1,2,3 triazole groups at the N-1 position was also investigated. The target compounds were synthesized as shown in FIG. 1 by condensation of functionalized pyrrolidines with 5-chlorosulfonylisatin and subsequent alkylation of the isatin nitrogen using potassium carbonate/DMF. All necessary starting materials are commercially available, or are produced as described in Lee, D. et al [8], Chu, W. et al[9] and Kopka, K. et al[13].

Reaction of commercially available phenols as well as 4-hydroxytetrahydropyran with the tosylate 17 provided the pyrrolidines 19a-f in good yield. 4(3H)-pyrimidone was coupled with the (S)-1-(tert-butoxycarbonyl)-2-pyrrolidinemethanol (compound 18) using a modification of the procedure reported by Wipf et al.[15] to provide the pyrrolidine 19g in 69% yield. O-alkylation of 18 with propargyl bromide provided the corresponding ether 19h in 67% yield. Deprotection of the BOC protected pyrrolidines 19a-h with trifluoroacetic acid followed by conjugation with 5-chlorosulfonylisatin provided the sulfonamides 20a-h in moderate to good yields. Subsequent treatment of 20b-h with 4-fluorobenzyl bromide under basic conditions provided the novel compounds 1 to 5 and intermediate compounds 22 and 23, whereas treatment of 20a and 20d with propargyl bromide provided the intermediate alkynes 24 and 25, respectively. The novel triazoles 10-12 were prepared by copper catalyzed cycloaddition of 2-fluoroethylazide with the respective alkyne precursors 23, 24 and 25. Somewhat surprisingly, the isatin scaffold decomposed on heating at 90° C. in the presence of the copper sulfate and ascorbic acid, resulting in poor yields of the novel triazoles 10-12. The issue was partly resolved by increasing the copper sulfate concentration from 5% to 50% relative to the alkyne precursor, carrying out the reaction at ambient temperature and reducing the reaction time to 1 h, which provided the triazoles 10-12 in yields of 48-57%.

Chemistry Reagents and solvents were purchased from Sigma-Aldrich (Gillingham, United Kingdom) and used without further purification. Potassium hydroxide and potassium carbonate were stored in a vacuum dessicator over phosphorus pentoxide. All reactions were carried out under argon unless otherwise stated. Petroleum ether refers to the fraction that is distilled between 40° C. and 60° C. Automated flash chromatography was performed on a CombiFlash Companion machine (Companion Presearch Ltd.), using RediSep 4 g or 12 g normal phase silica cartridges (flow rate 12 mL/min or 26 mL/min) Manual flash chromatography was carried out using a Davisil neutral silica (60 Å, 60-200 micron, Fisher Scientific, Loughborough, UK), solvent mixtures are quoted as volume/volume. $^1$H NMR Spectra were obtained on a Bruker Avance 600 MHz NMR machine and spectra are referenced to residual solvent. Coupling constants (J) are given in Hertz (Hz). GC-MS Data was acquired under electron ionization using an Agilent 6890N system. Mass spectra were obtained in positive electrospray ionisation mode on a WatersMicromass LCT Premier machine. Melting points were determined in capillary tubes on a Stuart Scientific SMP1 melting point apparatus and are uncorrected. Solvent mixtures for thin layer chromatography (TLC) are quoted as volume/volume and samples were developed on aluminium backed neutral silica plates (0.2 mm thickness) (Fluka, Seelze, Germany). Purity analysis for compounds 1-5, 10-16, 20b-h and 22-25 was evaluated by analytical HPLC; compounds 19b-h were analyzed by GC-MS. Purity of all compounds was greater than 95%. [$^{18}$F]Fluoride was produced by a cyclotron (GE PETrace) using the $^{18}$O(p,n)$^{18}$F nuclear reaction with 16.4 MeV proton irradiation of an enriched [$^{18}$O] H$_2$O target.

HPLC methods a) Purity analysis of non-radioactive compounds was carried out on an Agilent 1100 series system with Laura 3 software (Lablogic, Sheffield, UK) with a Phenomenex Luna 50×4.6 mm (3 μm) HPLC column attached and a mobile phase of 0.1 M ammonium formate and methanol/acetonitrile (1.8:1 v/v), gradient (50% organic for 1 min; 50→90% organic in 14 min; 90% organic for 4 min; 90→50% organic phase for 4 min) flow rate 1 mL/min and wavelength 254 nm.

b) Preparative radio-HPLC was carried out on a Beckman System Gold equipped with a Bioscan Flowcount FC-3400 PIN diode detector (Lablogic) and a linear UV-200 detector (wavelength 254 nm). A Phenomenex Onyx $C_{18}$ 100×10 mm HPLC column and a mobile phase of water and methanol/acetonitrile (1.8:1 v/v), gradient 45→90% organic in 20 min and flow rate 3 mL/min.

c) Analytical radio-HPLC was carried out as above but using a Bioscan Flowcount FC3200 sodium iodide/PMT gamma detector (Lablogic) and a Phenomenex Luna 50×4.6 mm (3 μm) column with a mobile phase of water and methanol/acetonitrile (1.8:1 v/v), gradient 60→90% organic in 20 min, flow rate 1 mL/min.

Manufacture of Known Compounds

The following compounds were synthesized according to established literature procedures and $^1$H NMR spectral data was consistent with reported values: (S)-1-benzyl-5-(2-phenoxymethyl-pyrrolidine-1-sulfonyl)isatin (compound 13), (S)-1-(4-iodobenzyl)-5-(2-phenoxymethyl-pyrrolidine-1-sulfonyl)isatin (compound 14) and (S)-1-(4-fluorobenzyl)-5-(2-phenoxymethyl-pyrrolidine-1-sulfonyl)isatin (compound 15).

1-(4-Fluorobenzyl)-5-(pyrrolidine-1-sulfonyl)isatin (compound 16)

To an ice-cold, stirred solution of 5-pyrrolidine-1-sulfonylisatin[8] (0.14 g, 0.5 mmol) in dry DMF (8 mL) was added sodium hydride (40 mg, 1 mmol). After 30 min 4-fluorobenzyl bromide (0.38 g, 2 mmol) was added and the mixture allowed warm to room temperature. After 19 h the orange solution was poured onto 10% aq. NH$_4$Cl (25 mL) and extracted with DCM (3×15 mL). Following concentration in vacuo the residue taken up in diethyl ether (10 mL) and washed with water (3×10 mL) and dried over Na$_2$SO$_4$. Chromatography (diethyl ether/hexanes) afforded the title compound as an orange gum (83 mg, 43%). HRMS (ESI)=389.0988 (M+H)$^+$. Calcd. for $C_{19}H_{18}FN_2O_4S$ 389.0971. $^1$H NMR (600 MHz, CDCl$_3$) δ 8.05 (d, J=1.5 Hz, 1H), 7.99 (dd, J=8.4 Hz, J=1.5 Hz, 1H), 7.35-7.32 (m, 2H), 7.09-7.06 (m, 2H), 6.91 (d, J=8.4 Hz, 1H), 4.94 (s, 2H), 3.25-3.23 (4H, m), 1.84-1.79 (4H, m). TLC (UV$_{254}$) R$_f$=0.63 (4:1 ethyl acetate/hexanes). HPLC t$_R$=6.83 min Manufacture of Novel Compounds and their Intermediates (S)-tert-Butyl 2-(4-fluorophenoxymethyl)pyrrolidine-1-carboxylate (compound 19b)

To a stirred solution of 4-fluorophenol (0.27 g, 2.4 mmol) in dry DMF (10 mL) was added sodium hydride (60% w/w in mineral oil) (0.11 g, 2.8 mmol). After 30 min ((S)-1-(tert-butoxycarbonyl)pyrrolidin-2-yl)toluene-4-sulfonate[8] (compound) 15 (0.71 g, 2.0 mmol) in dry DMF (5 mL) was then added and the mixture heated to 80° C. for 17 h. The reaction was allowed to cool to room temperature and poured over 1M NaOH (25 mL) and extracted with DCM (3×15 mL). The combined organic fractions were reduced under vacuum and diethyl ether (20 mL) added, then washed with 1M NaOH (1×20 mL), water (1×20 mL) then brine (1×20 mL) and dried over $Na_2SO_4$. Chromatography (hexanes/ethyl acetate) gave the product as a colorless oil (0.36 g, 61%). HRMS (ESI)=296.1654 (M+H)$^+$. Calcd. for $C_{16}H_{23}FNO_3$ 296.1656. $^1$H NMR (600 MHz, CDCl$_3$) δ 6.97-6.93 (m, 2H), 6.88-6.84 (m, 2H), 4.18-4.03 (m, 2H), 3.94-3.73 (m, 1H), 3.46-3.32 (m, 2H), 2.07-1.81 (m, 4H), 1.47 (s, 9H). TLC UV$_{254}$) R$_f$=0.51 (2:1 hexanes/ethyl acetate).

(S)-tert-Butyl 2-(3-fluorophenoxymethyl)pyrrolidine-1-carboxylate (compound 19c)

19c was prepared according to the procedure for 19b except using 3-fluorophenol. Chromatography (hexanes/ethyl acetate) afforded the title compound as a colorless oil (0.32 g, 54%). HRMS (ESI)=296.1657 (M+H)$^+$. Calcd. for $C_{16}H_{23}FNO_3$ 296.1656 $^1$H NMR (600 MHz, CDCl$_3$) δ 7.20-7.15 (m, 1H), 6.73-6.69 (m, 1H), 6.65-6.59 (m, 2H), 4.18-4.03 (m, 2H), 3.97-3.74 (m, 1H), 3.48-3.29 (m, 2H), 2.05-1.79 (m, 4H), 1.48 (s, 9H). TLC (UV$_{254}$) R$_f$=0.40 (3:1 hexanes/ethyl acetate).

(S)-tert-Butyl2-(2,4-difluorophenoxymethyl)pyrrolidine-1-carboxylate (compound 19d)

19d was prepared according to the procedure for 19b except using 2,4-difluorophenol. Chromatography (hexanes/ethyl acetate) afforded the title compound as a colorless oil (1.92 g, 58%). HRMS (ESI)=314.1560 (M+H)$^+$. Calcd. for $C_{16}H_{22}F_2NO_3$ 314.1562. $^1$H NMR (600 MHz, CDCl$_3$) δ 7.08-6.76 (m, 3H), 4.21-3.87 (m, 3H), 3.47-3.32 (m, 2H), 2.16-1.85 (m, 4H), 1.48 (s, 9H). TLC (UV$_{254}$) R$_f$=0.51 (2:1 hexanes/ethyl acetate).

(S)-tert-Butyl2-(3,5-difluorophenoxymethyl)pyrrolidine-1-carboxylate (compound 19e)

19e was prepared according to the procedure for 19b except using 3,5-difluorophenol. Chromatography (hexanes/ethyl acetate) afforded the title compound as a colorless oil (0.31 g, 53%). HRMS (ESI)=314.1563 (M+H)$^+$. Calcd. for $C_{16}H_{22}F_2NO_3$ 314.1562. $^1$H NMR (600 MHz, CDCl$_3$) δ 6.44-6.29 (m, 3H), 4.11-3.98 (m, 2H), 3.91-3.72 (m, 1H), 3.42-3.24 (m, 2H), 1.99-1.79 (m, 4H), 1.42 (s, 9H). TLC (UV$_{254}$) R$_f$=0.56 (2:1 hexanes/ethyl acetate).

(S)-tert-Butyl2-(4-tetrahydropyranyloxymethyl)pyrrolidine-1-carboxylate (compound 19l)

19f was prepared according to the procedure for 19b except using 4-hydroxytetrahydropyran. Chromatography (ethyl acetate) afforded the title compound as a colorless oil (0.14 g, 25%). HRMS (ESI)=286.2012 (M+H)$^+$. Calcd. for $C_{15}H_{28}NO_4$ 286.2013. $^1$H NMR (600 MHz, CDCl$_3$) δ 3.97-3.83 (m, 2H), 3.64-3.23 (m, 9H), 1.97-1.72 (m, 5H), 1.60-1.52 (m, 2H), 1.46 (s, 9H). TLC (I$_2$) R$_f$=0.62 (ethyl acetate).

(S)-tert-Butyl 2-(pyrimidin-4-yloxymethyl)pyrrolidine-1-carboxylate (compound 19g)

To a stirred solution of N-tert-butoxycarbonyl-L-prolinol (0.81 g, 4 mmol) 18 in dry DCM (10 mL) was added triphenylphosphine (5.24 g, 20 mmol) followed by 4(3H)-pyrimidone (0.77 g, 8 mmol). The solution was cooled in an ice bath and DIAD (3.24 g, 16 mmol) added dropwise over 10 min. After 48 h GC-MS indicated complete conversion of 18 and the reaction mixture was poured onto water (30 mL), the organic fraction collected and the aqueous phase washed with further DCM (2×20 mL). The combined organic fractions were washed with 1M NaOH (2×15 mL) then brine (1×15 mL) and dried over $Na_2SO_4$. Removal of bulk solvent yielded an orange gum, addition of hexanes/diethyl ether (1:1) resulted in formation of a precipitate of triphenylphosphine oxide, which was removed by filtration. Chromatography (ethyl acetate) afforded the desired product as a colorless oil (0.77 g, 69%). HRMS (ESI)=280.1655 (M+H)$^+$. Calcd. for $C_{14}H_{22}N_3O_3$ 280.1656. $^1$H NMR (600 MHz, CDCl$_3$) δ 8.71 (s, 1H), 8.39 (d, J=6 Hz, 1H), 6.69 (d, J=6 Hz, 1H), 4.45-3.91 (m, 3H), 3.40-3.33 (m, 2H), 2.00-1.82 (m, 4H), 1.42 (s, 9H). TLC (UV$_{254}$) R$_f$=0.49 (ethyl acetate).

(S)-tert-Butyl 2-(2-propynyloxymethyl)pyrrolidine-1-carboxylate (compound 19h)

To a stirred solution of 18 (0.40 g, 2 mmol) in dry DMF (10 mL) was added potassium hydroxide (0.56 g, 10 mmol), followed by dropwise addition of propargyl bromide (80 wt. % in toluene) (0.48 g, 4 mmol) over 5 min. After 18 h the reaction mixture was poured onto water (30 mL) and washed with DCM (3×15 mL). The combined organic fractions concentrated in vacuo and the liquid remaining taken up in diethyl ether (15 mL) and washed with water (2×10 mL), then brine (1×10 mL) and dried over $Na_2SO_4$. Chromatography (hexanes/ethyl acetate) gave the desired product as a colorless oil (0.32 g, 67%). HRMS (ESI)=240.1597 (M+H)$^+$. Calcd. for $C_{13}H_{22}NO_3$ 240.1594. $^1$H NMR (600 MHz, CDCl$_3$) δ 4.13 (s, 2H), 3.96-3.88 (m, 1H), 3.64 (dd, J=9 Hz, J=3.6 Hz, 1H), 3.49-3.22 (m, 3H), 2.40 (s, 1H), 1.94-1.78 (m, 4H), 1.46 (s, 9H). TLC (I$_2$) R$_f$=0.67 (1:1 hexanes/ethyl acetate).

(S)-5-(2-(4-Fluorophenoxymethyl)-pyrrolidine-1-sulfonyl)isatin (compound 20b)

To a stirred solution of 19b (0.15 g, 0.5 mmol) in dry DCM (4 mL) cooled in an ice bath was added TFA (0.6 mL, 10 mmol). After 1 h bulk solvent was removed in vacuo and the residue remaining taken up in dry DCM (8 mL) and cooled in an ice bath. Dry triethylamine (1.5 mL) was then added followed by 5-chlorosulfonylisatin[8] (0.16 g, 0.65 mmol) in dry THF (4 mL) and the solution was then stirred. After 19 h bulk solvent was removed in vacuo and redissolved in DCM (10 mL), washed with water (2×10 mL), then brine (1×10 mL) and dried over $Na_2SO_4$. Chromatography (hexanes/ethyl acetate) gave the desired product as an orange solid (104 mg, 51%). Mp: 205-207° C. HRMS (ESI)=405.0941 (M+H)$^+$. Calcd. for $C_{19}H_{18}FN_2O_5S$ 405.0920. $^1$H NMR (600 MHz, CDCl$_3$) δ 8.10 (s, 1H), 8.08 (dd, J=8.4 Hz, J=1.8 Hz, 1H), 8.00 (br, 1H), 7.00 (d, J=7.8 Hz, 1H), 6.99-6.95 (m, 2H), 6.83-6.81 (m, 2H), 4.17 (dd, J=9.6 Hz, J=3.6 Hz, 1H), 3.98-3.95 (m, 1H), 3.91 (dd, J=9 Hz, J=7.8 Hz, 1H), 3.54-3.50 (m, 1H), 3.24-3.19 (m, 1H), 2.10-1.99 (m, 2H), 1.87-1.77 (m, 2H). TLC (UV$_{254}$) R$_f$=0.27 (2:1 ethyl acetate/hexanes). HPLC t$_R$=7.83

(S)-5-(2-(3-Fluorophenoxymethyl)-pyrrolidine-1-sulfonyl)isatin (compound 20c)

20c was prepared according to the procedure for 20b except using 19c to give an orange solid (93 mg, 46%). Mp:

201-203° C. HRMS (ESI)=405.0933 (M+H)$^+$. Calcd. for C$_{19}$H$_{18}$FN$_2$O$_5$S 405.0920. $^1$H NMR (600 MHz, CDCl$_3$) δ 8.14 (br, 1H), 8.09-8.06 (m, 2H), 7.21 (q, J=7.2 Hz, 1H), 7.03 (d, J=7.8 Hz, 1H), 6.67-6.62 (m, 2H), 6.55 (dt, J=10.8 Hz, J=2.4 Hz, 1H), 4.17 (dd, J=9 Hz, J=3 Hz, 1H), 4.01-3.97 (m, 1H), 3.94 (dd, J=9 Hz, J=7.2 Hz, 1H), 3.54-3.50 (m, 1H), 3.27-3.25 (m, 1H), 2.08-1.96 (m, 2H), 1.88-1.77 (m, 2H). TLC (UV$_{254}$) R$_f$=0.36 (2:1 ethyl acetate/hexanes). HPLC t$_R$=8.27 min.

(S)-5-(2-(2,4-Difluorophenoxymethyl)-pyrrolidine-1-sulfonyl)isatin (compound 20d)

20d was prepared according to the procedure for 20b except using 19d to give an orange solid (0.86 g, 34%). Mp: 185-187° C. HRMS (ESI)=423.0834 (M+H)$^+$. Calcd. for C$_{19}$H$_{17}$F$_2$N$_2$O$_5$S 423.0826. $^1$H NMR (600 MHz, CDCl$_3$) δ 8.08-8.06 (m, 2H), 7.97 (br, 1H), 7.03 (d, J=9 Hz, 1H), 6.97-6.92 (m, 1H), 6.87-6.77 (m, 2H), 4.21 (dd, J=8.4 Hz, J=2.4 Hz, 1H), 4.03-3.97 (m, 2H), 3.56-3.52 (m, 1H), 3.23-3.17 (m, 1H), 2.11-2.01 (m, 2H), 1.88-1.75 (m, 2H). TLC (UV$_{254}$) R$_f$=0.46 (2:1 ethyl acetate/hexanes). HPLC t$_R$=8.12 min.

(S)-5-(2-(3,5-Difluorophenoxymethyl)-pyrrolidine-1-sulfonyl)isatin (compound 20e)

20e was prepared according to the procedure for 20b except using 19e to give an orange solid (112 mg, 53%). Mp: 196-198° C. HRMS (ESI)=423.0834 (M+H)$^+$. Calcd. for C$_{19}$H$_{17}$F$_2$N$_2$O$_5$S 423.0826. $^1$H NMR (600 MHz, CDCl$_3$) δ 8.10-8.06 (m, 2H), 8.04 (br, 1H), 7.05 (d, J=8.4 Hz), 6.45-6.38 (m, 3H), 4.18 (dd, J=8.4 Hz, J=-2.4 Hz, 1H), 3.99-3.92 (m, 2H), 3.56-3.49 (m, 1H), 3.24-3.17 (m, 1H), 2.04-1.92 (m, 2H), 1.86-1.77 (m, 2H). TLC (UV$_{254}$) R$_f$=0.36 (2:1 ethyl acetate/hexanes). HPLC t$_R$=9.18 min.

(S)-5-(2-(Tetrahydro-2H-pyran-4-yloxymethyl)-pyrolidine-1-sulfonyl)isatin (compound 20f)

20f was prepared according to the procedure for 20b except using 19f to give an orange gum (63 mg, 32%). HRMS (ESI)=395.1282 (M+H)$^+$. Calcd. for C$_{18}$H$_{23}$N$_2$O$_6$S 395.1277. $^1$H NMR (600 MHz, CDCl$_3$) δ 8.17 (br, 1H), 8.10-8.08 (m, 2H), 7.07 (d, J=8.4 Hz, 1H), 3.94-3.90 (m, 2H), 3.77-3.73 (m, 1H), 3.70 (dd, J=9.6 Hz, J=3 Hz, 1H), 3.56-3.51 (septet, J=4.2 Hz, 1H), 3.48-3.44 (m, 3H), 3.13-3.11 (m, 1H), 2.05-1.87 (m, 4H), 1.72-1.64 (m, 2H), 1.60-1.52 (m, 2H). TLC (UV$_{254}$) R$_f$=0.26 (4:1 ethyl acetate/hexanes). HPLC t$_R$=2.65 min.

(S)-5-(2-(Pyrimidin-4-yloxymethyl)-pyrrolidine-1-sulfonyl)isatin (compound 20g)

20g was prepared according to the procedure for 20b except using 19g. Chromatography (ethyl acetate) gave an orange gum (51 mg, 27%). HRMS (ESI)=389.025 (M+H)$^+$. Calcd. for C$_{17}$H$_{17}$N$_4$O$_5$S 389.020. $^1$H NMR (600 MHz, CDCl$_3$) δ 8.79 (s, 1H), 8.45 (d, J=5.4 Hz, 1H), 8.12 (d, J=1.8 Hz, 1H), 8.09 (dd, J=8.4 Hz, J=1.8 Hz, 1H), 7.95 (br, 1H), 7.03 (d, J=8.4 Hz, 1H), 6.72 (d, J=5.4 Hz, 1H), 4.57 (dd, J=10.8 Hz, J=4.8 Hz, 1H), 4.39 (dd, J=10.8 Hz, J=7.2 Hz, 1H), 4.08-4.04 (m, 1H), 3.53-3.46 (m, 1H), 3.27-3.22 (m, 1H), 2.01-1.93 (m, 2H), 1.84-1.74 (m, 2H). TLC (UV$_{254}$) R$_f$=0.49 (9:1 ethyl acetate/methanol). HPLC t$_R$=1.90 min.

(S)-5-(2-(2-Propynyloxymethyl)-pyrrolidine-1-sulfonyl)isatin (compound 20h)

20h was prepared according to the procedure for 20b except using 19h to give an orange gum (92 mg, 53%). HRMS (ESI)=349.0867 (M+H)$^+$. Calcd. for C$_{16}$H$_{17}$N$_2$O$_5$S 349.067. $^1$H NMR (600 MHz, CDCl$_3$) δ 8.10-8.07 (m, 2H), 7.84 (br, 1H), 7.04 (d, J=8.4 Hz, 1H), 4.16 (s, 2H), 3.83-3.79 (m, 1H), 3.72 (dd, J=9.6 Hz, J=3.6 Hz, 1H), 3.54 (dd, J=9.6 Hz, J=3.6 Hz, 1H), 3.45-3.43 (m, 1H), 3.19-3.15 (m, 1H), 2.46 (t, J=2.4 Hz, 1H), 1.96-1.89 (m, 2H), 1.74-1.67 (m, 2H). TLC (H$_{254}$) R$_f$=0.28 (2:1 ethyl acetate/hexanes). HPLC t$_R$=2.93 min.

(S)-1-(4-Fluorobenzyl)-5-(2-(4-fluorophenoxymethyl)-pyrrolidine-1-sulfonyl)isatin (compound 22)

To a stirred solution of 20b (40 mg, 0.1 mmol) in dry DMF (3 mL) was added potassium carbonate (21 mg, 0.15 mmol) followed by 4-fluorobenzyl bromide (76 mg, 0.4 mmol). After 2 h TLC indicated complete conversion of 20b and the solution was poured onto 10% aq. NH$_4$Cl (10 mL) and extracted with DCM (3×10 mL). Combined organic fractions concentrated in vacuo and taken up in diethyl ether (10 mL), washed with water (2×10 mL), then brine (1×10 mL) and dried over Na$_2$SO$_4$. Chromatography (hexanes/ethyl acetate) gave the title compound as an orange gum (34 mg, 66%). HRMS (ESI)=513.1306 (M+H)$^+$. Calcd. for C$_{26}$H$_{23}$F$_2$N$_2$O$_5$S 513.1296. $^1$H NMR (600 MHz, CDCl$_3$) δ 8.04 (d, J=1.8 Hz, 1H), 7.97 (dd, J=8.4 Hz, J=1.8 Hz, 1H), 7.33-7.30 (m, 2H), 7.09-7.05 (m, 2H), 6.96-6.92 (m, 2H), 6.86 (d, J=8.4 Hz, 1H), 6.81-6.77 (m, 2H), 4.92 (d, J=15.6 Hz, 1H), 4.91 (d, J=15.6 Hz, 1H), 4.14 (dd, J=9.6 Hz, J=3.6 Hz, 1H), 3.95-3.92 (m, 1H), 3.88 (dd, J=9.6 Hz, J=7.2 Hz, 1H), 3.51-3.47 (m, 1H), 3.20-3.15 (m, 1H), 2.06-1.93 (m, 2H), 1.83-1.73 (m, 2H). TLC (UV$_{254}$) R$_f$=0.61 (2:1 ethyl acetate/hexanes). HPLC t$_R$=12.25 min.

(S)-1-(4-Fluorobenzyl)-5-(2-(3-fluorophenoxymethyl)-pyrrolidine-1-sulfonyl)isatin (compound 1)

1 was prepared according to the procedure for 22 except using 20c to give an orange gum (31 mg, 61%). HRMS (ESI)=513.1298 (M+H)$^+$. Calcd. for C$_{26}$H$_{23}$F$_2$N$_2$O$_5$S 513.1296. $^1$H NMR (600 MHz, CDCl$_3$) δ 8.02 (d, J=1.8 Hz, 1H), 7.98 (dd, J=8.4 Hz, J=1.8 Hz, 1H), 7.33-7.29 (m, 2H), 7.18 (m, 1H), 7.09-7.04 (m, 2H), 6.86 (d, J=8.4 Hz, 1H), 6.66-6.62 (m, 2H), 6.53 (dt, J=10.8, J=2.4 Hz, 1H), 4.88 (s, 2H), 4.15 (dd, J=9.6 Hz, J=3.6 Hz, 1H), 3.98-3.88 (m, 2H), 3.51-3.47 (m, 1H), 3.23-3.18 (m, 1H), 2.08-1.97 (m, 2H), 1.84-1.72 (m, 2H). TLC (UV$_{254}$) R$_f$=0.64 (2:1 ethyl acetate/hexanes). HPLC t$_R$=12.57 min.

(S)-1-(4-Fluorobenzyl)-5-(2-(2,4-difluorophenoxymethyl)-pyrrolidine-1-sulfonyl)isatin (compound 2)

2 was prepared according to the procedure for 22 except using 20d to give an orange gum (32 mg, 60%). HRMS (ESI)=531.1204 (M+H)$^+$. Calcd. for C$_{26}$H$_{22}$F$_3$N$_2$O$_5$S 531.1202. $^1$H NMR (600 MHz, CDCl$_3$) δ 8.03 (d, J=1.8 Hz, 1H), 7.98 (dd, J=8.4 Hz, J=1.8 Hz, 1H), 7.33-7.30 (m, 2H), 7.09-7.06 (m, 2H), 6.95-6.91 (m, 1H), 6.88 (d, J=8.4 Hz, 1H), 6.81-6.76 (m, 2H), 4.93 (d, J=16.2 Hz, 1H), 4.92 (d, J=16.2 Hz, 1H), 4.18 (dd, J=9 Hz, J=3 Hz, 1H), 4.00-3.95 (m, 2H), 3.51-3.49 (m, 1H), 3.21-3.17 (m, 1H), 2.09-1.98 (m, 2H), 1.85-1.74 (m, 2H). TLC (UV$_{254}$) R$_f$=0.67 (2:1 ethyl acetate/hexanes). HPLC t$_R$=12.50 min.

(S)-1-(4-Fluorobenzyl)-5-(2-(3,5-difluorophenoxymethyl)-pyrrolidine-1-sulfonyl)isatin (compound 3)

3 was prepared according to the procedure for 22 except using 20e to give an orange gum (31 mg, 58%). HRMS (ESI)=531.1213 (M+H)$^+$. Calcd. for C$_{26}$H$_{22}$F$_3$N$_2$O$_5$S 531.1202. $^1$H NMR (600 MHz, CDCl$_3$) δ 8.04 (d, J=1.8 Hz, 1H), 7.99 (dd, J=8.4 Hz, J=1.8 Hz, 1H), 7.34-7.29 (m, 2H), 7.09-7.06 (m, 2H), 6.90 (d, J=8.4 Hz, 1H), 6.44-6.38 (m, 3H), 4.93 (s, 2H), 4.18-4.15 (m, 1H), 3.94-3.89 (m, 2H), 3.51-3.48 (m, 1H), 3.19-3.15 (m, 1H), 2.03-1.93 (m, 2H), 1.83-1.73 (m, 2H). TLC (UV$_{254}$) R$_f$=0.64 (2:1 ethyl acetate/hexanes). HPLC t$_R$=13.00 min.

(S)-1-(4-Fluorobenzyl)-5-(2-(tetrahydro-2H-pyran-4-yloxymethyl)-pyrrolidine-1-sulfonyl)isatin (compound 4)

4 was prepared according to the procedure for 22 except using 20f to give an orange gum (26 mg, 52%). HRMS (ESI)=503.1646 (M+H)$^+$. Calcd. for C$_{25}$H$_{28}$FN$_2$O$_6$S 503.1652. $^1$H NMR (600 MHz, CDCl$_3$) δ 8.06 (d, J=1.8 Hz, 1H), 8.01 (dd, J=8.4 Hz, J=1.8 Hz, 1H), 7.34-7.31 (m, 2H), 7.10-7.06 (m, 2H), 6.91 (d, J=8.4 Hz, 1H), 4.87 (s, 2H), 3.93-3.88 (m, 2H), 3.73-3.70 (m, 1H), 3.67 (dd, J=9 Hz, J=3 Hz, 1H), 3.55-3.49 (m, 1H), 3.47-3.41 (m, 4H), 3.10-3.05 (m, 1H), 1.97-1.85 (m, 4H), 1.70-1.63 (m, 2H), 1.59-1.54 (m, 2H). TLC (UV$_{254}$) R$_f$=0.55 (4:1 ethyl acetate/hexanes). HPLC t$_R$=8.58 min.

(S)-1-(4-Fluorobenzyl)-5-(2-(pyrimidin-4-yloxymethyl)-pyrrolidine-1-sulfonyl)isatin (compound 5)

5 was prepared according to the procedure for 22 except using 20g to give an orange gum (12 mg, 24%). HRMS (ESI)=497.1287 (M+H)$^+$. Calcd. for C$_{24}$H$_{22}$FN$_4$O$_5$S 497.1295. $^1$H NMR (600 MHz, CDCl$_3$) δ 8.77 (s, 1H), 8.43 (d, J=5.4 Hz, 1H), 8.08 (d, J=1.8 Hz, 1H), 8.01 (dd, J=8.4 Hz, J=1.8 Hz, 1H), 7.34-7.32 (m, 2H), 7.09-7.06 (m, 2H), 6.89 (d, J=8.4 Hz, 1H), 6.70 (d, J=5.4 Hz, 1H), 4.90 (s, 2H), 4.55 (dd, J=10.8 Hz, J=4.2 Hz, 1H), 4.37 (dd, J=10.8 Hz, J=7.8 Hz, 1H), 4.05-4.01 (m, 1H), 3.50-3.46 (m, 1H), 3.22-3.19 (m, 1H), 1.98-1.87 (m, 2H), 1.81-1.72 (m, 2H). TLC (UV$_{254}$) R$_f$=0.32 (2:1 ethyl acetate). HPLC t$_R$=7.45 min.

(S)-1-(4-Fluorobenzyl)-5-(2-(2-propynyloxymethyl)-pyrrolidine-1-sulfonyl)isatin (compound 23)

23 was prepared according to the procedure for 22 except using 20h to give an orange gum. Recrystallization from ethyl acetate/hexanes furnished the desired product as orange needles (93 mg, 58%). HRMS (ESI)=457.1236 (M+H)$^+$. Calcd. for C$_{23}$H$_{22}$FN$_2$O$_5$S 457.1233. $^1$H NMR (600 MHz, CDCl$_3$) δ 8.07 (d, J=1.8 Hz, 1H), 8.01 (dd, J=8.4 Hz, J=1.8 Hz, 1H), 7.43-7.31 (m, 2H), 7.09-7.04 (m, 2H), 6.90 (d, J=8.4 Hz, 1H), 4.91 (s, 2H), 4.13 (d, J=2.4 Hz, 2H), 3.81-3.77 (m, 1H), 3.69 (dd, J=9.6 Hz, J=4.2 Hz, 1H), 3.51 (dd, J=9 Hz, J=7.2 Hz, 1H), 3.43-3.40 (m, 1H), 3.16-3.12 (m, 1H), 2.43 (t, J=2.4 Hz, 1H), 1.94-1.87 (m, 2H), 1.75-1.66 (m, 2H). TLC (UV$_{254}$) R$_f$=0.62 (2:1 ethyl acetate/hexanes). HPLC t$_R$=8.80 min.

(S)-1-(2-Propynyl)-5-(2-phenoxymethyl-pyrrolidine-1-sulfonyl)isatin (compound 24)

To a solution of (S)-5-(2-phenoxymethyl-pyrrolidine-1-sulfonyl)isatin 20a (0.39 g, 1 mmol) in dry DMF (10 mL) was added potassium carbonate (0.21 g, 1.5 mmol) followed by propargyl bromide (80 wt. % in toluene) (0.14 g, 1.2 mmol). After 2 h TLC indicated complete conversion of 20a and the solution was poured onto 10% aq. NH$_4$Cl (20 mL) and washed with DCM (3×10 mL). The combined organic fractions were then reduced in vacuo and the residue taken up in diethyl ether (10 mL) and washed with water (2×10 mL), then brine (1×10 mL) and dried over Na$_2$SO$_4$. Chromatography (hexanes/ethyl acetate) gave the product as an orange gum. Recrystallization from ethyl acetate/hexanes furnished the product as an orange solid (0.28 g, 66%). Mp: 115-117° C. HRMS (ESI)=425.1185 (M+H)$^+$. Calcd. for C$_{22}$H$_{21}$N$_2$O$_5$S 425.1171. $^1$H NMR (600 MHz, CDCl$_3$). δ 8.12 (dd, J=8.4 Hz, J=1.8 Hz, 1H), 8.05 (d, J=1.8 Hz, 1H), 7.25-7.21 (m, 2H), 7.16 (d, J=8.4 Hz, 1H), 6.96-6.93 (m, 1H), 6.81 (d, J=9 Hz, 2H), 4.56 (dd, J=18 Hz, J=2.4 Hz, 1H), 4.53 (dd, J=18 Hz, J=2.4 Hz, 1H), 4.19 (dd, J=9.6 Hz, J=3 Hz, 1H), 4.07-4.01 (m, 1H), 3.97 (dd, J=9.6 Hz, J=7.2 Hz, 1H), 3.55-3.51 (m, 1H), 3.33-3.28 (m, 1H), 2.36 (t, J=2.4 Hz, 1H), 2.09-1.99 (m, 2H), 1.89-1.75 (m, 2H). TLC (UV$_{254}$) R$_f$=0.54 (2:1 ethyl acetate/hexanes). HPLC t$_R$=9.00 min.

(S)-1-(2-Propynyl)-5-(2-(2,4-difluorophenoxymethyl)-pyrrolidine-1-sulfonyl)isatin (compound 25)

25 was prepared according to the procedure for 24 except using 20d to give an orange solid (0.48 g, 70%). Mp: 101-103° C. HRMS (ESI)=461.0976 (M+H)$^+$. Calcd. for C$_{22}$H$_{19}$F$_2$N$_2$O$_5$S 461.0983. $^1$H NMR (600 MHz, CDCl$_3$). δ 8.13 (dd, J=8.4 Hz, J=1.8 Hz, 1H), 8.07 (d, J=1.8 Hz, 1H), 7.24 (d, J=8.4 Hz, 1H), 6.96-6.92 (m, 1H), 6.85-6.78 (m, 2H), 4.59 (dd, J=18 Hz, J=2.4 Hz, 1H), 4.57 (dd, J=18 Hz, J=2.4 Hz, 1H), 4.24-4.20 (m, 1H), 4.03-3.98 (m, 2H), 3.55-3.52 (m, 1H), 3.26-3.21 (m, 1H), 2.37 (t, J=2.4 Hz, 1H), 2.12-2.01 (m, 2H), 1.88-1.76 (m, 2H). TLC (UV$_{254}$) R$_f$=0.63 (2:1 ethyl acetate/hexanes). HPLC t$_R$=9.60 min.

(S)-1-((1-(2-Fluoroethyl)-1H-[1,2,3]-triazol-4-yl)methyl)-5-(2-phenoxymethyl-pyrrolidine-1-sulfonyl)isatin (compound 10)

To a stirred solution of 24 (138 mg, 0.3 mmol) in dry DMF (3 mL) was added copper sulfate (38 mg, 0.15 mmol) in water (0.2 mL) followed by ascorbic acid (53 mg, 0.3 mmol) in water (0.2 mL and then 2-fluoroethylazide (33 mg, 0.36 mmol) in dry DMF (1.5 mL) and the mixture left to stir under argon. After 2 h TLC indicated reaction completion and mixture poured onto 10% aq. NH$_4$Cl (12 mL) and extracted with DCM (3×10 mL) and dried over Na$_2$SO$_4$. Chromatography (hexanes/ethyl acetate) afforded an orange solid (26 mg, 51%). Mp: 165-167° C. HRMS (ESI)=514.1557 (M+H)$^+$. Calcd. for C$_{24}$H$_{25}$FN$_5$O$_5$S 514.1560. $^1$H NMR (600 MHz, CDCl$_3$) δ 8.07 (dd, J=8.4 Hz, J=1.8 Hz, 1H), 8.01 (d, J=1.8 Hz, 1H), 7.76 (s, 1H), 7.47 (d, J=8.4 Hz, 1H), 7.23-7.19 (m, 2H), 6.92 (t, J=7.8 Hz, 1H), 6.82 (d, J=7.8 Hz, 2H), 5.03 (d, J=15.6 Hz, 1H), 5.02 (d, J=15.6 Hz, 1H), 4.79 (dt, J=46.2 Hz, J=4.8 Hz, 2H), 4.66 (dt, J=27 Hz, J=4.8 Hz, 2H), 4.17 (dd, J=9.6 Hz, J=3.6 Hz, 1H), 4.00-3.97 (m, 1H), 3.93 (dd, J=9 Hz, J=7.2 Hz, 1H), 3.53-3.49 (m, 1H), 3.27-3.24 (m, 1H), 2.08-1.97 (m, 2H), 1.86-1.75 (m, 2H). TLC (UV$_{254}$) R$_f$=0.56 (ethyl acetate). HPLC t$_R$=7.93 min.

(S)-1-((1-(2-Fluoroethyl)-1H-[1,2,3]-triazol-4-yl)methyl)-5-(2(2,4-difluorophenoxymethyl)-pyrrolidine-1-sulfonyl)isatin (compound 11)

11 was prepared according to the procedure for 10 except using 25 to give an orange gum. Recrystallization from ethyl acetate/hexanes gave an orange solid (94 mg, 57%). Mp: 130-131° C. HRMS (ESI)=550.1381 (M+H)$^+$. Calcd. for C$_{24}$H$_{23}$F$_3$N$_5$O$_5$S 550.1372. $^1$H NMR (600 MHz, CDCl$_3$) δ 8.08 (dd, J=8.4 Hz, J=1.8 Hz, 1H), 8.02 (d, J=1.8 Hz, 1H), 7.77 (s, 1H), 7.52 (d, J=8.4 Hz, 1H), 6.95-6.91 (m, 1H), 6.82-6.75 (m, 2H), 5.05 (s, 2H), 4.79 (dt, J=46.2 Hz, J=4.8 Hz, 2H), 4.67 (dt, J=26.4 Hz, J=4.8 Hz, 2H), 4.20 (dd, J=9.6 Hz, J=3 Hz, 1H), 4.01-3.94 (m, 2H), 3.53-3.50 (m, 1H), 3.22-3.17 (m, 1H), 2.10-1.98 (m, 2H), 1.85-1.74 (m, 2H). TLC (UV$_{254}$) R$_f$=0.47 (ethyl acetate). HPLC t$_R$=8.45 min.

(S)-1-((1-(Fluoromethyl)-1H-[1,2,3]-triazol-4-yl) methyl)-5-(2(2,4-difluorophenoxymethyl)-pyrrolidine-1-sulfonyl)isatin (compound 29)

was prepared according to the procedure for compound 11, with the exception that fluoromethylazide was used in place of the 2-fluoroethylazide.

(S)-1-((1-(3-Fluoropropyl)-1H-[1,2,3]-triazol-4-yl) methyl)-5-(2(2,4-difluorophenoxymethyl)-pyrrolidine-1-sulfonyl)isatin (compound 30)

was prepared according to the procedure for compound 11, with the exception that 3-fluoropropylazide was used in place of the 2-fluoroethylazide.

(S)-1-((1-(4-Fluorobutyl)-1H-[1,2,3]-triazol-4-yl) methyl)-5-(2(2,4-difluorophenoxymethyl)-pyrrolidine-1-sulfonyl)isatin (compound 31)

was prepared according to the procedure for compound 11, with the exception that 4-fluorobutylazide was used in place of the 2-fluoroethylazide.

(S)-1-(4-Fluorobenzyl)-5-(2-(1-((2-fluoroethyl)-1H-[1,2,3]-triazol-4-yl)methoxymethyl)-pyrrolidine-1-sulfonyl)isatin (compound 12)

12 was prepared according to the procedure for 10 except using 23 to give an orange gum (26 mg, 48%). HRMS (ESI)=546.1632 (M+H)$^+$. Calcd. for $C_{25}H_{26}F_2N_5O_5S$ 546.1623. $^1$H NMR (600 MHz, CDCl$_3$) δ 8.03 (d, J=1.8 Hz, 1H), 8.00 (dd, J=8.4 Hz, J=1.8 Hz, 1H), 7.67 (s, 1H), 7.35-7.33 (m, 2H), 7.08-7.05 (m, 2H), 6.90 (d, J=8.4 Hz, 1H), 4.95 (s, 2H), 4.81 (dt, J=46.8 Hz, J=4.8 Hz, 2H), 4.67 (dt. J=26.4 Hz, J=4.8 Hz, 2H), 4.62 (d, J=12 Hz, 1H), 4.60 (d, J=12 Hz, 1H), 3.81-3.78 (m, 1H), 3.65 (dd, J=9.6 Hz, J=4.2 Hz, 1H), 3.51 (dd, J=9.6 Hz, J=7.2 Hz, 1H), 3.40-3.37 (m, 1H), 3.19-3.15 (m, 1H), 1.92-1.87 (m, 2H), 1.72-1.66 (m, 2H). TLC (UV$_{254}$) R$_f$=0.35 (ethyl acetate). HPLC t$_R$=6.58 min.

(S)-1-(4-Fluorobenzyl)-5-(2-(1-((fluoromethyl)-1H-[1,2,3]-triazol-4-yl)methoxymethyl)-pyrrolidine-1-sulfonyl)isatin (compound 32)

is prepared according to the procedure for compound 12, with the exception that fluoromethylazide is used in place of the 2-fluoroethylazide.

(S)-1-(4-Fluorobenzyl)-5-(2-((1-(3-fluoropropyl)-1H-[1,2,3]-triazol-4-yl)methoxymethyl)-pyrrolidine-1-sulfonyl)isatin (compound 33)

is prepared according to the procedure for compound 12, with the exception that 3-fluoropropylazide is used in place of the 2-fluoroethylazide.

(S)-1-(4-Fluorobenzyl)-5-(2-((1-(4-fluorobutyl)-1H-[1,2,3]-triazol-4-yl)methoxymethyl)-pyrrolidine-1-sulfonyl)isatin (compound 34)

is prepared according to the procedure for compound 12, with the exception that 4-fluorobutylazide is used in place of the 2-fluoroethylazide.

Figure 2I:
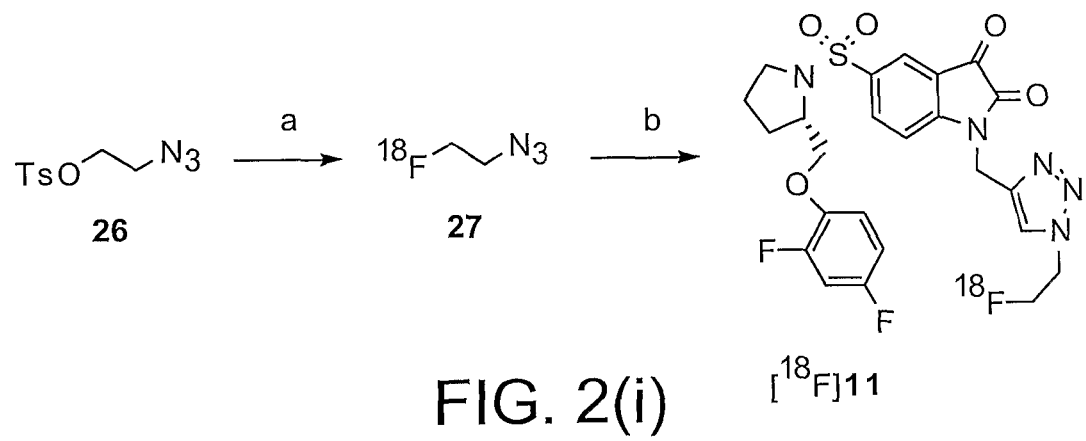
Figure 2:
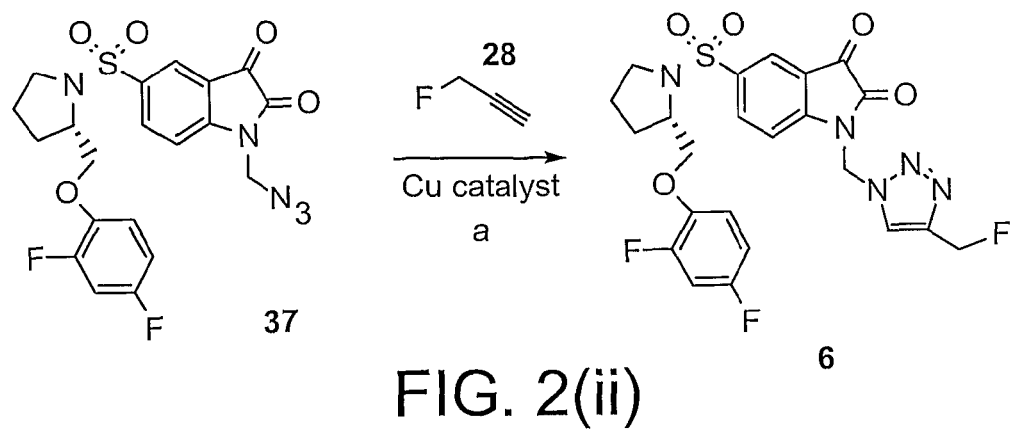

(S)-1-[4-(Fluoromethyl)-1H-[1,2,3]-triazol-1-yl] methyl-5-(2-(2,4-difluorophenoxymethyl)-pyrrolidine-1-sulfonyl)isatin) (compound 6)

is prepared as illustrated in FIG. 2(ii), by reaction of (S)-1-(azidomethyl)-5-(2-(2,4-difluorophenoxymethyl)-pyrrolidine-1-sulfonyl)isatin] (compound 37) with 3-fluoroprop-1-yne (compound 28). The reagents are as follows: (a) CuSO$_4$, L-ascorbic acid, DMF. For the preparation of [$^{18}$F]6, 3-[$^{18}$F] fluoroprop-1-yne is used in place of 3-fluoroprop-1-yne.

(S)-1-[4-(2-Fluoroethyl)-1H-[1,2,3]-triazol-1-yl] methyl-5-(2-(2,4-difluorophenoxymethyl)-pyrrolidine-1-sulfonyl)isatin) (compound 7)

is prepared according for the procedure for compound 6, with the exception that 4-fluorobut-1-yne is used in place of the (3-fluoroprop-1-yne). For the preparation of [$^{18}$F]7, 4-[$^{18}$F]fluorobut-1-yne is used in place of 3-fluoroprop-1-yne.

(S)-1-[4-(3-Fluoropropyl)-1H-[1,2,3]-triazol-1-yl] methyl-5-(2-(2,4-difluorophenoxymethyl)-pyrrolidine-1-sulfonyl)isatin) (compound 8)

is prepared according for the procedure for compound 6, with the exception that 5-fluoropent-1-yne is used in place of the (3-fluoroprop-1-yne). For the preparation of [$^{18}$F]8, 5-[$^{18}$F]fluoropent-1-yne is used in place of 3-fluoroprop-1-yne.

(S)-1-[4-(4-Fluorobutyl)-1H-[1,2,3]-triazol-1-yl] methyl-5-(2-(2,4-difluorophenoxymethyl)-pyrrolidine-1-sulfonyl)isatin) (compound 9)

is prepared according for the procedure for compound 6, with the exception that 6-fluorohex-1-yne is used in place of the (3-fluoroprop-1-yne). For the preparation of [$^{18}$F]9, 6-[$^{18}$F]fluorohex-1-yne is used in place of 3-fluoroprop-1-yne.

Figure 12:
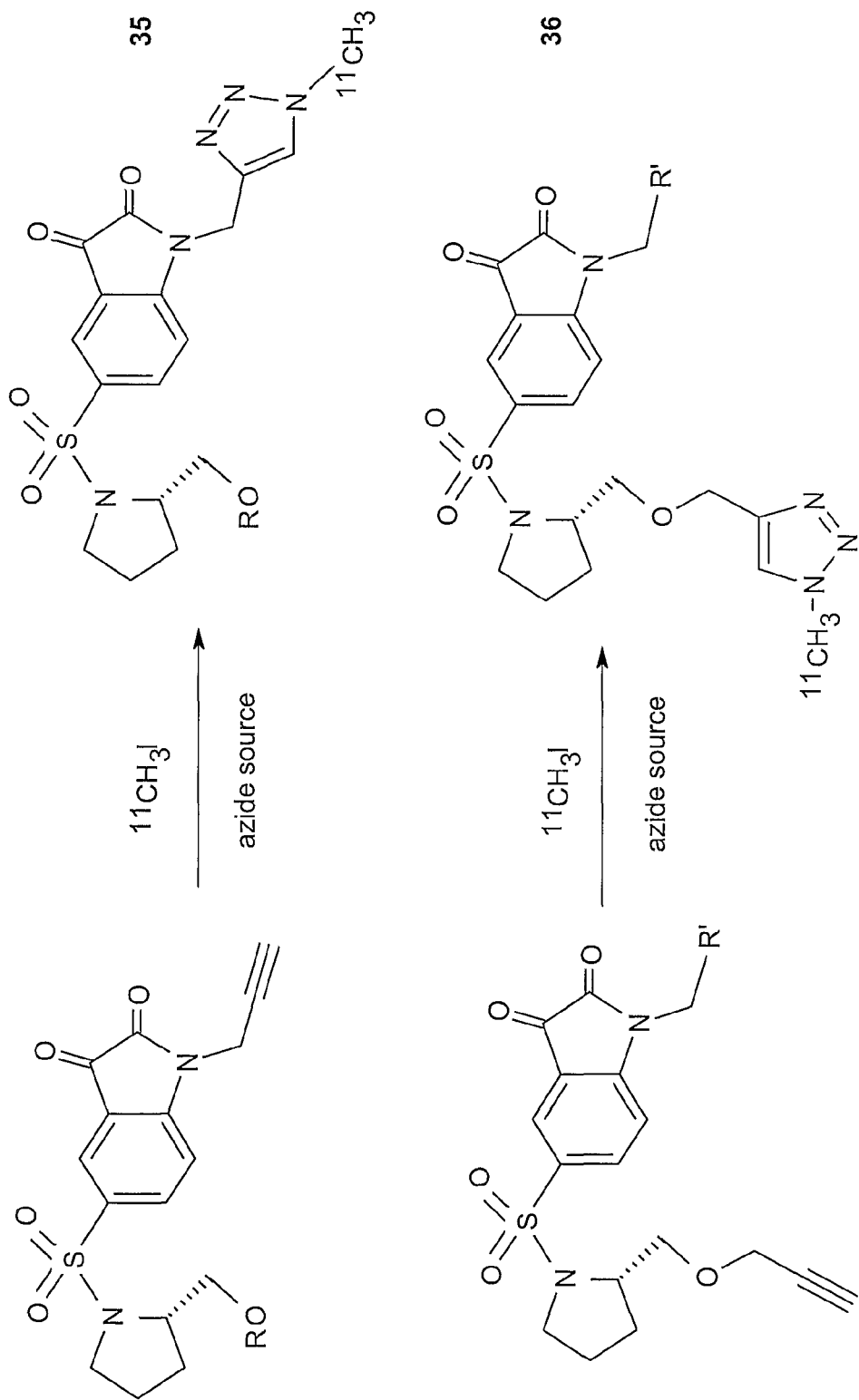

Compound 35 comprises a group of compounds wherein R is as previously defined. Compound 36 comprises a group of compounds wherein R' is as previously defined. These compounds can be produced using the method schematically represented in FIG. 12 (Top line=compound 35, bottom line=compound 36). This strategy involves the reaction of [$^{11}$C]methyl iodide with an azide source, either in situ or as a separate reaction, followed by cycloaddition with an appropriate alkyne. This method is a modification of a better-known click-chemistry strategy, recently reported in Schirrmacher, R. et al[25].

Example 2

Measuring Lipophilicity of Target Compounds and Affinity to Caspases

Affinity of Target Compounds to Caspases.

The affinities of the novel fluorinated isatins 1-5 and 10-12, and known isatin derivatives and intermediate compounds 22 and 23, for different activated caspases 1, 3, 6, 7, and 8 were measured by a fluorimetric in vitro caspase inhibition assay similar to that described by Kopka and co-workers.[13] Inhibition of recombinant human caspases was assessed by measuring the accumulation of a fluorogenic product, 7-amino-4-methylcoumarin (7-AMC).

Recombinant human caspases-1, -3, -6, -7, and -8 and their peptide-specific substrates were purchased from Biomol International, UK Inhibition of the recombinant caspases by non-radioactive isatins was assessed using a fluorometric assay that measures the accumulation of a fluorogenic product, 7-amino-4-methylcoumarin (7-AMC). All assays were performed in 96-well plates at a volume of 200 μl per well. The assays were performed at 37° C. in an appropriate reaction buffer as described below for each caspase. For caspase 1, the buffer comprised of 0.1% CHAPS, 100 mM NaCl, 5 mM 2-mercaptoethanol, 100 mM HEPES (pH 7.4), 2 mM EDTA, 10% sucrose, and 10 μM of the peptide substrate Ac-YVAD-AMC. For caspase 3: 20 mM HEPES (pH 7.4), 10% sucrose, 100 mM NaCl, 0.1% CHAPS, 2 m, mM EDTA, and 10 μM Ac-DEVD-AMC. For caspase 6: 20 mM HEPES (pH 7.4), 10% sucrose, 100 mM NaCl, 0.1% CHAPS, 2 mM EDTA, and 10 μM Ac-VEID-AMC. For caspase 7: 20 mM HEPES (pH 7.4), 10% sucrose, 5 mM 2-mercaptoethanol, 100 mM NaCl, 0.1% CHAPS, 2 mM EDTA, 10 μM Ac-DEVD-AMC. For caspase 8: 20 mM HEPES (pH 7.4), 10% sucrose, 100 mM NaCl, 0.1% CHAPS, 2 mM EDTA, and 10 μM Ac-IETD-AMC. The Buffers contained non-radioactive isatins in DMSO at a final concentration of 500, 50, 5 μM; 500, 50, 5 nM; 500, 50, 5 pM; the final concentration of DMSO in all wells was 5% of the total volume. Recombinant caspases were used at 0.5 units per assay (~500 pmol substrate converted per h). All reagents except the peptide substrate were pre-incubated for 10 min. The peptide substrate (final concentration 10 μM) was then added and the plate was incubated for a further 30 min; 30 min was selected after initial linearity study where reaction was assessed after 10, 30, 60 or 90 min. The 30 min time point was selected. Respective control wells contained all reaction components without enzyme. The amount of 7-AMC produced was measured on a fluorescence microplate reader (Victor2; Perkin-Elmer Life sciences) at excitation and emission wavelengths of 355 nm and 460 nm, respectively. The concentration of isatin that inhibits the caspase activity by 50% (EC50) was estimated by non-linear regression analysis using GraphPad Prism (Version 4.0 for Windows, GraphPad Software, San Diego Calif. USA). All the isatins were analyzed in duplicate; the assays were repeated once. Known compounds 13-16 were included as reference compounds. The results are summarized in Table 1 below.

The data are the average for two runs, each of which was duplicated, at nine concentrations ranging from 5 pM to 500 μM; the drug concentration required to inhibit each enzyme by 50% ($EC_{50}$) was obtained from nonlinear regression analysis of the inhibition profiles.

Results. In this assay the affinity of the known isatin 14 was 59.9 and 25.3 nM for caspase 3 and 7, respectively. Fluorine substituents on the phenyl ether were well tolerated, and for novel isatin 1 the affinity for caspase 3 increased two- to three-fold as compared with known non-fluorinated phenyl ether 14. The difluorinated isatins 2 and 3 were even more potent, with an affinity of 12.4 and 10.4 nM for caspase 3, respectively. Similar affinities were found for the tetrahydropyran 4. The five-fold increase in the potency of 4 as compared to the known benzyl derivative 15 is surprising given that this ring is fully saturated. Replacement of the phenyl ether with a pyrimidinyl group as in the pyrimidyl derivative 5 led to a further increase in potency, with affinities of 5.5 and 2.3 nM for caspase 3 and 7, respectively. Introduction of 2-fluoroethyl-1,2,3-triazole on either side of the molecule led to a sharp increase in potency, with measured caspase 3 affinities of 16.7 and 12.6 nM for the triazoles 10 and 12, respectively. The potency of the fluoroethyltriazole 12 was similar to that of 1-3, which is surprising given the considerably smaller size and higher polarity of this group. Lee[8] denoted the binding domain around the isatin nitrogen as a hydrophilic pocket, and most groups have since included benzyl moieties in this position. It was therefore highly unexpected that the triazole 10 is 4-fold more potent that the known benzyl derivative 15. Of the compounds tested, the triazole 11 was by far the most potent with affinities of 0.5 and 2.5 nM for caspase 3 and 7, respectively. All the compounds tested were poor substrates for caspase 1, 6 and 8 ($EC_{50}$>5000 nM).

Log P Calculation.

Lipophilicity was calculated from ACD/Chemsketch labs software.

Results.

The results are set out in Table 1 and 1a, below.

Table 1 and 1a.
Caspase inhibition profile and lipophilicity (P) of selected compounds.

| Compound | R | R' | Caspase $EC_{50}$ (nM)[a] 3 | 7 | 1/6/8 | cLog P[b] |
|---|---|---|---|---|---|---|
| 1 | 3-Fluorophenyl | 4-Fluorophenyl | 17.0 | 13.5 | >5000 | 3.80 |
| 2 | 2,4-Difluorophenyl | 4-Fluorophenyl | 12.4 | 13.0 | >5000 | 3.87 |
| 3 | 3,5-Difluorophenyl | 4-Fluorophenyl | 10.4 | 16.8 | >5000 | 3.94 |
| 4 | 4-tetrahydropyranyl | 4-Fluorophenyl | 10.7 | 14.4 | >5000 | 1.87 |
| 5 | Pyrimidin-4-yl | 4-Fluorophenyl | 5.5 | 2.3 | >5000 | 2.06 |
| 10 | Phenyl | 1-(2-Fluoroethyl)-1H-[1,2,3]-triazol-4-yl | 16.7 | 28.2 | >5000 | 1.38 |
| 11 | 2,4-Difluorophenyl | 1-(2-Fluoroethyl)-1H-[1,2,3]-triazol-4-yl | 0.5 | 2.2 | >5000 | 1.55[c] |
| 12 | (1-(2-Fluoroethyl)-1H-[1,2,3]-triazol-4-yl)methyl | 4-Fluorophenyl | 12.6 | 18.3 | >5000 | 1.55 |
| 13 | Phenyl | Phenyl | 41.8 | 29.4 | >5000 | 3.65 |
| 14 | Phenyl | 4-Iodophenyl | 59.9 | 25.3 | >5000 | 4.68 |
| 15 | Phenyl | 4-Fluorophenyl | 50.5 | 19.8 | >5000 | 3.70 |
| 22 | 4-Fluorophenyl | 4-Fluorophenyl | 26.1 | 8.0 | >5000 | 3.83 |
| 25 | 2,4-Difluorophenyl | ethynyl | 50.1 | 60.4 | >5000 | 2.42 |

-continued

Table 1a

| Compound | Name of Compound | Caspase EC$_{50}$ (nM)$^a$ | | | cLog P$^b$ |
|---|---|---|---|---|---|
| | | 3 | 7 | 1/6/8 | |
| 16 | 1-(4-Fluorobenzyl)-5-(pyrrolidine-1-sulfonyl)isatin | 199.5 | 78.6 | >5000 | 1.93 |

$^a$Each value is average of two measurements at each concentration for each entry;
$^b$Values calculated using ACD Labs software;
$^c$Measured Log P for [$^{18}$F]11 = 1.61.

Example 3

Synthesis of [$^{18}$F]11

Preferably, compound [$^{18}$F]11 is produced by 'click-labelling' of (S)-1-(2-Propynyl)-5-(2-(2,4-difluorophenoxymethyl)-pyrrolidine-1-sulfonyl)isatin (compound 25) with [$^{18}$F]fluoroethylazide (compound 27).[15,16] The triazole (S)-1-((1-(2-Fluoroethyl)-1H-[1,2,3]-triazol-4-yl)methyl)-5-(2 (2,4-difluorophenoxymethyl)-pyrrolidine-1-sulfonyl)isatin (compound 11) was labelled by copper catalyzed cycloaddition of 2-[$^{18}$F]fluoroethylazide (compound 27) with the alkyne precursor (S)-1-(2-Propynyl)-5-(2-(2,4-difluorophenoxymethyl)-pyrrolidine-1-sulfonyl)isatin (compound 25) as shown in FIG. 2(i) and in FIG. 19. The same method can be used to produce non-radiolabelled compound 11, wherein fluoroethylazide is used in place of 2-[$^{18}$F]fluoroethylazide Under an atmosphere of nitrogen, a buffered solution (sodium phosphate buffer, pH 6.0, 250 mM) of sodium ascorbate (50 µl, 8.7 mg, 43.2 µmol) was added to a Wheaton vial (1 mL) containing an aqueous solution of copper(II) sulfate (50 µl, 1.7 mg pentahydrate, 7.0 µmol). After one minute, a solution of alkyne 25 (3.0 mg, 6.5 µmol) in dimethylformamide (25 µl) was added followed by distilled [$^{18}$F]FEA (185-740 MBq) in acetonitrile (100 µl). The mixture was left at room temperature for 30 minutes and applied to preparative radio-HPLC after addition of water (15 µl). The isolated HPLC product solution was diluted with water (5 mL) and loaded onto a SepPak C18-light cartridge (Waters) that had been conditioned with ethanol (5 mL) and water (10 mL). The cartridge was subsequently flushed with water (5 mL) and $^{18}$F-9 eluted with ethanol in small fractions (0.1 mL). The product fraction was diluted with PBS to provide an ethanol content of 10-15% (v/v).

Results.

Figure 3:
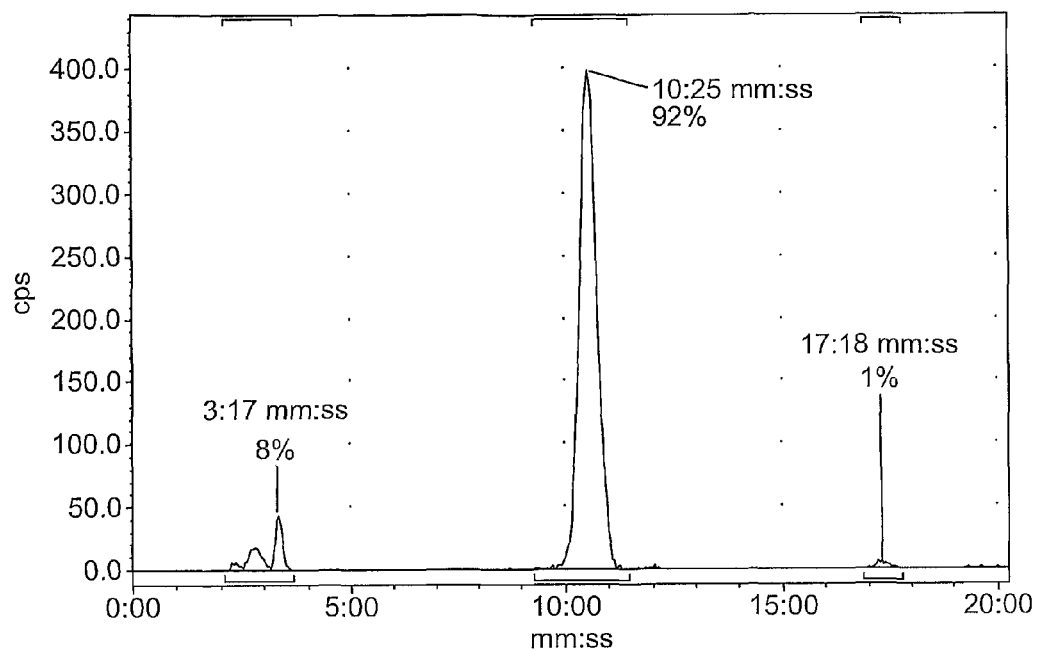
Figure 3:
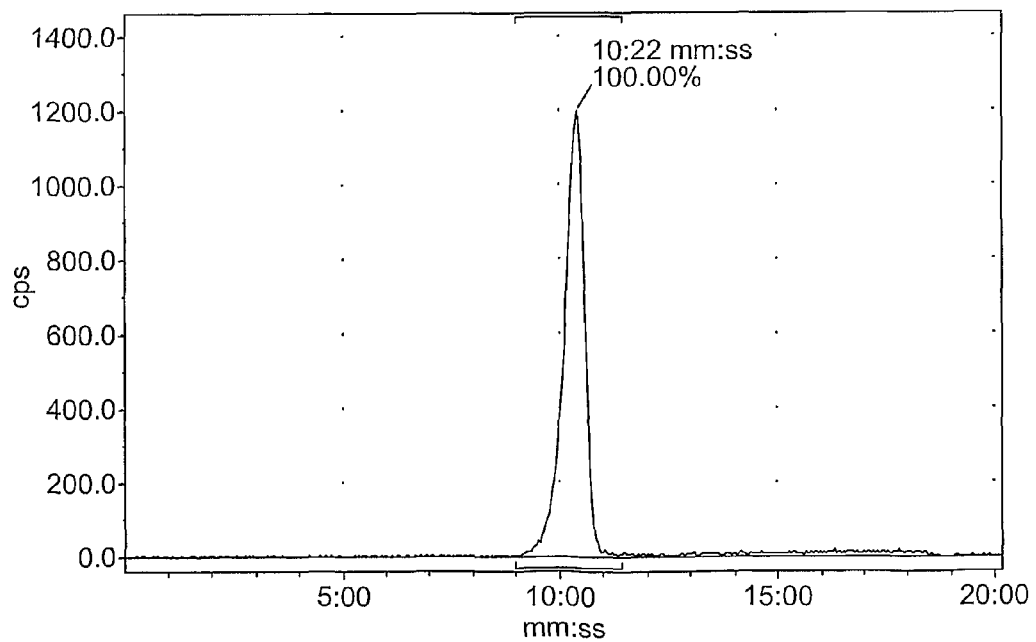
Figure 3:
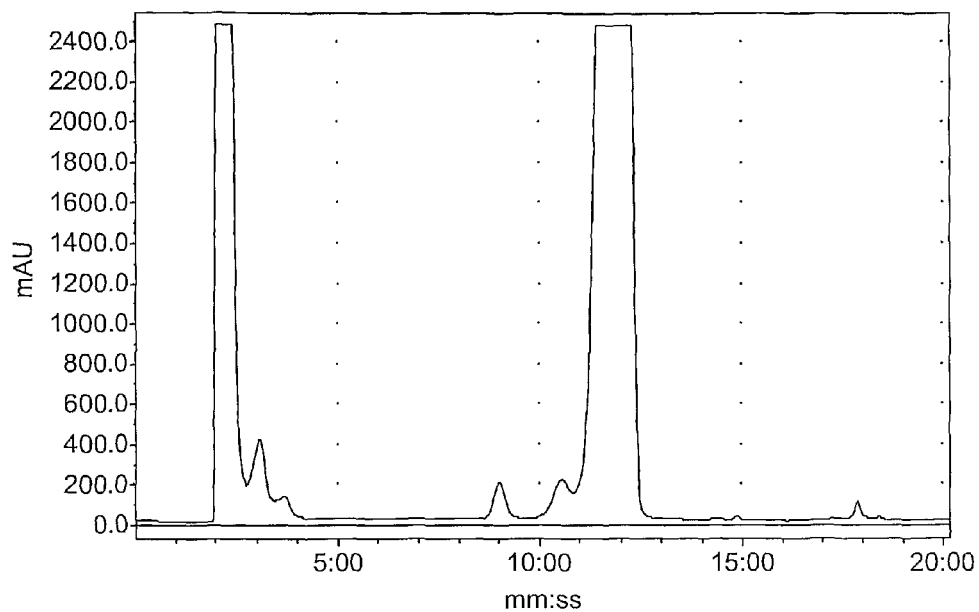
Figure 3:
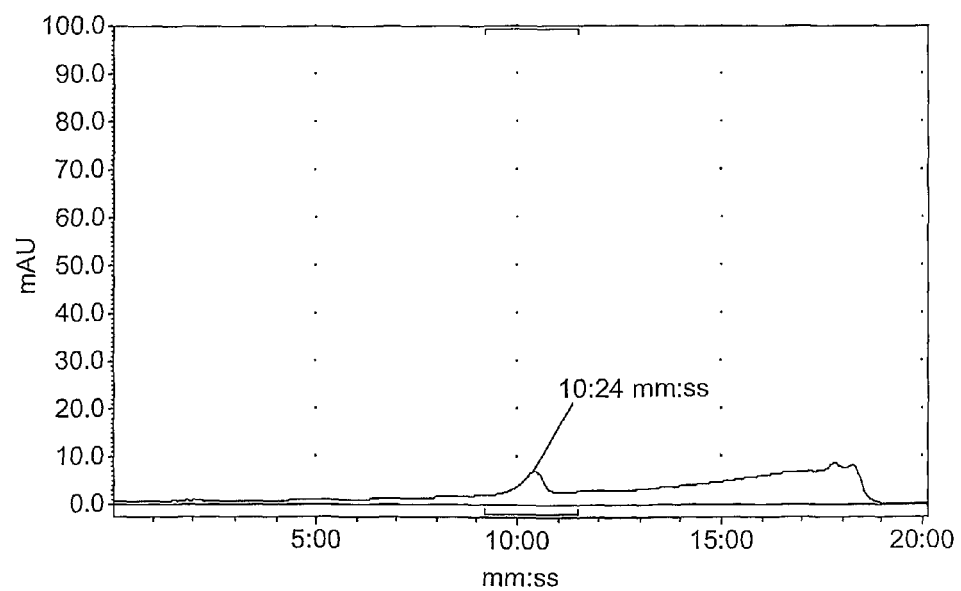

Initial attempts to conjugate 27 with the alkyne precursor 25 led to formation of a complex mixture of radioactive products. Further investigation of the impact of the catalytic system, temperature and pH on the radiochemical yield revealed poor thermal stability of [$^{18}$F]9, with the highest yields obtained at room temperature. Addition of sodium phosphate buffer (pH 6.0, 250 mM) to the reaction mixture dramatically improved the radiochemical yield, whereas only minor differences were observed for the two catalytic systems investigated (copper powder or copper sulfate/ascorbate). The optimal conditions were found to be 30 min reaction time at room temperature in the presence of a slight excess of copper sulfate relative to the alkyne precursor 25. This provided the triazole [$^{18}$F]11 in 65±6% (n=26, decay-corrected from 27) isolated radiochemical yield with a radiochemical purity of >99% after purification by HPLC. A typical HPLC chromatogram for the product mixture is shown in FIG. 3. As the procedure was carried out manually with low amounts of radioactivity only modest specific activity (1.2 GBq/µmol) was achieved at end of synthesis. The identity of [$^{18}$F]11 was confirmed by co-elution with the non-radioactive reference compound. The purified [$^{18}$F]11 was formulated by solid-phase extraction with an efficiency of 91±6% (n=26, decay-corrected). The radiosynthesis including formulation of [$^{18}$F]11 took three hours in total.

Example 4

Lipophilicity of [$^{18}$F]11

Log P Determination.

Lipophilicity was assessed by measuring the octanol-water partition coefficient using the method of Barthel et al[18]. Briefly, [$^{18}$F]11 (~180 µCi in 25 µL ethanol) was diluted to a final volume of 100 µL using water to give the stock solution. Aliquots of stock solution (10 µL) were added to water (490 µL) and octan-1-ol (Aldrich anhydrous grade) (500 µL). The solutions were then shaken vigorously for 10 min then centrifuged (13201 g, 20° C., 30 min) Following centrifugation portions (200 µL) of the water and octanol layers were carefully removed and placed analyzed on a Cobra II Auto-Gamma counter (Packard Instruments, Meriden, Conn., USA) and compared. The octanol-water partition coefficient was obtained by dividing the octanol containing radioactivity by the water containing radioactivity. Log P was determined to be 1.61, as indicated in footnote c of Table 1 above.

Example 5

Tissue Distribution and Metabolic Stability of [$^{18}$F]11 and [$^{125}$I]14

The stability of novel compound [$^{18}$F]11 and known compound [$^{125}$I]14 in plasma and liver was measured over time following administration in mice. [$^{18}$F]11 was injected intravenously into tumor-bearing mice and its tissue distribution was measured in selected tissues at 2, 15 and 60 min after injection. [$^{125}$I]14 was injected intravenously into non-tumour bearing mice and its tissue distribution was measured at selected time points from 2 to 60 minutes after injection. Furthermore, the in vivo metabolic stability of the radiotracer was determined from plasma and liver samples and, for [$^{18}$F]11, in urine samples.

In Vitro Mouse Liver S9 Metabolism Studies.

Liver S9 metabolism studies were performed as described in Aboagye et al[19]. Mouse livers were rapidly excised and kept at 4° C. throughout the experiment. Tissues were weighed and homogenized in an equivalent volume of 50 mM Tris-150 mM KCl-HCl buffer (pH 7.4) using an Ultra-Thurrax homogenizer (IKA, Staufen, Germany). To obtain the S9 fraction, the homogenate was centrifuged (10,000×g) for 30 min to remove nuclei, mitochondria and cell debris. Protein concentration of the S9 fraction was determined by a commercial BCA protein assay kit (Perbio Science, Cheshire, UK). S9 fractions were stored at −80° C. for up to 6 weeks. Selected unlabeled isatins 14, 15, 16 (10 mM, 10 μL) were incubated with the S9 fraction (33.26 mg/ml, 20 μL) and 0.5 mM nicotinamide adenine dinucleotide phosphate (reduce form) in air for 60 min at 37° C. in 0.1 mM Tris-HCl buffer (pH 7.4) in a total volume of 1 mL. Control incubation samples contained no isatin. The reactions were terminated by addition of ice-cold acetonitrile (2 mL); the samples were then immediately placed on dry ice prior to extraction and HPLC analysis (below).

In Vivo Biodistribution and Metabolism Studies.

The radiation-induced murine fibrosarcoma (RIF-1) tumour cells[20] were maintained in RPMI 1640 medium (Invitrogen Ltd, Paisley, UK) supplemented with 10% fetal calf serum (BioWhittaker Europe Ltd, Verviers, Belgium), 2 mM L-glutamine, 100 U/mL penicillin, 100 μg/mL streptomycin and 0.25 μg/mL fungizone (Gibco, UK) at 37° C. in a humidified incubator with 5% $CO_2$. All animal work was done by licensed investigators in accordance with the United Kingdom's "Guidance on the Operation of Animals (Scientific Procedures) Act 1986" (HMSO, London, United Kingdom, 1990) and in full compliance with government regulations and guidelines on the welfare of animals in experimental neoplasia[21]. Tumors were established in mice by subcutaneous injection of $5 \times 10^5$ cells on the back of male C3H/hej mice (Harlan, Bicester, Oxfordshire, UK). Tumour growth was monitored every two days using electronic callipers, and tumor volume estimated using the equation $(\pi/6) \times L \times W \times D$ (L=length, W=width and D=depth). Animals were selected for biodistribution studies of [$^{18}$F]11 when the tumors reached ~100-150 $mm^3$; biodistribution of [$^{125}$I]14 was done in non-tumor-bearing mice.

Mice were injected intravenously via the lateral vein with 0.08-0.13 mL of radioactivity (~0.37 MBq of [$^{125}$I]14 or 3.7 MBq of [$^{18}$F]11) dissolved in phosphate buffered saline. At selected times after injection (2-60 min) mice were sacrificed by exsanguination via cardiac puncture under general anesthesia (isofluorane inhalation). Aliquots of heparinised blood were rapidly centrifuged (2000 g for 5 minutes) to obtain plasma. The radioactivity contained in tissues was determined by gamma-counting on a Cobra II Auto-Gamma counter (Packard Instruments, Meriden, Conn., USA) and expressed as a percentage of injected dose per gram of tissue (% ID/g). A minimum of three mice was used for each time point. All animals were treatment-naïve.

In vivo metabolism studies were also performed in C3H/hej mice. Non-tumor-bearing mice were injected intravenously with 0.37 MBq of [$^{125}$I]14 or 7.4 MBq of [$^{18}$F]11 and plasma was obtained as above. Plasma, liver and urine samples were snap-frozen in liquid nitrogen and kept in pre-weighed scintillation counting tubes on dry ice prior to analysis.

HPLC Analysis.

Immediately prior to extraction the samples were thawed and placed on ice. For extraction, ice cold acetonitrile (1.5 mL) was added to plasma (0.2 mL); S9 incubation samples (3 mL) containing acetonitrile were also analysed. Each mixture was centrifuged (15493×g, 4° C., 3 min) and the resulting supernatant was evaporated to dryness under vacuum at 40° C. using a rotary evaporator. Liver samples were homogenized with ice cold acetonitrile (1.5 mL) using an IKA Ultra-Turrax T-25 homogeniser prior to centrifugation. The residues were then re-suspended in HPLC mobile phase (1.2 mL) and filtered through a Minisart hydrophilic syringe filter (0.2 μm) (Sartorius, Goettingen, Germany). Urine samples were diluted with HPLC mobile phase, filtered as above. The samples (1 mL) were then analyzed by radio-HPLC on an Agilent 1100 series HPLC system (Agilent Technologies, Stockport, UK) equipped with a γ-RAM Model 3 gamma-detector and the Laura software (IN/US Systems inc., Florida, USA).

The stationary phase comprised of a Waters μBondapak $C_{18}$ reverse-phase column (300×7.8 mm). For analysis of [$^{125}$I]14, plasma and liver samples were processed as above and analyzed by using a mobile phase comprising of water (0.1% TFA)/propan-1-ol (0.1% TFA) (35:65) running in isocratic mode at a flowrate of 2 mL/min. For analysis of unlabeled 14, 15 and 16 after in vitro metabolism, samples were analyzed using a mobile phase comprising of water (0.1% TFA)/propan-1-ol (0.1% TFA) with a gradient of 2→80% organic in 11 min, 80→5% organic in 3 min then 5% organic for 6 min delivered at a flowrate of 3 mL/min. For analysis of [$^{18}$F]9, plasma, liver and urine samples were analyzed using a mobile phase comprising of 0.1M ammonium formate/1.8:1 methanol:acetonitrile with a gradient of 50% organic for 1 min, 50→90% organic in 14 min, 90% organic for 3 min, 90→50% organic in 2 min, 50% organic for 4 min delivered at a flowrate of 3 mL/min. Furthermore, to assess the fraction of [$^{18}$F]9-derived radioactivity associated with the plasma and liver pellets after extraction versus that remaining in the HPLC injectate, the total volume of HPLC injectate was recorded and an aliquot (0.1 mL) removed for counting. The radioactivity in the 0.1 mL aliquot and the pellet were then analyzed by gamma counting (Packard Instruments).

Results.

Figure 4:
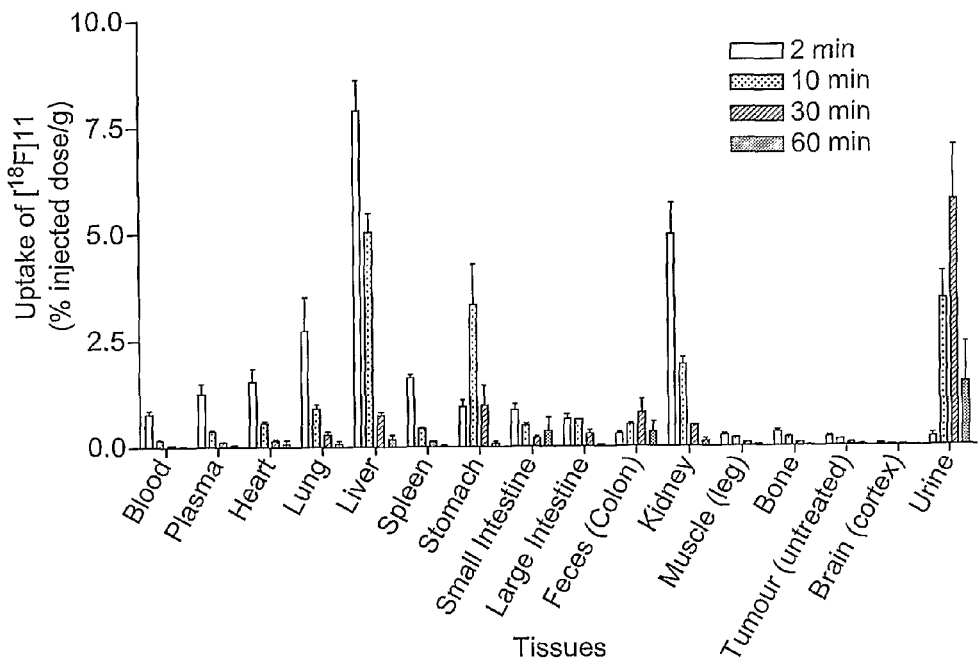
Figure 5:
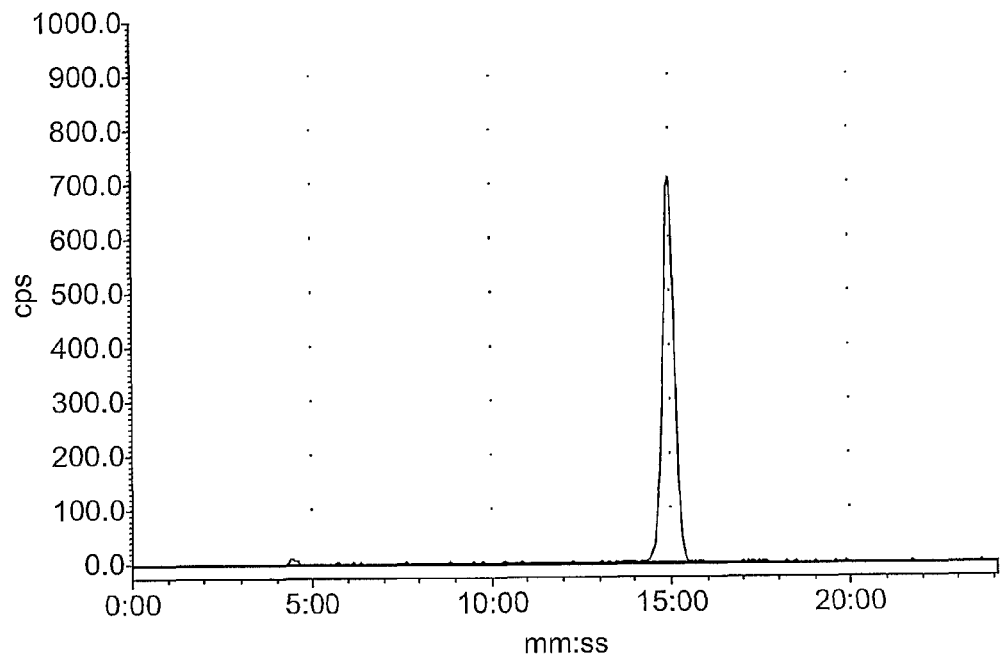
Figure 5:
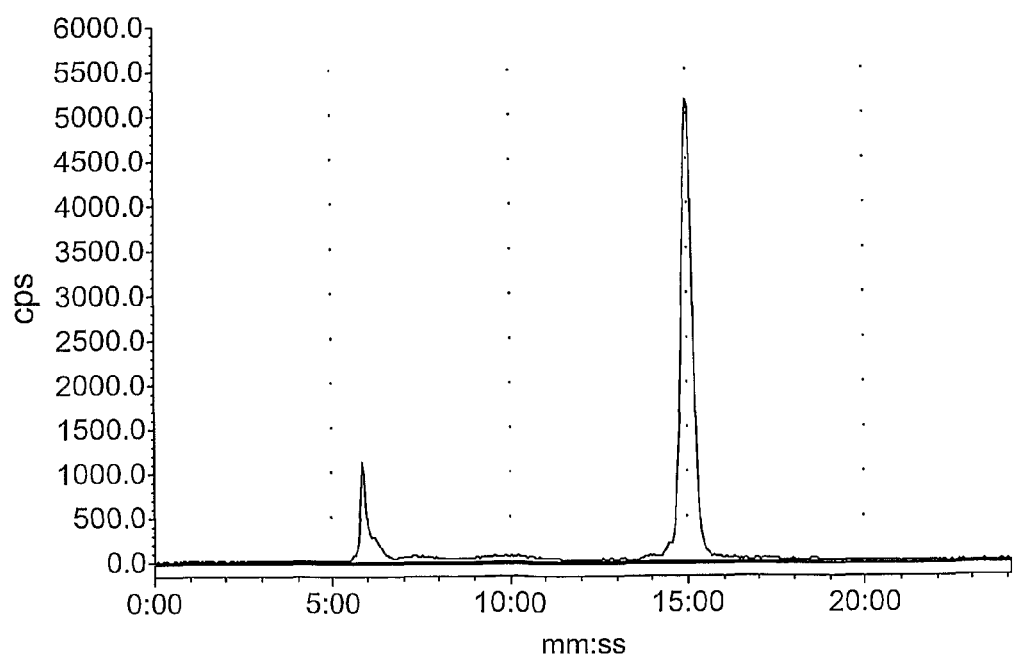
Figure 5:
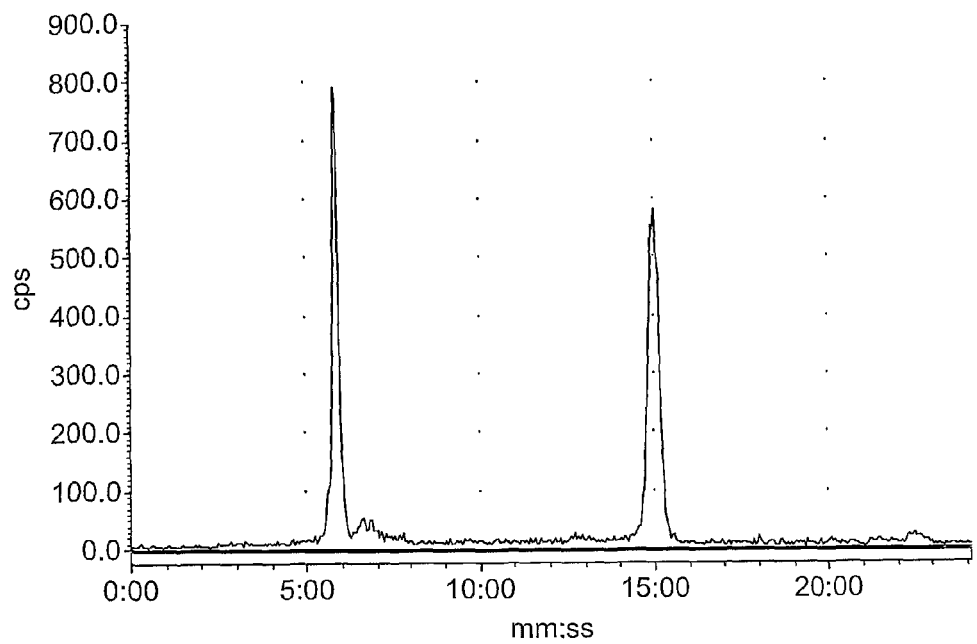
Figure 5:
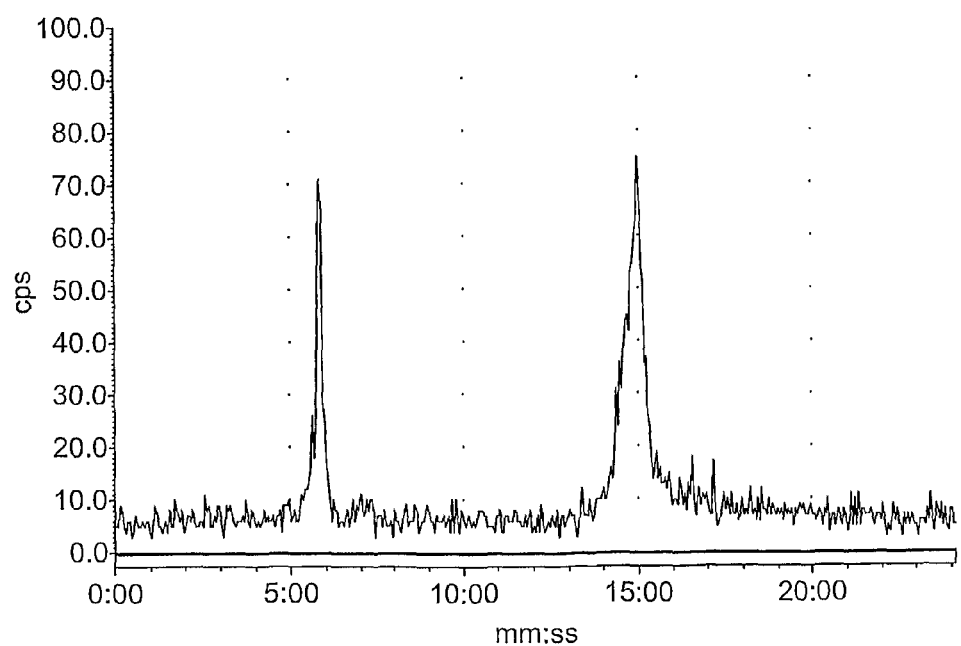
Figure 6:
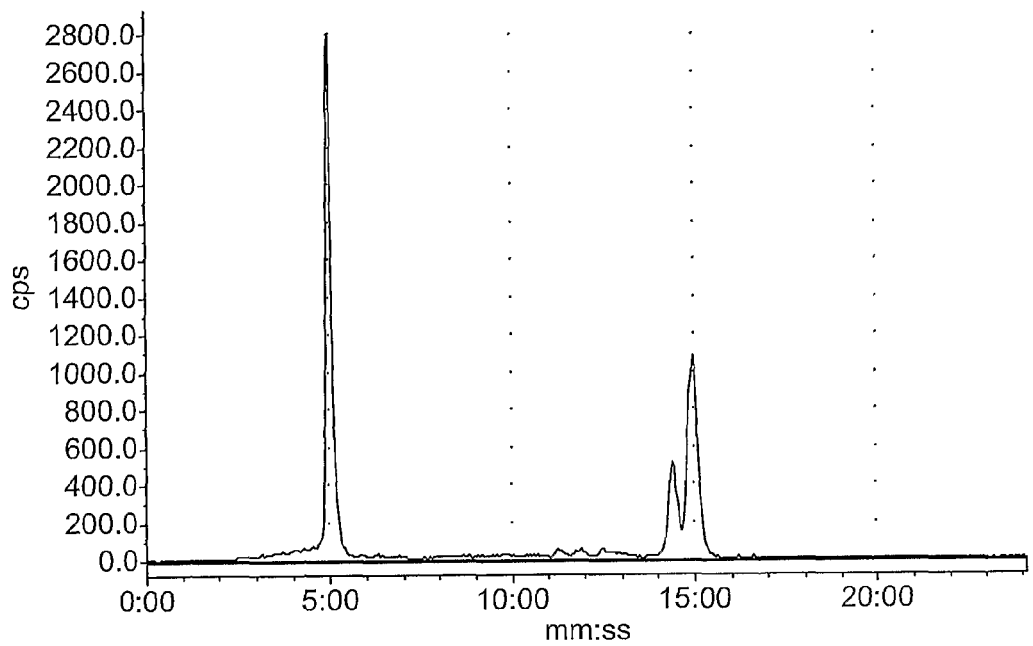
Figure 6:
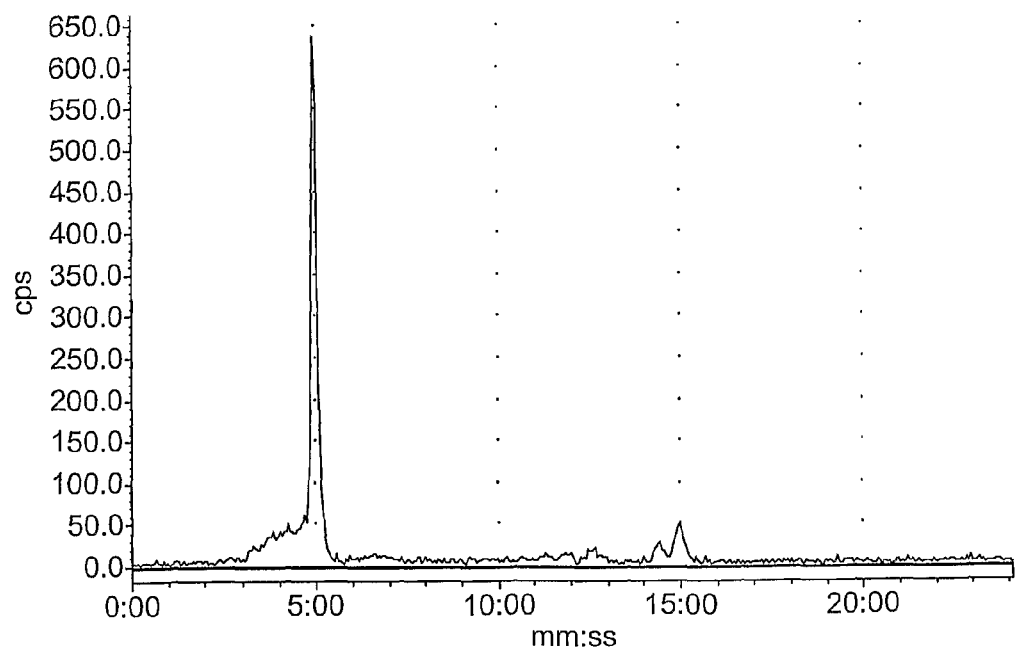
Figure 6:
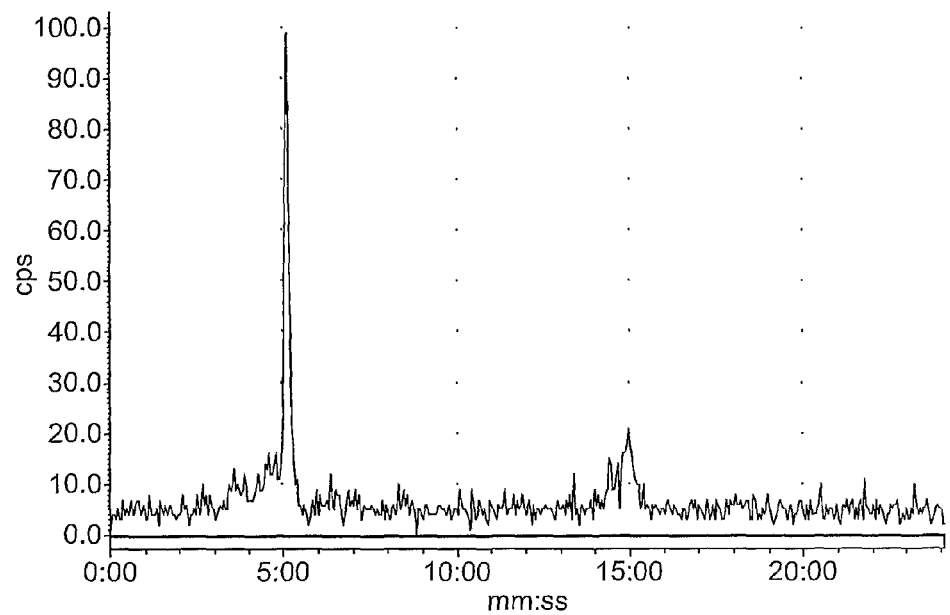
Figure 6:
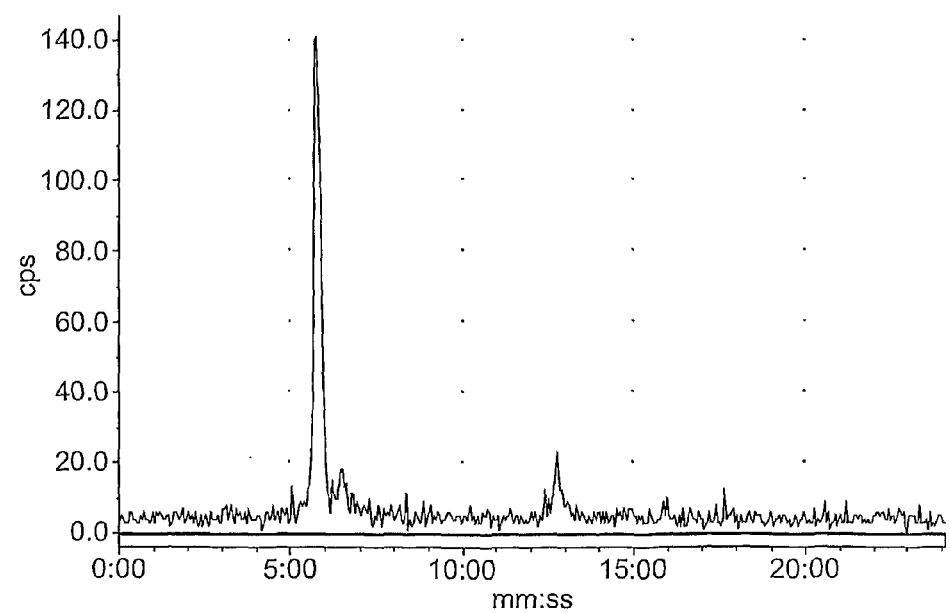
Figure 6:
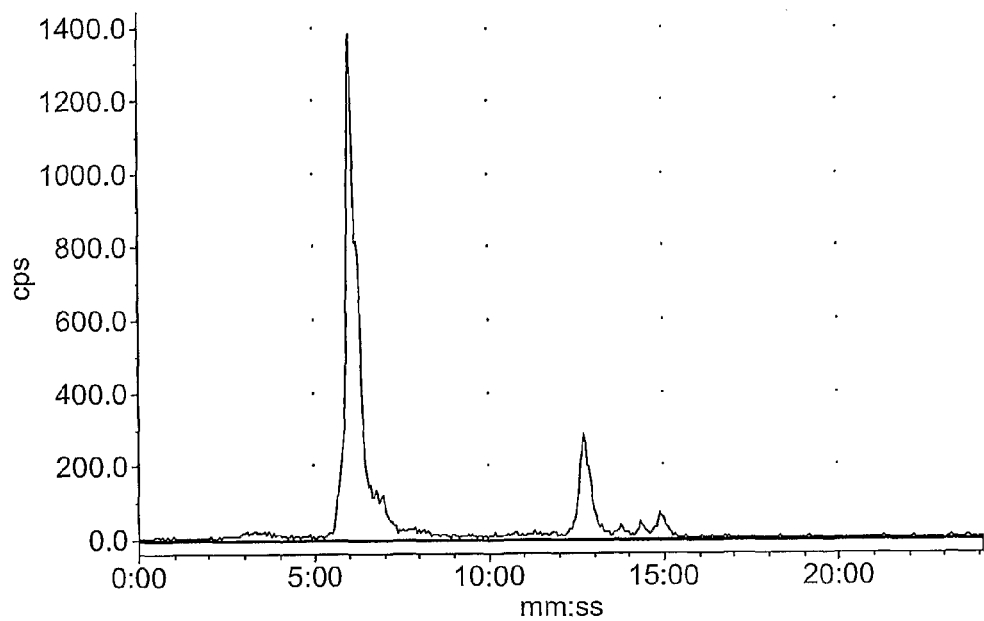
Figure 6:
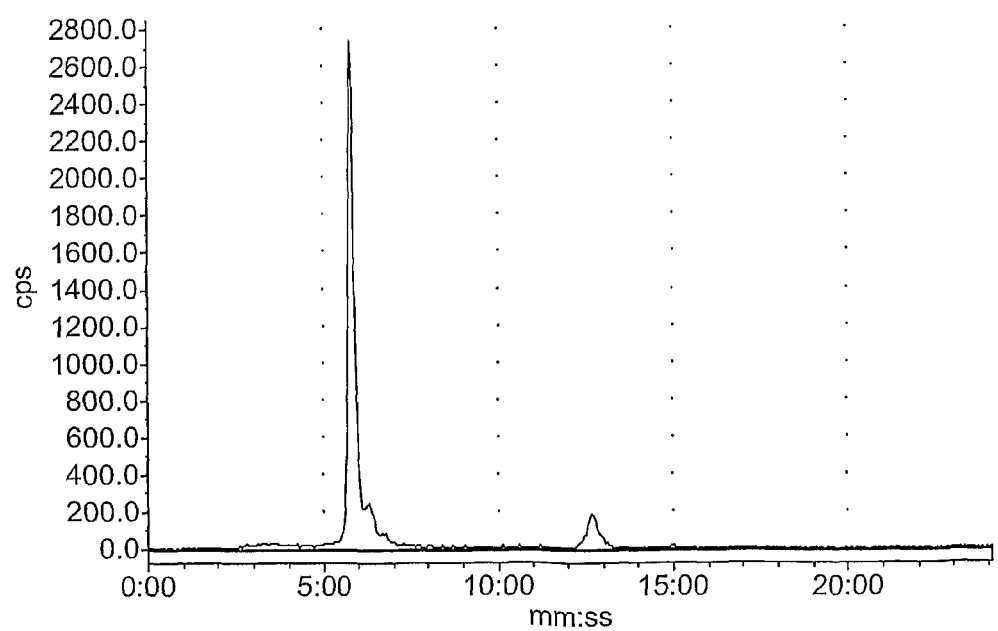

FIG. 4 shows that [$^{18}$F]11 distributed rapidly to tissues and was also rapidly eliminated. High localization of [$^{18}$F]11-derived radioactivity was seen in kidney, urine and liver, suggesting importance of both renal and hepatic routes of elimination. However, even in these tissues, rapid elimination of radioactivity was seen. Importantly, from an imaging standpoint, uptake of [$^{18}$F]11 in untreated tumors, heart and brain was low; this should facilitate measurement of increased binding associated with caspase activation in these tissues. Bone uptake was low, suggesting an absence of radiotracer defluorination and hence stability of the fluoroethylazide moiety. Radio-HPLC analysis showed that [$^{18}$F]11 was relatively more stable to metabolic degradation than [$^{125}$I]14 (FIG. 5) producing a single polar metabolite peak in plasma and liver. The parent compound was still present in plasma at 60 min and was the dominant peak. In contrast, the metabolite was the dominant peak in liver samples at all time points studied. Urine radioactivity comprised mainly of the metabolite. The proportions of parent radiotracer in plasma and liver at the selected timepoints, together with the apparent extraction efficiency are summarized in Table 2. Following a rapid decrease, the rate of in vivo metabolism appeared to plateau between 15 and 60 min. However, the extraction efficiencies from plasma and liver diminished over time probably due to non-specific binding. There was also a time-dependent increase in radioactivity in the residual pellets after plasma extraction, suggesting an increased binding to plasma proteins.

TABLE 2

In vivo metabolism of [$^{18}$F]11 at selected timepoints showing the proportion of [$^{18}$F]11 present in plasma and liver extracts. The extracts were analyzed by radio-HPLC. The efficiencies of extraction of radioactive analytes from the samples are reported below.

| Time (min) | Parent (plasma)[a] | Recovery (plasma)[a] | Parent (liver) | Recovery (liver) |
|---|---|---|---|---|
| 2  | 86.1 ± 3.7 | 92.1 ± 3.4 | 35.7/43.4 | 79.7/86.9 |
| 15 | 61.3 ± 5.9 | 76.8 ± 5.2 | 9.7/10.2  | 67.1/68.9 |
| 60 | 64.8 ± 7.0 | 50.9 ± 3.7 | 27.0/29.7 | 46.4/65.2 |

[a]Average of 3 results per timepoint. Individual results from two samples are reported for liver. Values expressed as percentages either for the relative proportion of parent compound [$^{18}$F]9 present in the HPLC analysis or the total amount of radioactivity extracted from the tissue sample as a proportion of the total radioactivity.

Figure 7:
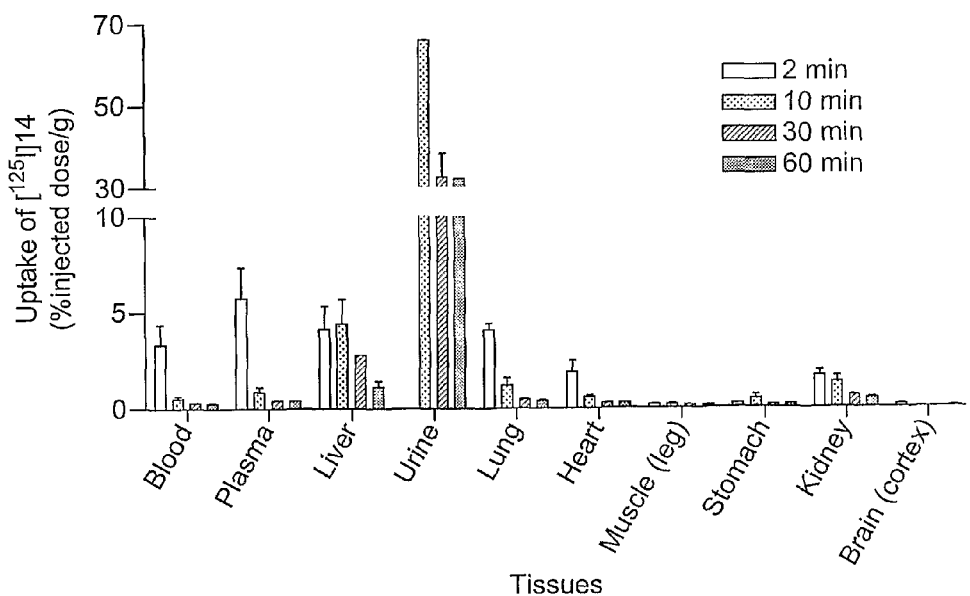

FIG. 7 shows that [$^{125}$I]14 was distributed rapidly to the major organs and was also rapidly eliminated. [$^{125}$I]14 was completely eliminated from plasma within 10 min, and represented <15% (n=3) of the radioactivity detected in the liver at this point of time. Within 30 min after injection, the parent [$^{125}$I]14 was fully metabolized in the liver, with a single, polar metabolite constituting the majority of the radioactivity detected. Consistent with these findings, we observed rapid clearance in all tissues investigated, and from 10 min onwards the majority of the injected radioactivity was excreted in the urine.

Figure 8:
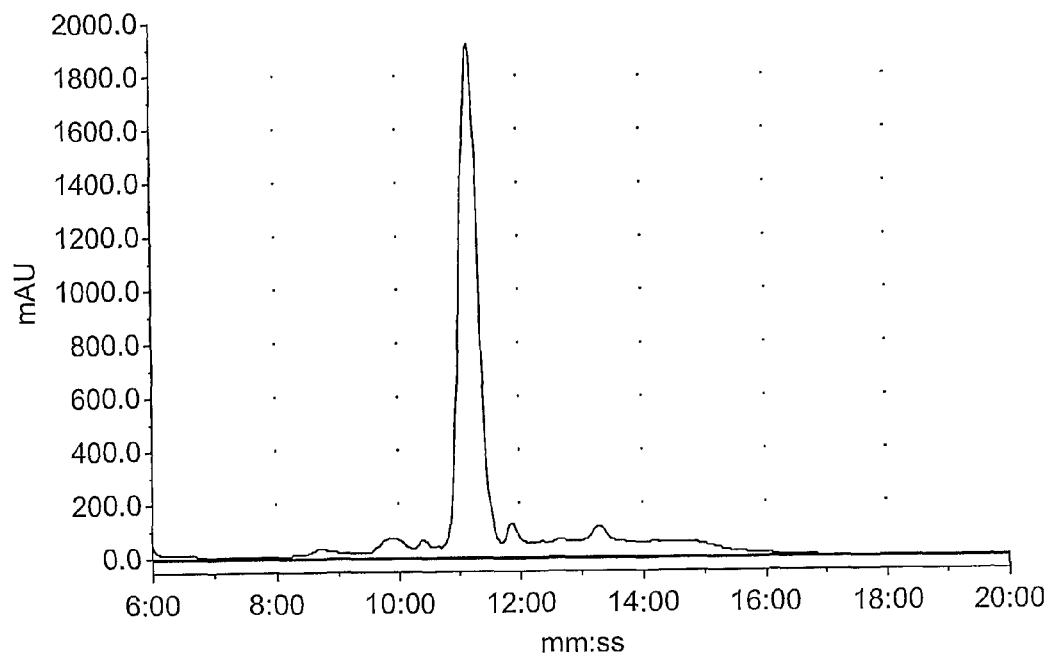
Figure 8:
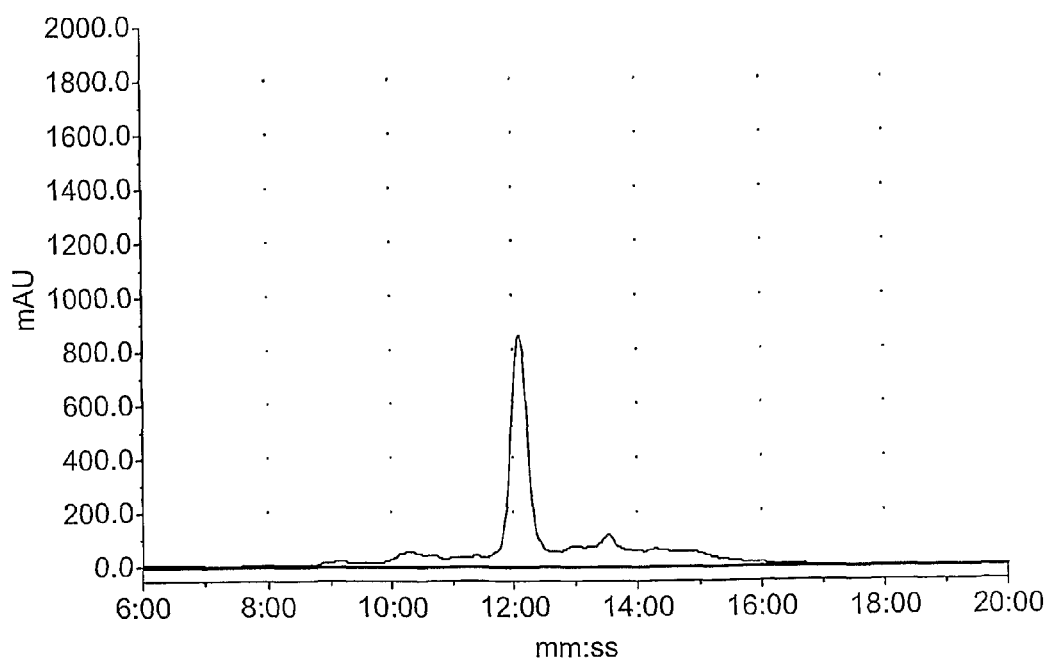
Figure 8:
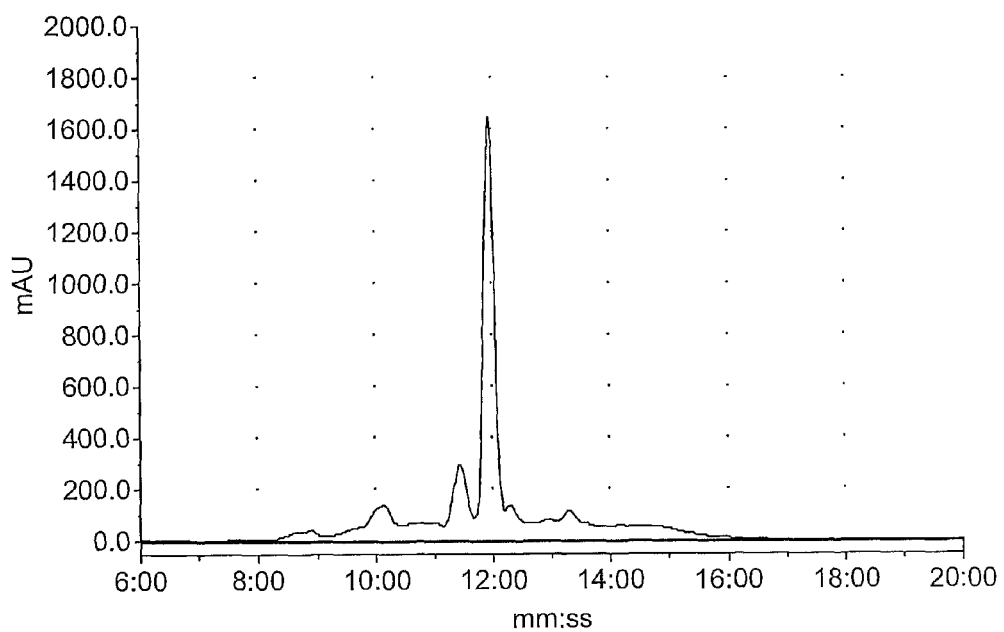
Figure 8:
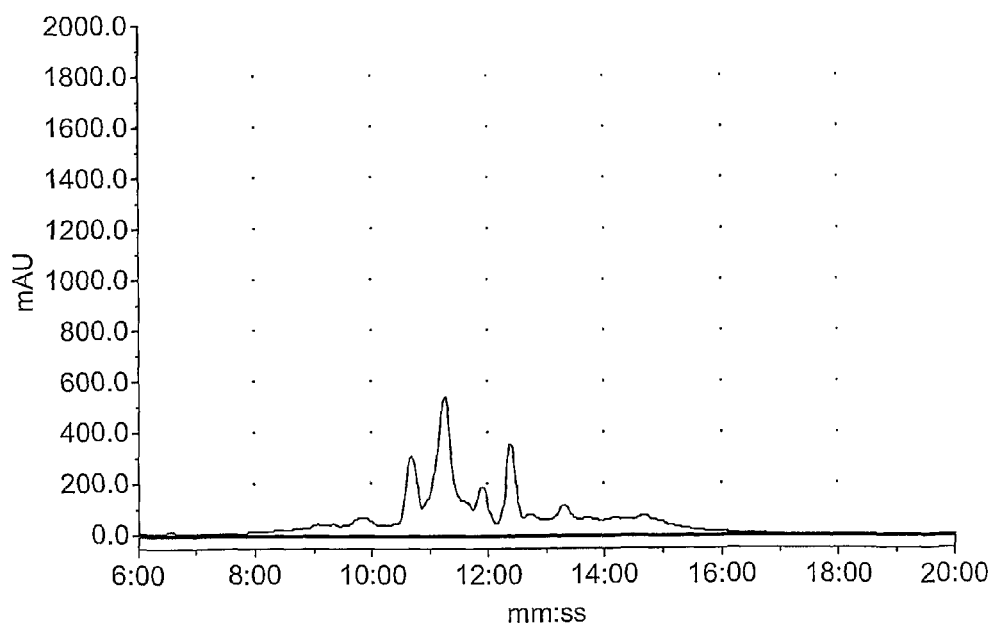
Figure 8:
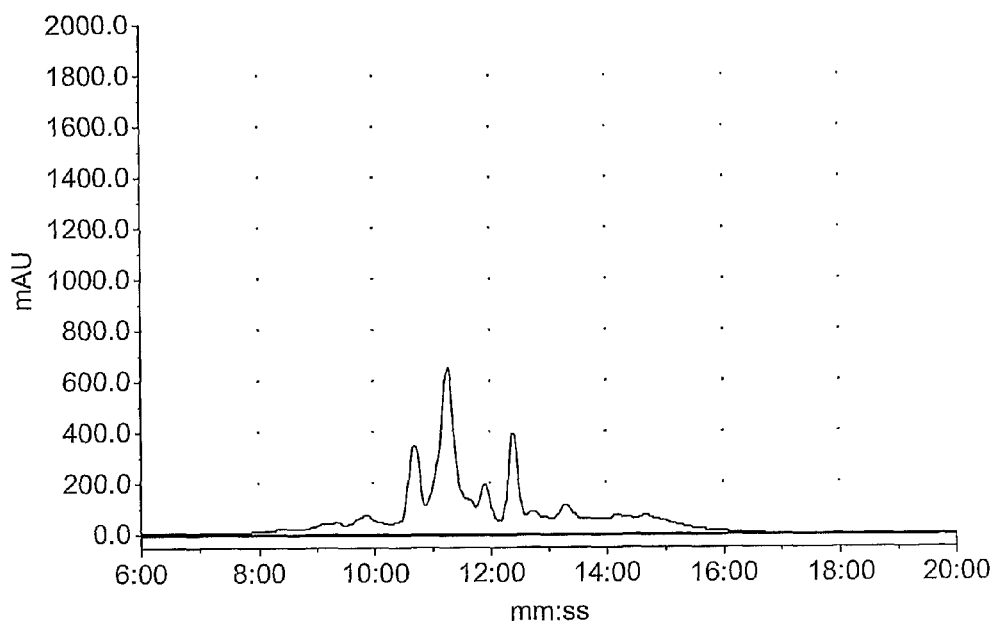
Figure 8:
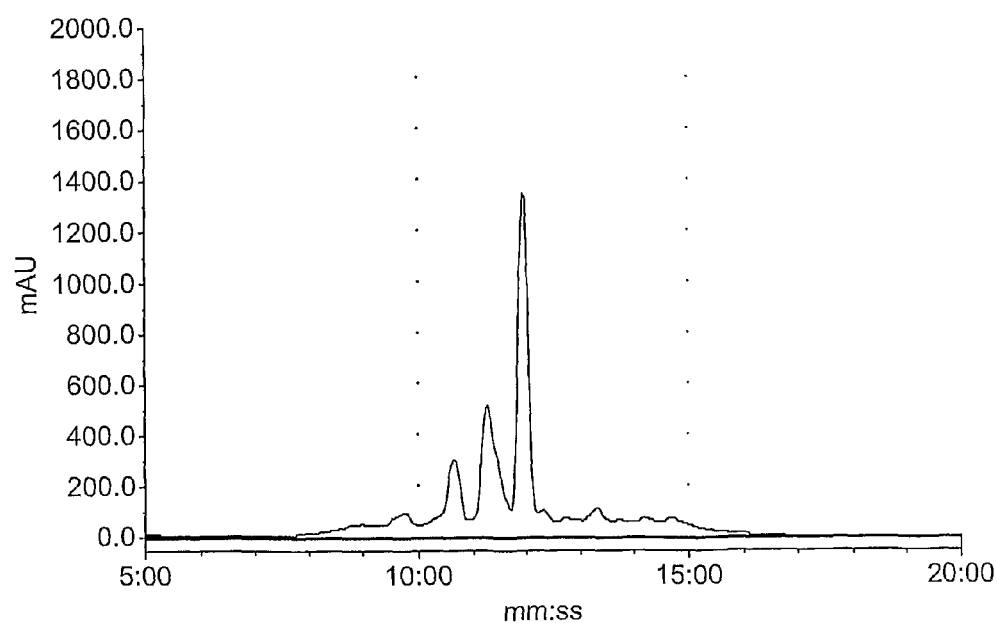

As shown in FIG. 8, the metabolic profiles of known, unlabelled, isatins 14 and 15 were similar, with near complete degradation observed after 60 min incubation.

Example 6

Uptake of [$^{18}$F]11 in Four Cancer Cell Lines

Cell Lines and Tumour Model.

The human ovarian carcinoma cell lines PEO1/4 were established and characterised as described in Wolf C. R. et al.[22] and Langdon S. P. et al[23]. Briefly, PEO1/4 cells were derived from the malignant ascites of a patient with a recurrent mucinous ovarian adenocarcinoma, before (PEO1) and after (PEO4) the onset of a clinical resistance to cisplatin chemotherapy in this patient. The radiation-induced murine fibrosarcoma (RIF-1) tumour cell line was originally characterised by Twentyman P. R. et al.[20]. The LNM35 tumour cells are a highly lymphogenous metastatic subline of the human large pulmonary carcinoma NCI-H460 cell line, as described in Kozaki K. et al.[24]. All cell lines were routinely maintained in RPMI 1640 medium (Invitrogen Ltd, Paisley, UK) supplemented with 10% foetal calf serum (BioWhittaker Europe Ltd, Verviers, Belgium), 2 mM L-glutamine, 100 U/mL penicillin, 100 µg/mL streptomycin and 0.25 µg/mL fungizone (Gibco, UK) at 37° C. in a humidified incubator with 5% CO2.

In vivo tumour models were established by subcutaneous injection of PEO1/4 ($10 \times 10^6$ cells, with v/v matrigel, BD Biosciences, Oxford, UK), RIF-1 ($5 \times 10^5$ cells) and LNM35 ($1 \times 10^6$ cells) on the back of 6-8 weeks old female nu/nu-BALB/c or male C3H/hej mice (Harlan, Bicester, Oxfordshire, UK). Tumour growth was monitored every two days using electronic callipers, and tumour volume estimated using $(\pi/6) \times L \times W \times D$ (L=length, W=width and D=depth). All animal work was done by licensed investigators in accordance with the United Kingdom's "Guidance on the Operation of Animals (Scientific Procedures) Act 1986" (HMSO, London, United Kingdom, 1990) and in full compliance with government regulations and guidelines on the welfare of animals in experimental neoplasia.

In Vitro [$^{18}$F]11 Uptake and Caspase 3 Activation Assays.

Cells were plated in triplicate in 12-well plates 2 or 3 days prior to the experiments and treated with the antineoplastic platinum-derived drug Cisplatin, 5-FU, the protein synthesis inhibitor cycloheximide (CHX) or the topoisomerase inhibitor etoposide (VP-16) (Sigma, UK) or corresponding vehicle at the indicated concentration and time. On the day of the experiment, ~10 µCi/well of [$^{18}$F]11 was added and allowed to accumulate into cells for 60 min at 37° C. Cells were collected, washed, and resuspended in 400 µL PBS. 260 µL of each sample were transferred in counting tubes and Fluorine-18 radioactivity was immediately determined using a Packard Cobra II gamma counter (Perkin Elmer, UK). Colorimetric caspase 3 activation assay was performed with 40 µL of each sample according to the instructions of the manufacturer (Caspase-Glo 3/7 assay, Promega, UK). Briefly, the cells were transferred in a white opaque 96-well plate, incubate for 30 min to 3 h with 50 µL caspase-Glo reagent and the enzymatic activity of caspase 3 was measured using a Multiskan Luminometer (Thermo Electron, UK). BCA Protein assay (Pierce, UK) was performed for all samples and datas are normalized and expressed as CCPMA or RLU (Relative Light Unit)/mg of protein.

In Vivo [$^{18}$F]11 Biodistribution and PET Imaging.

For biodistribution studies, tumour-bearing mice were treated with 10 mg/kg cisplatin or vehicle for 24 h, anesthetized with isofluorane/$O_2$/$N_2$O and injected i.v. in the lateral tail vein with ~100 µCi [$^{18}$F]11 for the indicated time. The different tissues were removed, weighted and placed in counting tubes for immediate Fluorine-18 radioactivity counting.

Tumour-bearing mice treated with Cisplatin (10 mg/kg for 24 h) or vehicle were scanned on a dedicated small animal PET scanner (quad-HIDAC; Oxford Positron Systems, Weston-on-the-Green, United Kingdom). Anesthetized animals were placed within a thermostatically controlled bed and positioned prone within the scanner. The bed was calibrated to provide a mouse rectal temperature of ~37° C. A bolus injection of [$^{18}$F]11 (~100 µCi) was given intravenously (i.v.) via the tail vein cannula and scanning commenced. Dynamic emission scans were acquired in list-mode format over 60 minutes. The acquired data were then sorted into 0.5-mm sinogram bins and 19 time frames ($0.5 \times 0.5 \times 0.5$ mm voxels; $4 \times 15$, $4 \times 60$, and $11 \times 300$ seconds) for image reconstruction, which was done by filtered back projection using a two-dimensional Hamming filter (cutoff 0.6). The image data-sets obtained were transferred to a SUN workstation (Ultra 10; SUN Microsystems, Santa Clara, Calif.) and visualized using the Analyze software (version 6.0; Biomedical Imaging Resource, Mayo Clinic, Rochester, Minn.). Cumulative images of the dynamic data composed of 0 to 1 minute after injection and 30 to 60 minutes after injection were used for visualization of radiotracer uptake and to define the regions of interest (ROI). The count densities were averaged for each ROI at each of the 19 time points to obtain a time versus radioactivity curve (TAC) for the ROIs. Tumour TAC was normalized to that of heart at each of the time points to obtain the normalized uptake value (NUV). The [$^{18}$F]9 data from muscle were used as internal input function for normalizing tumour data. The NUV at 60 minutes after injection (NUV60), the area under the NUV curve (AUC) calculated as the integral of NUV from 0 to 60 minutes, and the fractional retention of tracer (FRT), the radioactivity at 60 minutes relative to that at 2.5 minutes, were used for comparisons. FRT is a useful variable in that it indicates the proportion of radiotracer delivered to the tumour that is retained. It therefore normalizes tumor [$^{18}$F]9 uptake to delivery.

Results.

Figure 9:
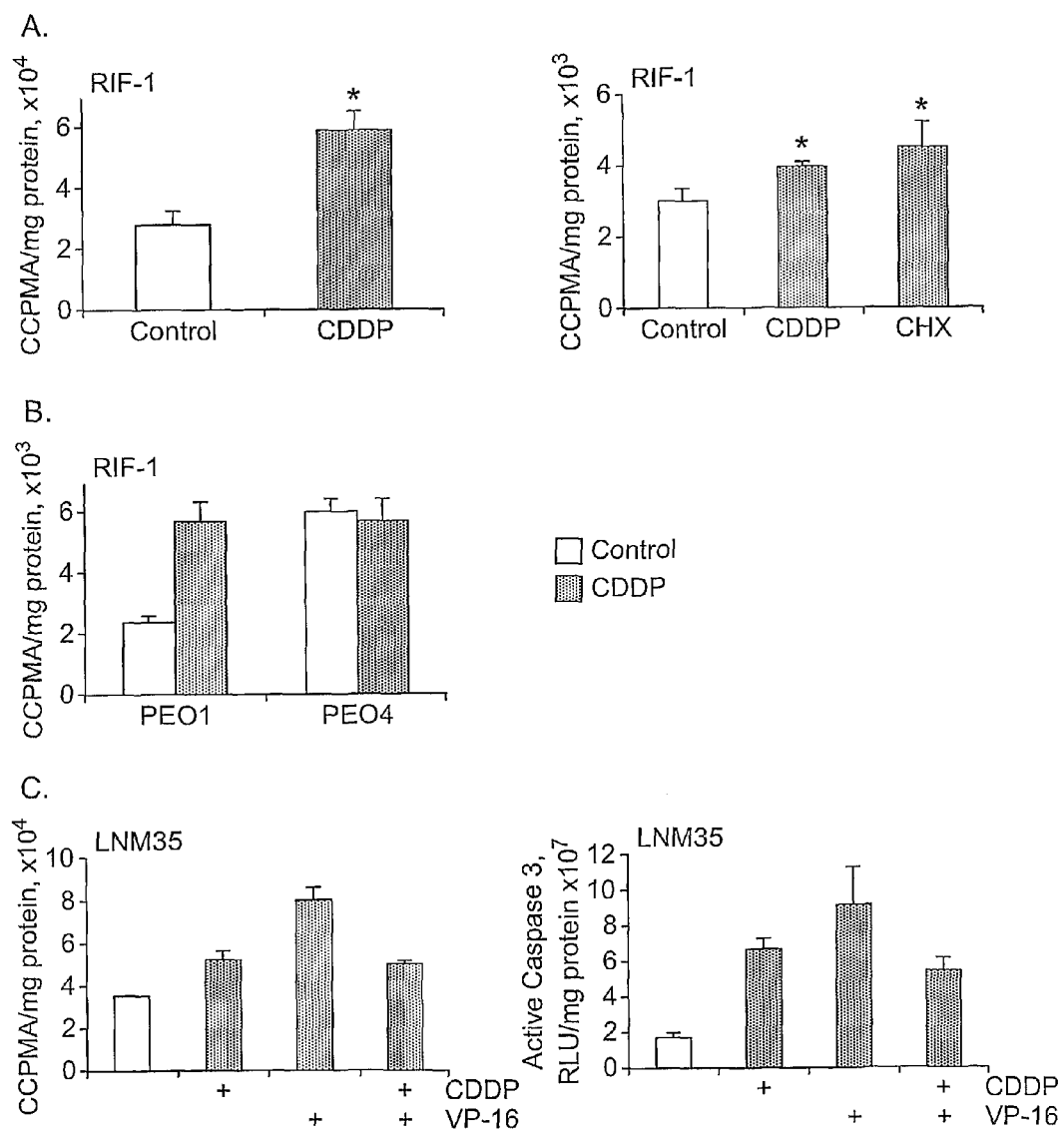

As shown in FIG. 9, all the drug-treated cells show significantly increased [$^{18}$F]11 uptake compared to the control (vehicle-treated), except for the cisplatin resistant ovarian cancer cells (PEO4) as expected. Moreover, the increased [$^{18}$F]9 uptake in drug-treated LNM35 cells correlates with the active caspase-3 amount in cells and also revealed the antagonism between CDDP and VP-16 treatments.

Table 3 indicates a significant increased uptake of [$^{18}$F]11 in the tumour of CDDP treated mice bearing PEO1 xenografts, whereas the CDDP-resistant PEO4 tumours are not showing differences in uptake between control and treated. The [$^{18}$F]11 uptake in the other tissues are not significantly different between control and treated, except for the spleen and muscle of PEO1 tumours bearing mice.

TABLE 3

60 min biodistribution of [$^{18}$F]11 in control and CDDP treated mice with PEO1, PEO4 or RIF-1 xenograft.

| | | PEO1 | PEO4 | RIF-1 |
|---|---|---|---|---|
| Lung | Control | 4.25 ± 0.57 | 3.31 ± 0.83 | 4.47 ± 1.00 |
| | CDDP | 4.90 ± 1.05 | 4.73 ± 1.78 | 3.23 ± 0.43 |
| Liver | Control | 9.98 ± 2.51 | 6.71 ± 1.56 | 11.36 ± 2.39 |
| | CDDP | 8.20 ± 2.09 | 8.22 ± 2.89 | 10.58 ± 4.64 |
| Spleen | Control | 1.19 ± 0.26 | 1.26 ± 0.45 | 1.85 ± 0.19 |
| | CDDP | 1.65 ± 0.22* | 1.81 ± 0.80 | 1.85 ± 0.76 |
| S. Intestine | Control | 4.27 ± 0.78 | 10.37 ± 10.58 | 14.93 ± 12.68 |
| | CDDP | 9.09 ± 5.82 | 10.43 ± 14.36 | 11.08 ± 6.00 |
| L. Intestine | Control | 1.81 ± 0.37 | 2.40 ± 1.88 | 2.66 ± 0.67 |
| | CDDP | 3.24 ± 1.81 | 2.89 ± 0.93 | 2.88 ± 1.52 |
| Kidney | Control | 6.59 ± 1.94 | 8.04 ± 4.24 | 8.49 ± 2.00 |
| | CDDP | 8.53 ± 3.64 | 7.96 ± 3.34 | 5.50 ± 2.59 |
| Muscle | Control | 0.98 ± 0.14 | 0.88 ± 0.36 | 1.76 ± 1.33 |
| | CDDP | 1.34 ± 0.28* | 1.13 ± 0.22 | 1.09 ± 0.54 |
| Bone | Control | 0.64 ± 0.09 | 1.12 ± 0.47 | 1.06 ± 0.49 |
| | CDDP | 1.51 ± 1.02 | 1.44 ± 0.66 | 1.78 ± 1.72 |
| Tumour | Control | 1.37 ± 0.25 | 1.66 ± 0.41 | 0.96 ± 0.10 |
| | CDDP | 2.96 ± 1.25* | 2.15 ± 0.79 | 1.31 ± 1.04 |

*Student's t-test, p < 0.005.

Figure 10:
Figure 11:
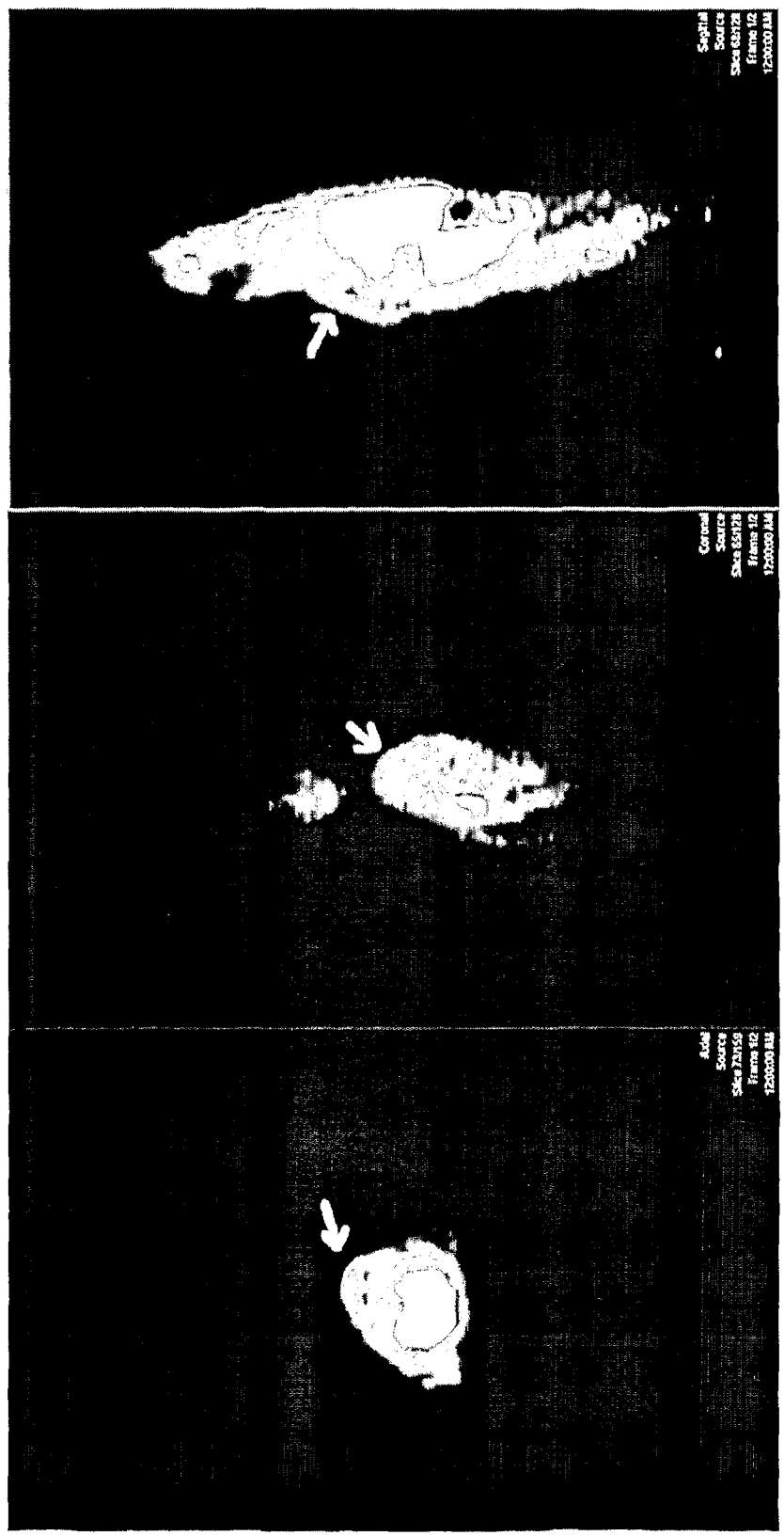

The PET images of three CDDP-treated mice with PEO1, PEO4 and RIF-1 xenografts (FIG. 10) revealed a significant uptake of [$^{18}$F]11 in the tumour.

All of the following documents are herein incorporated by reference:

Example 7

Uptake of [$^{18}$F]11 into Apoptotic Cells

Figure 13:
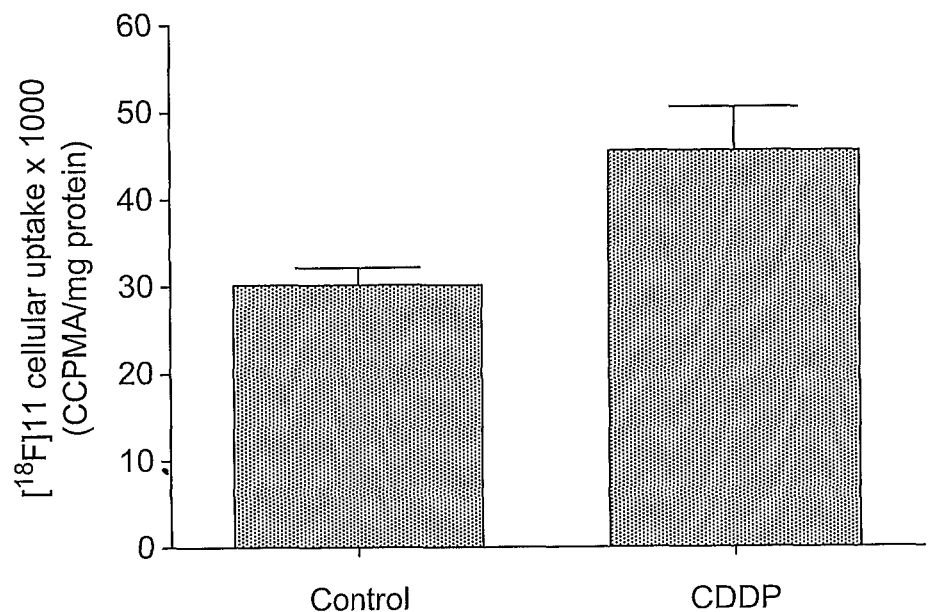

RIF-1 cells were treated with vehicle (0.1% DMSO) or cis-diamminedichloroplatinum (ii) (ciplatin) (CDDP) (100 μM) for 48 h. The cells were then incubated with [$^{18}$F]11 for 1 h, washed and analysed for radioactivity. As show in FIG. 13, the cellular assay indicated a c.a. 1.5-fold increase in uptake of [$^{18}$F]11 in apoptotic cells. Data are expressed as decay-corrected counts per min averaged per milligram of total cellular protein. Data are mean±SEM, done in triplicate.

Figure 14:
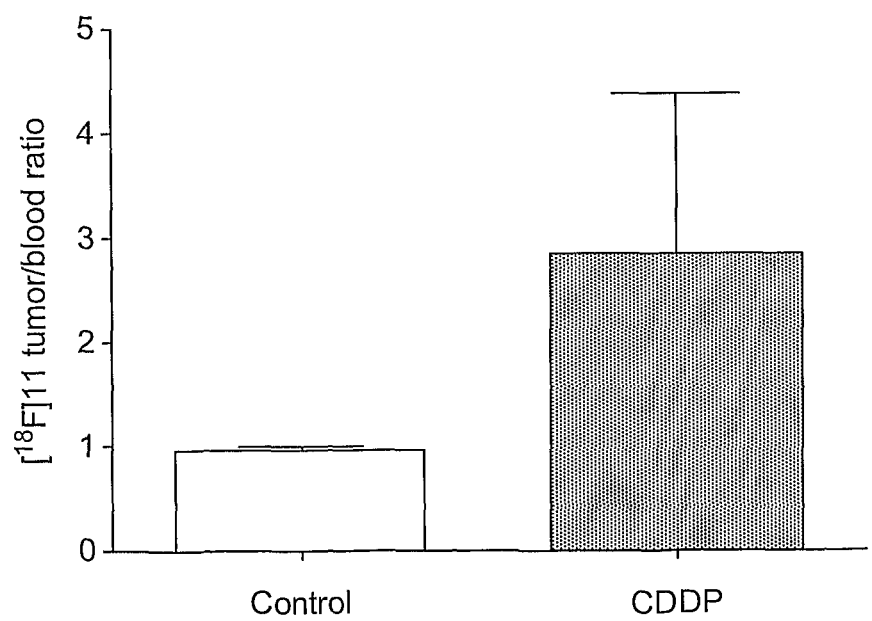

RIF-1 tumor was treated with vehicle (50% DMSO) or CDDP (10 mg/kg single dose). The [$^{18}$F]-derived radioactivity levels at 60 min post radiotracer injection were analysed and expressed as a ratio to that of blood. As shown in FIG. 14, the in vivo uptake studies in RIF-1 tumour bearing mice also showed a c.a. 1.5-fold increase in uptake of [$^{18}$F]11 for treated mice over vehicle treated mice. Data are mean±SEM and n=8 mice per group.

Example 8

Functionality of [$^{18}$F]11 as an Apoptosis Imaging Tracer

The in vivo experimental model of tumour apoptosis was established by subcutaneous injection of 38C13 murine lymphoma cells (5000 cells) on the back of 6-8 weeks old male C3H/hej mice (Harlan, Bicester, Oxfordshire, UK). When xenografts reached ~100 mm3, the mice were treated with cyclophosphamide (CPA, 100 mg/kg) or vehicle for 24 h and then scanned on a dedicated small animal PET scanner (Siemens Inveon PET module). Anesthetized animals were placed within a thermostatically controlled bed and positioned prone within the scanner. A bolus injection of [$^{18}$F]11 (~100 μCi) was given intravenously (i.v.) via the tail vein cannula and scanning commenced.

Dynamic emission scans were acquired in list-mode format over 60 minutes. The acquired data were then sorted into 0.5-mm sinogram bins and 19 time frames for image reconstruction, which was done by filtered back projection. The image data-sets obtained were visualized using the Siemens Inveon Research Workplace software. Cumulative images of the dynamic data were used for visualization of radiotracer uptake and to define the regions of interest (ROI). The count densities were averaged for each ROI at each of the 19 time points to obtain a time versus radioactivity curve (TAC) for the ROIs (see FIG. 15).

Tumour TAC was normalized to that of whole body at each of the time points to obtain the normalized uptake value (NUV). The NUV at 60 minutes after injection (NUV60) and the area under the NUV curve (AUC) calculated as the integral of NUV from 0 to 60 minutes were used for comparisons (See FIG. 16).

After the scan, the different tissues were removed, weighted and placed in tubes for immediate Fluorine-18 radioactivity counting to assess the [$^{18}$F]11 biodistribution (See Table 4, below).

Figure 17:
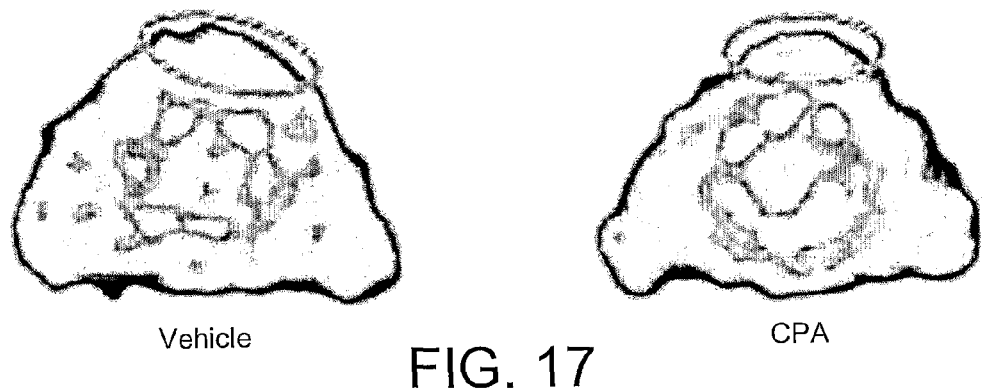
FIG. 17 is a representative OSEM3D reconstruction [$^{18}$F]11 PET images of two 38C13 xenograft-bearing mice treated with vehicle or cyclophosphamide. Circles indicate the tumour.

Representative OSEM3D reconstruction [$^{18}$F]11 PET images of two 38C13 xenograft-bearing mice treated with vehicle or cyclophosphamide are shown in FIG. 17, wherein the circles indicate the tumour.

Figure 15:
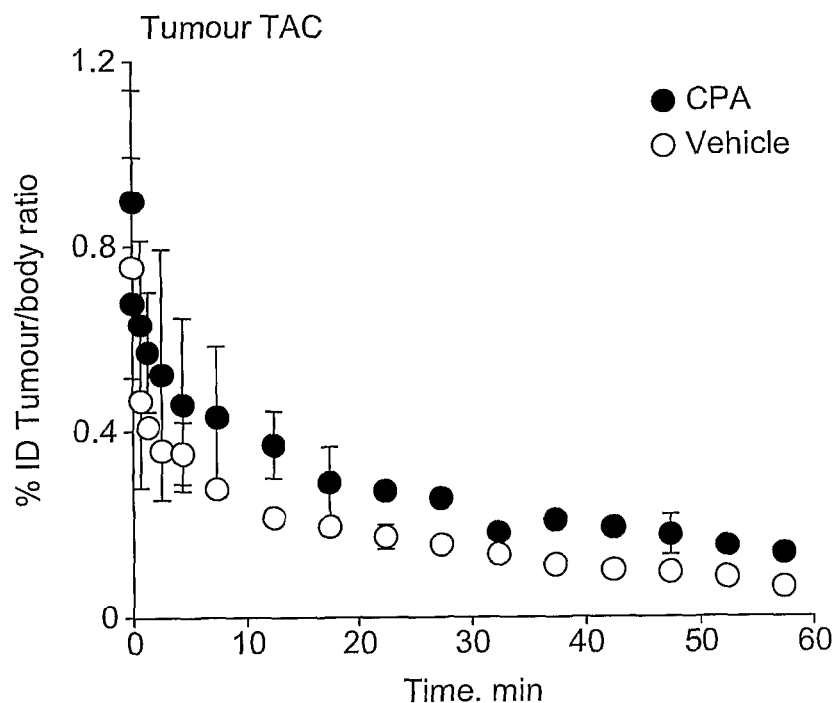
FIG. 15 shows the biodistribution of [$^{18}$F]11 in tumours treated with cyclophosphamide (CPA, 100 mg/kg) or vehicle, wherein the count densities were averaged for each region of interest at each of the 19 time points to obtain a time versus radioactivity curve (TAC) for the regions of interest.
Figure 16:
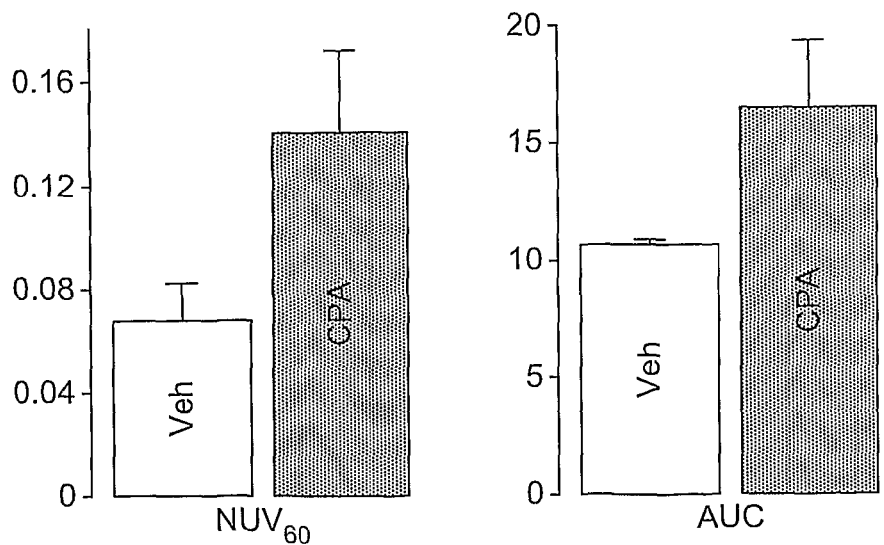
FIG. 16 is a histogram of the Normalised Uptake Value (NUV) at 60 minutes after injection (NUV$_{60}$), and the Area Under the NUV curve (AUC) calculated as the integral of NUV from 0 to 60 minutes in tumours treated with cyclophosphamide (CPA, 100 mg/kg) or vehicle (Veh).

The biodistribution results in Table 4 show a significant 2-fold increase in uptake of [$^{18}$F]11 in tumours of CPA-treated mice compared to the vehicle, which was confirmed by the semi-quantitative data generated from the PET imaging parameters, tumour TAC, NUV$_{60}$ and AUC (See FIGS. 15 and 16). Therefore, the biodistribution and PET scan data shown in FIGS. 15-17 and Table 4 demonstrate the potency of the [$^{18}$F]11 to detect the tumour apoptosis in vivo and describes for the first time the utility of a caspase-3 specific PET imaging agent for tumours.

TABLE 4

Biodistribution of [$^{18}$F]11 in tumours of CPA-treated mice compared to the vehicle.

| | % ID Tumour/blood ratio | |
|---|---|---|
| a. | Vehicle | CPA |
| Plasma | 1.98 ± 0.23 | 1.90 ± 0.09 |
| Blood | 1.00 ± 0.00 | 1.00 ± 0.00 |
| Heart | 1.31 ± 0.10 | 1.43 ± 0.16 |
| Lung | 4.27 ± 0.13 | 5.49 ± 0.66 |
| Liver | 10.60 ± 0.75 | 14.17 ± 1.55 |
| Spleen | 2.30 ± 0.38 | 1.81 ± 0.37 |
| Stomach | 1.95 ± 0.00 | 1.62 ± 0.19 |

TABLE 4-continued

Biodistribution of [$^{18}$F]11 in tumours of CPA-treated mice compared to the vehicle.

| | % ID Tumour/blood ratio | |
|---|---|---|
| a. | Vehicle | CPA |
| S. Intestine | 291.61 ± 28.68 | 83.12 ± 70.19 |
| L. Intestine | 6.07 ± 0.62 | 2.78 ± 0.64 |
| Feces | 13.28 ± 2.37 | 8.46 ± 0.91 |
| Kidney | 7.21 ± 0.33 | 7.23 ± 0.47 |
| Muscle | 1.22 ± 0.07 | 1.20 ± 0.07 |
| Bone | 0.87 ± 0.10 | 0.93 ± 0.07 |
| Tumour | 0.83 ± 0.10 | 1.24 ± 0.11 |
| Brain | 0.24 ± 0.02 | 0.23 ± 0.03 |
| Urine | 116.71 ± 19.47 | 43.64 ± 12.24 |

Example 9

Cellular Activity of Compound 11

The cellular activity of compound 11 was assessed using an enzyme assay and compared to that of compound 14.

Radiation-induced murine fibrosarcoma RIF-1 cells were treated for 15 min with the caspase inhibitors z-VAD-fmk (100 µM), compound 11 and compound 14, prior to apoptosis induction with cisplatin (100 µM) for 48 h. The Δ-PARP immunoblot band corresponds to the endogenous 89 kDa large fragment of PARP resulting from caspase 3 cleavage. α-tubulin was used as a loading control.

Figure 18:
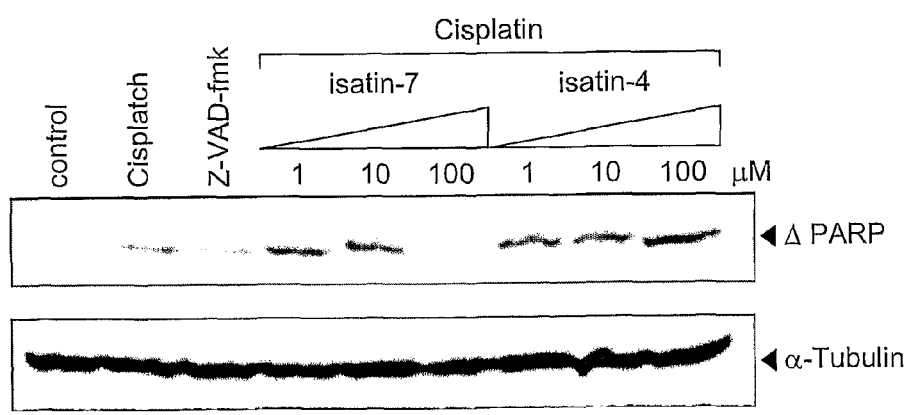
FIG. 18 shows the inhibitory activity of compound 11 (labeled as 'isatin-7') and compound 14 (labeled as 'isatin-4') on the caspase-3 cognate target poly(ADP-ribose) polymerase (PARP).

As shown in FIG. 18, the pre-incubation of RIF-1 cells with compound 11, but not compound 14, disrupted the induction of caspase-3 cognate target PARP by cisplatin induced apoptosis, demonstrating cellular inactivation of caspase-3 by compound 11.

To further establish the binding of compound 11 under conditions of drug-induced apoptosis, we evaluated the uptake of radiolabelled [$^{18}$F]11 in LNM35, RIF-1 and PEO1/4 cancer cells, as described above in Example 6 and shown in FIG. 9. All the drug-treated cells showed significantly increased [$^{18}$F]11 uptake compared to control, except for the cisplatin-resistant ovarian cancer cells (PEO4), as expected. Moreover, the increased [$^{18}$F]11 uptake in drug-treated LNM35 cells correlated with the amount of cellular active caspase-3 using the Caspase-Glo assay.

Example 10

Synthesis of [$^{18}$F]11 Using a Protected Precursor

The isatin radioligand [$^{18}$F]11 can be synthesised using a two step procedure as described in FIG. 2(i), FIG. 19 and in Example 3. A drawback of this radiosynthesis is the presence of a stable impurity, which reduces the specific activity of the formulated product (1-4 Ci/µmol). More fundamentally, the stable impurity is present in substantial mass (5-10 µg/mL), a value too large for clinical progression. Attempts to characterise the impurity in order to carry out toxicity tests have proved inconclusive, other than to confirm that the stable impurity, whilst not 'cold' fluorine-19 triazole compound, was isatin based.

HPLC analysis has confirmed that the impurity is the result of a side-reaction during radiosynthesis and not material present in the alkyne precursor. Examination of the isatin molecular architecture indicated only two sites of high chemical reactivity, the terminal alkyne function used in the click chemistry cycloaddition described above and the C-3 carbonyl position necessary for binding at the caspase-3 active site. A protecting group strategy for the C-3 carbonyl position has been investigated, in particular the protection of the C-3 carbonyl position as the acetal dioxolane, as shown in general formulae 38 and 43 below, wherein n=0, 1, 2, 3, 4, 5 or 6 and wherein x=a leaving group, for example mesylate, tosylate, nosylate or other sulfonate ester or halide:

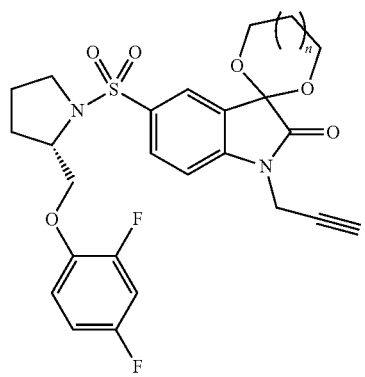

38

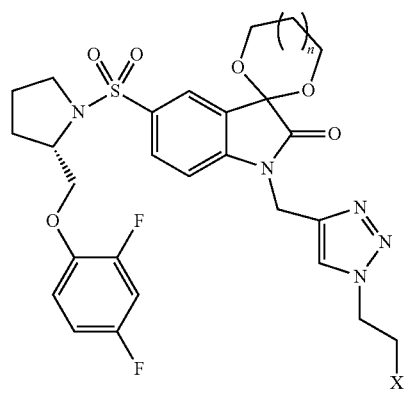

43

A protected alkyne, (S)-1-{[1'-[1-(2-Propynyl)]-(1'2'-dihydro-2'-oxospiro(1,3-dioxane-2,3'-[3H]indol)-5'-sulfonyl}-2-(2,4-difluorophenoxymethyl)-pyrrolidine (compound 39), and a protected triazole (compound 40), were synthesised as summarised in FIG. 20.

General experimental details have been previously described at the beginning of the Examples section and in Smith et al[29]. All reactions were carried out under an atmosphere of argon.

(S)-1-{[1'-[1-(2-Propynyl)]-(1'2'-dihydro-2'-oxospiro(1,3-dioxane-2,3'-[3H]indol)-5'-sulfonyl}-2-(2,4-difluorophenoxymethyl)-pyrrolidine (compound 39) was produced according to the following method. To a solution of compound 25 (92 mg, 0.2 mmol) in anhydrous toluene (6 mL) was added 1,3-propanediol (0.3 mL) and 4-toluenesulfonic acid (10 mg, 0.005 mmol). The solution was then refluxed for 24 h with the formed water removed by azeotropic distillation. The reaction mixture was then allowed to cool to ambient temperature and bulk solvent removed under reduced pressure. The sample was then redissolved in DCM (10 mL) and washed with sat. $Na_2CO_3$ (1×10 mL), water (1×10 mL) and brine (1×10 mL), then dried over $Na_2SO_4$. Column chromatography (2:1 ethyl acetate/hexanes) gave the desired product as the first fraction (colourless oil, 46 mg, 44%). HRMS (ESI)=519.1393 (M+H)$^+$. Calcd. for $C_{25}H_{25}F_2N_2O_6S$ 519.1401. $^1$H NMR (400 MHz, CDCl$_3$) δ 7.90 (d, J=1.8 Hz, 1H), 7.87 (dd, J=8.2 Hz, 1.8 Hz, 1H), 7.09 (d, J=8.2 Hz, 1H), 7.04-6.98 (m, 1H), 6.88-6.78 (m, 1H), 4.93 (t, J=12.1 Hz, 2H), 4.45 (d, J=2.4 Hz, 2H), 4.32-4.27 (m, 1H), 3.99-3.93 (m, 4H), 3.56-3.49 (m, 1H), 3.14-3.08 (m, 1H), 2.43-2.37 (m, 1H), 2.30 (t, J=2.4 Hz, 1H), 2.09-1.93 (m, 2H), 1.78-1.64 (m, 3H).

(S)-1-{[1'-[1-(2-Fluoroethyl)-1H-[1,2,3]-triazol-4-yl]-(1'2'-dihydro-2'-oxospiro(1,3-dioxane-2,3'-[3H]indol)-5'-sulfonyl}-2-(2,4-difluorophenoxymethyl)-pyrrolidine (compound 40) was produced according to the following method. To a solution of (S)-1-((1-(2-Fluoroethyl)-1H-[1,2,3]-triazol-4-yl)methyl)-5-(2(2,4-difluorophenoxymethyl)-pyrrolidine-1-sulfonyl)isatin) (compound 11) (12 mg, 0.02 mmol) in anhydrous toluene (4 mL) was added 1,3-propanediol (0.15 mL) and 4-toluenesulfonic acid (1 mg, 0.005 mmol). The solution was then refluxed for 24 h with the formed water removed by azeotropic distillation. The reaction mixture was then allowed to cool to ambient temperature and bulk solvent removed under reduced pressure. The sample was then redissolved in DCM (10 mL) and washed with sat. $Na_2CO_3$ (1×10 mL), water (1×10 mL) and brine (1×10 mL), then dried over $Na_2SO_4$. Chromatography (4:1 ethyl acetate/hexanes) gave the desired product as the first fraction (colourless oil, 7 mg, 58%). HRMS (ESI)=519.1393 (M+H)$^+$; Calcd. for $C_{25}H_{25}F_2N_2O_6S$ 519.1401. $^1$H NMR (400 MHz, $CDCl_3$) δ 5.7.84 (s, 1H), 7.81 (d, J=1.6 Hz, 1H), 7.67 (s, 1H), 7.43 (dd, J=8.4 Hz, 1.6 Hz, 1H), 7.04-6.98 (m, 1H), 6.88-6.79 (m, 1H), 4.96 (s, 1H), 4.92 (t, J=2.8 Hz, 2H), 4.79 (dt, J=46.6 Hz, 4.8 Hz, 2H), 4.64 (dt, J=27 Hz, 4.8 Hz, 2H), 4.29 (dd, J=8.4 Hz, 2.6 Hz, 1H), 4.00-3.89 (m, 4H), 3.53-3.48 (m, 1H), 3.10-3.07 (m, 1H), 2.43-2.37 (m, 1H), 2.05-1.92 (m, 2H), 1.75-1.65 (m, 3H).

[$^{18}$F]11 can then be synthesised using one or more of these protected precursors. A typical radiochemistry reaction with the protected alkyne precursor 39 is illustrated in FIG. 21. The use of such a protected alkyne precursor prevents undesirable side reactions at the C-3 position.

To an aqueous solution of copper(II) sulfate hexahydrate (0.51 mg, 2.06 μmol, 25 μL) under nitrogen sodium ascorbate (2.53 mg, 12.79 μmol) in sodium phosphate buffer (pH 6.0, 250 mM, 25 μL), alkyne acetale precursor (1.0 mg, 1.93 μmol) (compound 39) in DMF (25 μl), and [$^{18}$F]-fluoroethylazide (1.27 mCi) (compound 27) in acetonitrile (100 μL) were added. The reaction mixture was heated to 80° C. for 30 min (see FIG. 22). After addition of hydrochloric acid (6 N, 100 μL), the stirred mixture was heated using a microwave cavity (2 s, 50 W, set temperature 80° C.). After adding of HPLC mobile phase (50 μL, water containing 50% of MeOH with 35% MeCN) the mixture was purified by preparative HPLC (see FIG. 23). The [$^{18}$F]11 was isolated with 24% decay-corrected radiochemical yield (ref. to starting [$^{18}$F]-fluoroethylazide) and formulated using C18-SepPak SPS in PBS/10% EtOH. The level of stable impurity co-eluting with [$^{18}$F]11 was 0.84 μg/mL. The specific radioactivity was 0.05 Ci/μmol (2 GBq/μmol). (see FIG. 24).

Analagous protected precursors can of course be used to synthesize the other compounds of the present invention.

Example 11

Comparison of Uptake of [$^{18}$F]11 and [$^{18}$F]42 into Apoptotic Cells

A further aspect of the project has involved analysis of the weak isatin caspase-3 inhibitor N-[1-(2-Fluoroethyl)-1H-[1,2,3]-triazol-4-yl]isatin (compound 42). This compound was synthesised using N-(2-Propynyl)isatin (compound 41) as shown in FIG. 25. Compound [$^{18}$F]42 possesses the core isatin framework, allowing the compound to bind to activated caspase-3 in the conventional isatin binding mode, and also the radiolabelled triazole functionality. However, [$^{18}$F]42 lacks the pyrrolidine sulphonamide functionality that confers high affinity and selectivity for caspase-3. [$^{18}$F]42 was investigated in cell uptake assays for direct comparison with [$^{18}$F]11. The purpose of this was to examine the uptake profiles of the compounds in an effort to determine if uptake was the result of increased cell permeability, a characteristic trait of apoptotic cells, or the result of caspase-3 binding. Unlike [$^{18}$F]11, there was no increase in [$^{18}$F]42 binding following drug treatment (see FIG. 26), supporting the notion that [$^{18}$F]11 binding is due to caspase 3 activation.

N-(2-Propynyl)isatin (compound 41) was synthesised as described in Smith et al[29](alkynes 12 and 13). $^1$H NMR (600 MHz, $CDCl_3$) δ 7.65-7.61 (m, 2H), 7.19-7.12 (m, 2H), 4.61 (s, 2H), 2.30 (s, 1H).

N-[1-(2-Fluoroethyl)-1H-[1,2,3]-triazol-4-yl]isatin (compound 42) was synthesised as described in Smith et al[29] (triazoles 14 and 15). $^1$H NMR (600 MHz, $CDCl_3$) δ 7.76 (s, 1H), 7.63-7.57 (m, 2H), 7.34 (d, J=8.4 Hz, 1H), 7.13 (t, J=3.6 Hz, 1H), 5.03 (s, 2H), 4.81 (dt, J=46.8 Hz, 4.8 Hz, 2H), 4.68 (dt, J=27 Hz, 4.8 Hz, 2H).

N.B. Due to an error in numbering, compounds 15 and 21 are in fact the same compound.

REFERENCES

1. Lahorte et al. (2004) *European Journal of Nuclear Medicine and Molecular Imaging.* 31.887-919.
2. Boersma et al. (2005) *Journal of Nuclear Medicine.* 46, 2035-2050.
3. Aloya, R. et al. (2006) *Apoptosis.* 11, 2089-2101.
4. Damianovich, M. et al. (2006) *European Journal of Nuclear Medicine and Molecular Imaging.* 33, 281-291.
5. WO 2005/067388
6. Neuss, M. et al (2001). *Cardiovascular Drugs and Therapy.* 15, 507-523.
7. Lee, D. et al (2000) *Journal of Biological Chemistry.* 275, 16007-16014.
8. Lee, D. et al. (2001) *Journal of Medicinal Chemistry.* 44, 2015-2026
9. Chu, W. et al (2005) *Journal of Medicinal Chemistry.* 48. 7637-7647
10. Chu, W. et al (2007) *Journal of Medicinal Chemistry.* 50. 3751-3755.
11. WO 2005/053752
12. Faust, A. et al (2007) *Quarterly Journal of Nuclear Medicine and Molecular Imaging.* 51. 67-71
13. Kopka, K. et al (2006) *Journal of Medicinal Chemistry.* 49, 6704-6715.
14. Zhou, D. et al (2006) *Bioorganic and Medicinal Chemistry Letters.* 16, 5041-5046.
15. WO 2006/067376
16. Glaser et al (2007) *Bioconjugate Chemistry.* 18. 989-993
17. Wipf, P. et al (2001) *Tetrahedron.* 57, 283-296.
18. Barthel, H. et al (2004) *British Journal of Cancer.* 90, 2232-2242.
19. Aboagye, E. O. et al, (1997) *Biochemical Pharmacology.* 54, 1217-1224.
20. Twentyman, P. R. et al. (1980) *J Natl. Cancer Inst.* 64, 595-604
21. Workman, P., et al (1998) *British Journal of Cancer.* 77, 1-10.
22. Wolf, C. R. et al. (1987) Int. J. Cancer. 39, 695-702

23. Langdon, S. P. et al (1988) *Cancer Research.* 48, 6166-6172
24. Kozaki, K et al (2000) *Cancer Research.* 60, 2535-40
25. Schirrmacher, R. et al (2008) Tet. Lett. 49, 4824-4827.
26. Marik, J. and Sutcliffe, J. L. (2006) Click for PET: Rapid preparation of [$^{18}$F]fluoropeptides using Cu$^I$ catalyzed 1,3-dipolar cycloaddition. *Tet. Lett.* 47, 6681-6684
27. Sirion, U. et al, (2007) An efficient F-18 labeling method for PET study: Huisgen 1,3-dipolar cycloaddition of bioactive substances and F-18-labeled compounds. *Tet. Lett.,* 48, 3953-3957
28. Li, Z, et al. (2007) Click Chemistry for $^{18}$F-Labeling of RGD Peptides and microPET Imaging of Tumor Integrin $\alpha_v\beta_3$ expression. *Bioconjugate Chem.,* 18, 1987-1994.
29. Smith G. et al, (2008) Design, Synthesis and Biological Characterization of a Caspase 3/7 Selective Isatin Labeled with 2-[$^{18}$F]fluoroethylazide. *Journal of Medicinal Chemistry.* 51. 8057-8067

The invention claimed is:

1. A compound of formula A:

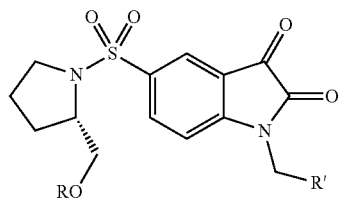

formula A or a salt or hydrate thereof, wherein

R is 3-fluorophenyl, 2,4-difluorophenyl, 3,5-difluorophenyl, an optionally substituted tetrahydropyran, an optionally substituted diazine or an optionally substituted triazole;

R' is an optionally substituted phenyl or an optionally substituted triazole; and wherein R and R' are chosen such that when R' is an optionally substituted phenyl, R is an optionally substituted triazole.

2. The compound of claim 1, wherein the optionally substituted triazole is substituted with a substituted alkyl group.

3. The compound of claim 1, wherein R and R' are defined as follows:

| Compound No. | R | R' |
|---|---|---|
| 6 | 2,4-difluorophenyl | triazole-CH₂F |
| 7 | 2,4-difluorophenyl | triazole-(CH₂)₂F |
| 8 | 2,4-difluorophenyl | triazole-(CH₂)₃F |
| 9 | 2,4-difluorophenyl | triazole-(CH₂)₄F |
| 11 | 2,4-difluorophenyl | triazole-N-(CH₂)₂F |
| 29 | 2,4-difluorophenyl | triazole-N-CH₂F |
| 30 | 2,4-difluorophenyl | triazole-N-(CH₂)₃F |
| 31 | 2,4-difluorophenyl | triazole-N-(CH₂)₄F |
| 12 | triazole-N-(CH₂)₂F | 4-fluorophenyl |

-continued

| Compound No. | R | R' |
|---|---|---|
| 32 | 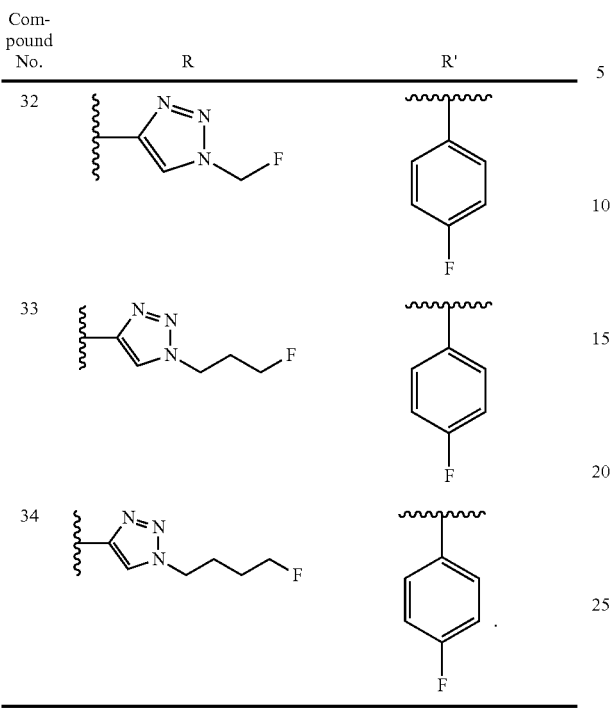 | |
| 33 | | |
| 34 | | |

4. The compound of claim 1, additionally comprising an imaging moiety.

5. The compound of claim 4, wherein the imaging moiety is $^{18}F$.

6. A pharmaceutical composition comprising the compound of claim 1, and optionally one or more additional active ingredients, pharmaceutically acceptable excipients, carriers or diluents.

7. A compound of formula A:

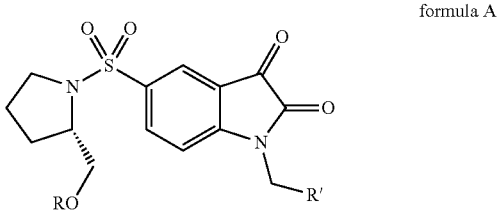

formula A or a salt, hydrate or prodrug thereof, wherein R is selected from the group consisting of 3-fluorophenyl, 2,4-difluorophenyl and 3,5-difluorophenyl; and wherein R' is a 2-fluoroethyl-substituted triazole.

8. A compound of formula [$^{18}F$]11:

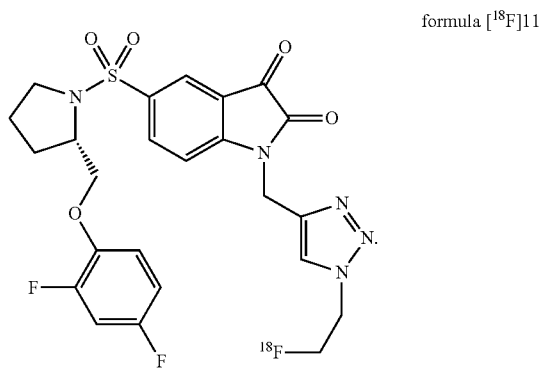 [SMILES: O=C1C(=O)N(Cc2cn(CC[18F])nn2)c2ccc(S(=O)(=O)N3CCC[C@H]3COc3ccc(F)cc3F)cc21]

formula [$^{18}F$]11

* * * * *